US009527810B2

(12) United States Patent
Adam et al.

(10) Patent No.: US 9,527,810 B2
(45) Date of Patent: Dec. 27, 2016

(54) (3,4-DICHLORO-PHENYL)-((S)-3-PROPYL-PYRROLIDIN-3-YL)-METHANONE HYDROCHLORIDE AND MANUFACTURING PROCESSES

(71) Applicant: Hoffmann-La Roche Inc., Little Falls, NJ (US)

(72) Inventors: Jean-Michel Adam, Village-Nuef (FR); Charles Alois Dvorak, Palo Alto, CA (US); Daniel Fishlock, Verona, NJ (US); Eric R. Humphreys, San Bruno, CA (US); Hans Iding, Rheinfelden (DE); Christophe Pfleger, Mulhouse (FR); Pankaj D. Rege, Hoboken, NJ (US); Xianqing Shi, Morris Plains, NJ (US); Justin Vitale, San Mateo, CA (US); Shaoning Wang, Basel (CH); Marian Zajac, Dielsdorf (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 14/522,775

(22) Filed: Oct. 24, 2014

(65) Prior Publication Data

US 2015/0045408 A1 Feb. 12, 2015

Related U.S. Application Data

(63) Continuation of application No. PCT/EP2013/058344, filed on Apr. 23, 2013.

(30) Foreign Application Priority Data

Apr. 25, 2012 (EP) ..................................... 12165527
Apr. 25, 2012 (EP) ..................................... 12165529

(51) Int. Cl.
| C07D 207/08 | (2006.01) |
| A61K 31/40 | (2006.01) |
| A61P 25/22 | (2006.01) |
| A61P 25/24 | (2006.01) |

(52) U.S. Cl.
CPC ................... *C07D 207/08* (2013.01)

(58) Field of Classification Search
CPC ................................................ C07D 207/08
See application file for complete search history.

(56) References Cited

U.S. PATENT DOCUMENTS

2008/0146607 A1* 6/2008 Iyer .................... C07D 205/04
514/300

FOREIGN PATENT DOCUMENTS

| CN | 101563319 A | 9/2012 |
| WO | 2008/074703 A1 | 6/2008 |
| WO | WO 2010/121022 A1 * | 10/2010 |

OTHER PUBLICATIONS

Caira, "Crystalline Polymorphism of Organic Compounds" Topics in Current Chemistry, Springer, Berlin, DE 198:163-208 (Jan. 1, 1998).
ISR for PCT/EP2013/058344, 2013.
Written Opinion for PCT/EP2013/058344, 2014.

* cited by examiner

*Primary Examiner* — Nyeemah A Grazier
*Assistant Examiner* — Amanda L Aguirre
(74) *Attorney, Agent, or Firm* — Robert C. Hall

(57) ABSTRACT

The present invention is concerned with a novel process for the preparation of a compound of formula I and its hydrates

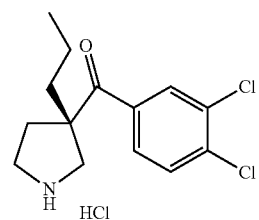

The compounds of formula I and the corresponding hydrates are pharmaceutically active substances.

11 Claims, 7 Drawing Sheets

(3,4-DICHLORO-PHENYL)-((S)-3-PROPYL-PYRROLIDIN-3-YL)-METHANONE HYDROCHLORIDE AND MANUFACTURING PROCESSES

CROSS REFERENCE TO RELATED APPLICATIONS

This application is a continuation of PCT/EP2013/058344 filed on Apr. 23, 2013, which claims priority to EP Patent Application No. 12165527.8 filed Apr. 25, 2012 and EP Patent Application No. 12165529.4 filed on Apr. 25, 2012, the disclosures of which are all incorporated herein by reference in their entirety.

FIELD OF THE INVENTION

The present invention provides a process to synthesize (3,4-Dichloro-phenyl)-((S)-3-propyl-pyrrolidin-3-yl)-methanone hydrochloride and its hydrates, in particular 3,4-Dichloro-phenyl)-((S)-3-propyl-pyrrolidin-3-yl)-methanone hydrochloride quarterhydrate and crystalline polymorphs of (3,4-Dichloro-phenyl)-((S)-3-propyl-pyrrolidin-3-yl)-methanone hydrochloride.

BACKGROUND OF THE INVENTION

PCT application WO 2008/074703 describes heteroaryl pyrrolidinyl and piperidinyl ketones which can be useful for treatment of diseases associated with triple reuptake inhibitors. Methods for the preparation of (3,4-Dichloro-phenyl)-((S)-3-propyl-pyrrolidin-3-yl)-methanone hydrochloride and its hydrates have been described in PCT application WO 2008/074703. However, these methods include a large number of individual reaction steps. Further, the methods known in the art exhibit a low yield or other disadvantages, which makes them unsuitable for the commercial large scale production.

SUMMARY OF THE INVENTION

It has surprisingly been found that by using the processes according to the present invention 3,4-Dichloro-phenyl)-((S)-3-propyl-pyrrolidin-3-yl)-methanone hydrochloride and its hydrates can be prepared more economically with less process steps under moderate reaction conditions with an outstanding yield. Further, crude intermediate products can mostly be used in subsequent reaction steps without the need of any additional purification steps.

DETAILED DESCRIPTION OF THE INVENTION

Figure 1:
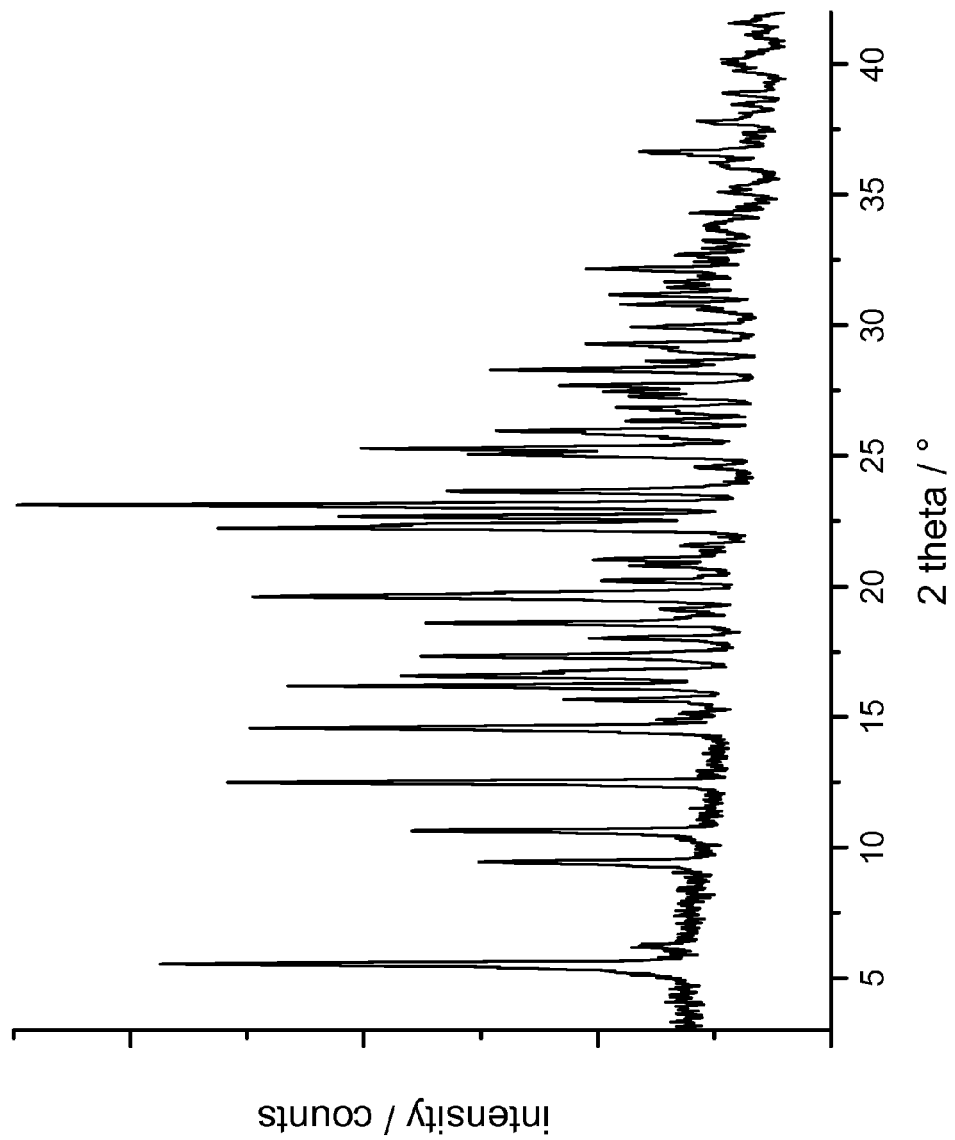
FIG. 1 is a powder X-ray diffraction pattern of a hydrochloride quarterhydrate of (3,4-Dichloro-phenyl)-((S)-3-propyl-pyrrolidin-3-yl)-methanone.

The term "solvate" denotes crystal forms having either stoichiometric or nonstoichiometric amounts of a solvent incorporated in the crystal lattice. If the incorporated solvent is water, the solvate formed is a hydrate. Quarterhydrate means ¼ or 0.25 hydrate.

The term "$C_{1-4}$-alkyl" refers to methyl (Me), ethyl, propyl, isopropyl (i-Pr), butyl or isobutyl, in particular methyl.

The terms "pharmaceutically acceptable carrier" and "pharmaceutically acceptable auxiliary substance" refer to carriers and auxiliary substances such as diluents or excipients that are compatible with the other ingredients of the formulation.

The term "dialkylamine" refers to acyclic or cyclic secondary dialkylamines for example (but not limited to) diethylamine, morpholine or diisopropylamine, in particular to diethylamine and diisopropylamine, more particularly to diethylamine.

The phrase "formaldehyde source" refers for example to aqueous formaldehyde (usually >30%) or paraformaldehyde.

The term "Boc" refers to tert-butyloxy carbonyl (—C(=O)—O—C(CH$_3$)$_3$).

The term "room temperature" refers to 18-30° C., in particular 20-25° C., more particular to 20° C.

The term "pharmaceutical composition" encompasses a product comprising specified ingredients in pre-determined amounts or proportions, as well as any product that results, directly or indirectly, from combining specified ingredients in specified amounts. Particularly it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

The term "a chiral resolution" means separation of a racemic mixture in its enantiomers.

"Therapeutically effective amount" means an amount that is effective to prevent, alleviate or ameliorate symptoms of disease or prolong the survival of the subject being treated.

The term "approximately" in connection with degrees 2-theta values refers to ±0.2 degrees 2-theta.

The terms "pharmaceutically acceptable carrier" and "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. Particularly it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

"Therapeutically effective amount" means an amount that is effective to prevent, alleviate or ameliorate symptoms of disease or prolong the survival of the subject being treated.

The term "substantially pure" when used in reference to a polymorphic form of 3,4-Dichloro-phenyl)-((S)-3-propyl-pyrrolidin-3-yl)-methanone hydrochloride quarterhydrate refers to said polymorph being >90% pure. The polymorphic form of 3,4-Dichloro-phenyl)-((S)-3-propyl-pyrrolidin-3-yl)-methanone hydrochloride quarterhydrate does not contain more than 10% of any other compound, in particular does not contain more than 10% of any other polymorphic form of 3,4-Dichloro-phenyl)-((S)-3-propyl-pyrrolidin-3-yl)-methanone hydrochloride.

More particular, the term "substantially pure" when used in reference to a polymorphic form of 3,4-Dichloro-phenyl)-((S)-3-propyl-pyrrolidin-3-yl)-methanone hydrochloride quarterhydrate refers to said polymorph being >95% pure. The polymorphic form of 3,4-Dichloro-phenyl)-((S)-3-propyl-pyrrolidin-3-yl)-methanone hydrochloride quarterhydrate does not contain more than 5% of any other compound, in particular does not contain more than 5% of any other polymorphic form of 3,4-Dichloro-phenyl)-((S)-3-propyl-pyrrolidin-3-yl)-methanone hydrochloride.

Even more particular, the term "substantially pure" when used in reference to a polymorphic form of 3,4-Dichloro-phenyl)-((S)-3-propyl-pyrrolidin-3-yl)-methanone hydrochloride quarterhydrate refers to said polymorph being >97% pure. The polymorphic form of 3,4-Dichloro-phenyl)-((S)-3-propyl-pyrrolidin-3-yl)-methanone hydrochloride quarterhydrate does not contain more than 3% of any other compound, in particular does not contain more than 3% of any other polymorphic form of 3,4-Dichloro-phenyl)-((S)-3-propyl-pyrrolidin-3-yl)-methanone hydrochloride.

Most particular, the term "substantially pure" when used in reference to a polymorphic form of 3,4-Dichloro-phenyl)-((S)-3-propyl-pyrrolidin-3-yl)-methanone hydrochloride quarterhydrate refers to said polymorph being >99% pure. The polymorphic form of 3,4-Dichloro-phenyl)-((S)-3-propyl-pyrrolidin-3-yl)-methanone hydrochloride quarterhydrate does not contain more than 1% of any other compound, in particular does not contain more than 1% of any other polymorphic form of 3,4-Dichloro-phenyl)-((S)-3-propyl-pyrrolidin-3-yl)-methanone hydrochloride.

While the present invention has been described with reference to the specific embodiments thereof, it should be understood by those skilled in the art that various changes can be made and equivalents can be substituted without departing from the true spirit and scope of the invention. In addition, many modifications can be made to adapt a particular situation, material, composition of matter, process, process step or steps, to the objective spirit and scope of the present invention. All such modifications are intended to be within the scope of the claims appended hereto. All separate embodiments can be combined.

In detail, the present invention is concerned with a process to synthesize (3,4-Dichloro-phenyl)-((S)-3-propyl-pyrrolidin-3-yl)-methanone hydrochloride of formula I

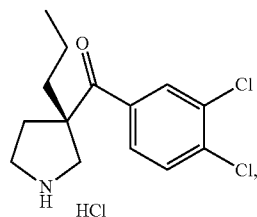

or a hydrate thereof.

This process provides an efficient method for producing compounds of formula I. Compared to the processes known in the art, the process of the present invention exhibits a higher yield, a shorter synthesis, moderate reaction conditions and other commercially relevant advantages.

A certain embodiment of the invention is (3,4-Dichloro-phenyl)-((S)-3-propyl-pyrrolidin-3-yl)-methanone hydrochloride quarterhydrate.

A certain embodiment of the invention is a crystalline polymorph of the compound as described herein, characterized by a X-ray powder diffraction pattern having at least two characteristic peak expressed in values of degrees 2-theta at approximately

| degree 2-theta |
|---|
| 5.5 |
| 9.4 |
| 10.6 |
| 12.5 |
| 14.6 |
| 16.2 |
| 16.6 |
| 17.3 |
| 18.6 |
| 19.6 |
| 22.2 |
| 22.7 |
| 23.1 |
| 23.7 |
| 25.3. |

A certain embodiment of the invention is a crystalline polymorph of the compound as described herein, characterized by a X-ray powder diffraction pattern having at least one characteristic peak expressed in values of degrees 2-theta at

| degree 2-theta |
|---|
| 5.5 ± 0.20 |
| 9.4 ± 0.20 |
| 10.6 ± 0.20 |
| 12.5 ± 0.20 |
| 14.6 ± 0.20 |
| 16.2 ± 0.20 |
| 16.6 ± 0.20 |
| 17.3 ± 0.20 |
| 18.6 ± 0.20 |
| 19.6 ± 0.20 |
| 22.2 ± 0.20 |
| 22.7 ± 0.20 |
| 23.1 ± 0.20 |
| 23.7 ± 0.20 |
| 25.3 ± 0.20. |

A certain embodiment of the invention is a crystalline polymorph of the compound as described herein, characterized by a X-ray powder diffraction pattern having at least one characteristic peak expressed in values of degrees 2-theta at approximately

| degree 2-theta |
| --- |
| 9.4 |
| 14.6 |
| 16.6 |
| 19.6 |
| 22.2. |

A certain embodiment of the invention is a crystalline polymorph of the compound as described herein, characterized by a X-ray powder diffraction pattern having at least one characteristic peak expressed in values of degrees 2-theta at

| degree 2-theta |
| --- |
| 9.4 ± 0.20 |
| 14.6 ± 0.20 |
| 16.6 ± 0.20 |
| 19.6 ± 0.20 |
| 22.2 ± 0.20. |

A certain embodiment of the invention is a crystalline polymorph of the compound as described herein, characterized by a X-ray powder diffraction pattern having characteristic peaks expressed in values of degrees 2-theta at approximately

| degree 2-theta |
| --- |
| 5.5 |
| 9.4 |
| 10.6 |
| 12.5 |
| 14.6 |
| 16.2 |
| 16.6 |
| 17.3 |
| 18.6 |
| 19.6 |
| 22.2 |
| 22.7 |
| 23.1 |
| 23.7 |
| 25.3. |

A certain embodiment of the invention is a crystalline polymorph of the compound as described herein, characterized by a X-ray powder diffraction pattern having characteristic peaks expressed in values of degrees 2-theta at

| degree 2-theta |
| --- |
| 5.5 ± 0.20 |
| 9.4 ± 0.20 |
| 10.6 ± 0.20 |
| 12.5 ± 0.20 |
| 14.6 ± 0.20 |
| 16.2 ± 0.20 |
| 16.6 ± 0.20 |
| 17.3 ± 0.20 |
| 18.6 ± 0.20 |
| 19.6 ± 0.20 |
| 22.2 ± 0.20 |
| 22.7 ± 0.20 |
| 23.1 ± 0.20 |

| degree 2-theta |
| --- |
| 23.7 ± 0.20 |
| 25.3 ± 0.20. |

A certain embodiment of the invention is a crystalline polymorph of the compound as described herein, characterized by a X-ray powder diffraction pattern having characteristic peaks expressed in values of degrees 2-theta at approximately

| degree 2-theta |
| --- |
| 9.4 |
| 14.6 |
| 16.6 |
| 19.6 |
| 22.2. |

A certain embodiment of the invention is a crystalline polymorph of the compound as described herein, characterized by a X-ray powder diffraction pattern having characteristic peaks expressed in values of degrees 2-theta at

| degree 2-theta |
| --- |
| 9.4 ± 0.20 |
| 14.6 ± 0.20 |
| 16.6 ± 0.20 |
| 19.6 ± 0.20 |
| 22.2 ± 0.20. |

A certain embodiment of the invention is a crystalline polymorph as described herein, characterized by the X-ray powder diffraction pattern as shown in FIG. 1.

A certain embodiment of the invention is a substantially pure crystalline polymorph of 3,4-Dichloro-phenyl)-((S)-3-propyl-pyrrolidin-3-yl)-methanone hydrochloride quarter-hydrate.

A certain embodiment of the invention is a crystalline polymorph as described herein, characterized by the following unit cell parameters

| | |
| --- | --- |
| a | 6.14 Å |
| b | 16.70 Å |
| c | 17.43 Å |
| alpha | 66.73° |
| beta | 81.47° |
| gamma | 86.51°. |

A certain embodiment of the invention is a crystalline polymorph as described herein, characterized by a X-ray powder diffraction pattern having at least one characteristic peak expressed in values of degrees 2-theta at approximately

| degree 2-theta |
| --- |
| 5.2 |
| 10.5 |
| 12.3 |
| 15.3 |
| 15.6 |
| 16.0 |
| 17.1 |
| 18.8 |

-continued

| degree 2-theta |
|---|
| 23.0 |
| 23.9 |
| 27.2 |
| 28.2 |
| 30.5. |

A certain embodiment of the invention is a crystalline polymorph as described herein, characterized by a X-ray powder diffraction pattern having at least one characteristic peak expressed in values of degrees 2-theta at

| degree 2-theta |
|---|
| 5.2 ± 0.20 |
| 10.5 ± 0.20 |
| 12.3 ± 0.20 |
| 15.3 ± 0.20 |
| 15.6 ± 0.20 |
| 16.0 ± 0.20 |
| 17.1 ± 0.20 |
| 18.8 ± 0.20 |
| 23.0 ± 0.20 |
| 23.9 ± 0.20 |
| 27.2 ± 0.20 |
| 28.2 ± 0.20. |
| 30.5 ± 0.20 |

A certain embodiment of the invention is a crystalline polymorph as described herein, characterized by a X-ray powder diffraction pattern having characteristic peaks expressed in values of degrees 2-theta at approximately

| degree 2-theta |
|---|
| 5.2 |
| 10.5 |
| 12.3 |
| 15.3 |
| 15.6 |
| 16.0 |
| 17.1 |
| 18.8 |
| 23.0 |
| 23.9 |
| 27.2 |
| 28.2 |
| 30.5. |

A certain embodiment of the invention is a crystalline polymorph as described herein, characterized by a X-ray powder diffraction pattern having characteristic peaks expressed in values of degrees 2-theta at

| degree 2-theta |
|---|
| 5.2 ± 0.20 |
| 10.5 ± 0.20 |
| 12.3 ± 0.20 |
| 15.3 ± 0.20 |
| 15.6 ± 0.20 |
| 16.0 ± 0.20 |
| 17.1 ± 0.20 |
| 18.8 ± 0.20 |
| 23.0 ± 0.20 |
| 23.9 ± 0.20 |
| 27.2 ± 0.20 |
| 28.2 ± 0.20 |
| 30.5 ± 0.20. |

Figure 2:
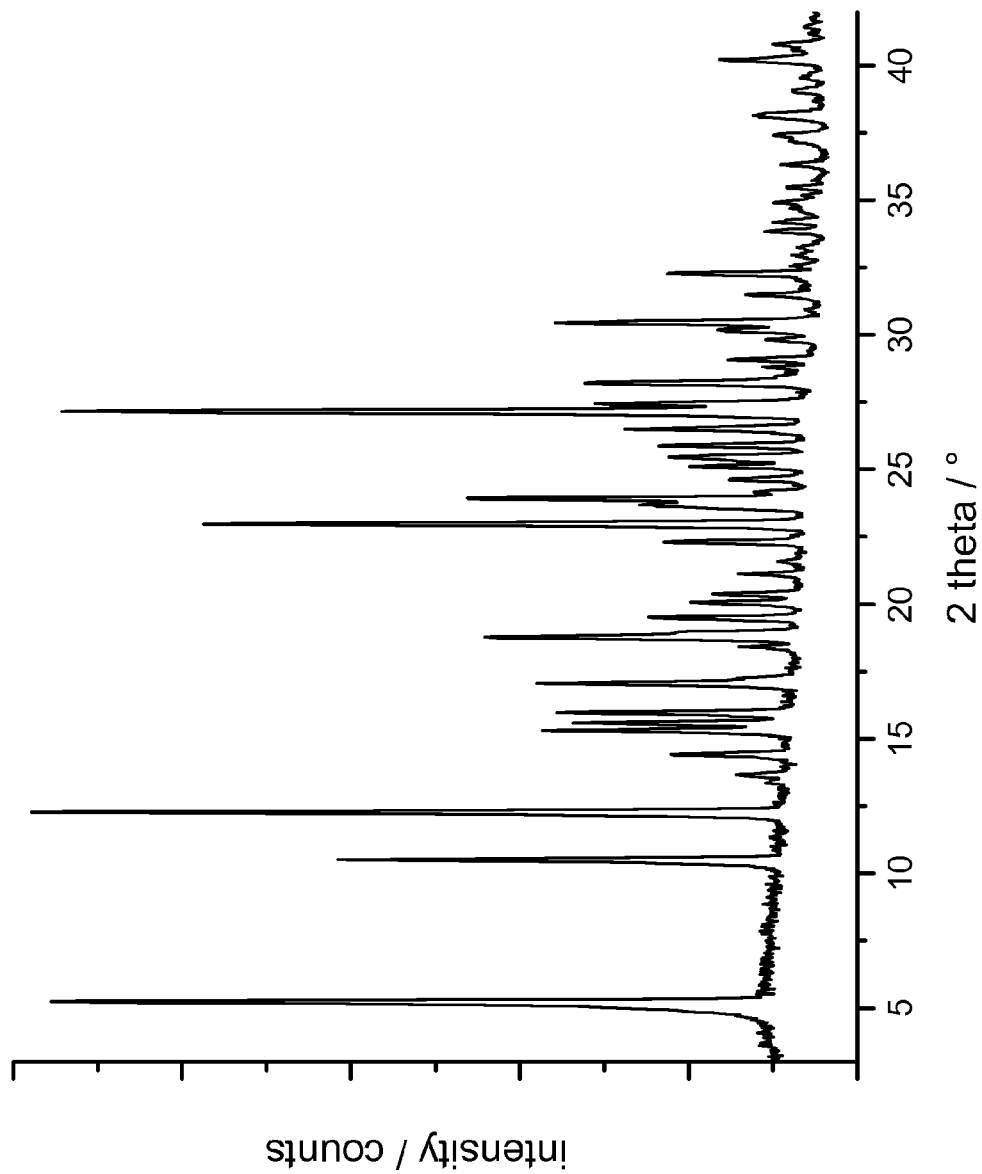
FIG. 2 is a powder X-ray diffraction pattern of a hydrochloride of (3,4-Dichloro-phenyl)-((S)-3-propyl-pyrrolidin-3-yl)-methanone.

A certain embodiment of the invention is a crystalline polymorph as described herein, characterized by the X-ray powder diffraction pattern as shown in FIG. 2.

A certain embodiment of the invention is a process to synthesize (3,4-Dichloro-phenyl)-((S)-3-propyl-pyrrolidin-3-yl)-methanone hydrochloride of formula I

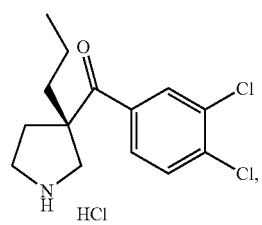

I or a hydrate thereof, comprising reaction of a compound of formula IV with a compound of formula VI,

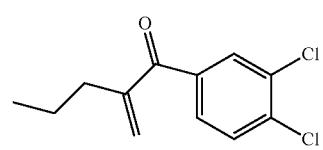

IV

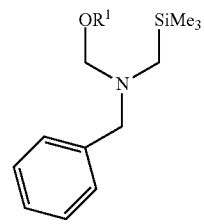

VI with $R^1$=H or $C_{1-4}$-alkyl, to yield a compound of formula VIII,

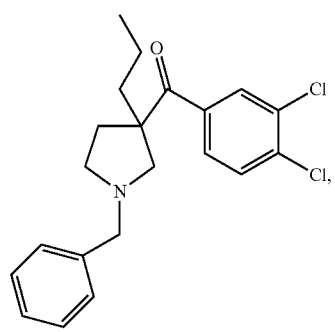

VIII and a) resolving the compound of formula VIII into its enantiomers followed by the deprotection of a compound of formula IX-1 to a compound of formula I,

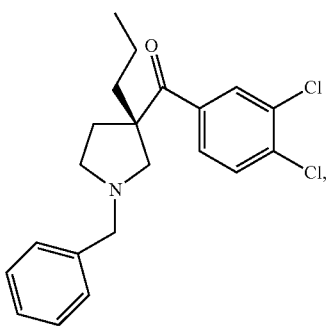

or b) deprotecting the compound of formula VIII to a compound of formula X followed by a chiral resolution to obtain a compound of formula I

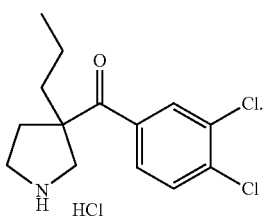

A certain embodiment of the invention is a process as described herein, where R¹ is hydrogen.

A certain embodiment of the invention is a process as described herein, where R¹ is methyl.

A certain embodiment of the invention is a process as described herein, leading to the quarterhydrate of a compound of formula I.

Compound II can be obtained for instance by the addition of butyl-metal reagent like for example butyl magnesium chloride or butyl magnesium bromide on an electrophile like for instance 3,4-dichlorbenzonitrile. Such a process has already bee described in the literature (see *J. Med. Chem.* 2006, 49, 1420-1432).

Another access consists in a Friedel-Crafts between valeroyl chloride, valeroyl anhydride or valeroyl acid on dichlorobenzene, in the presence of a suitable catalyst or promoter. Preferred conditions involve the use of valeroyl chloride in the presence of aluminum chloride (AlCl₃).

The reference process (DE2809022) is not suitable for large scale production, as valeroyl chloride is added to a room temperature mixture of AlCl₃ and 1,2-dichlorobenzene upon which a significant exotherm occurs and upon further heating, the reaction appears to start in an uncontrolled manner.

A certain embodiment of the invention is that when firstly charging AlC₃ and 1,2-dichlorobenzene and heated the mixture to 60-100° C., in particular between 70-90° C. more particular to 80° C.±1° C., and secondly slowly adding valeroyl chloride, the exotherm and therewith the complete reaction can be controlled and is suitable for large scale production.

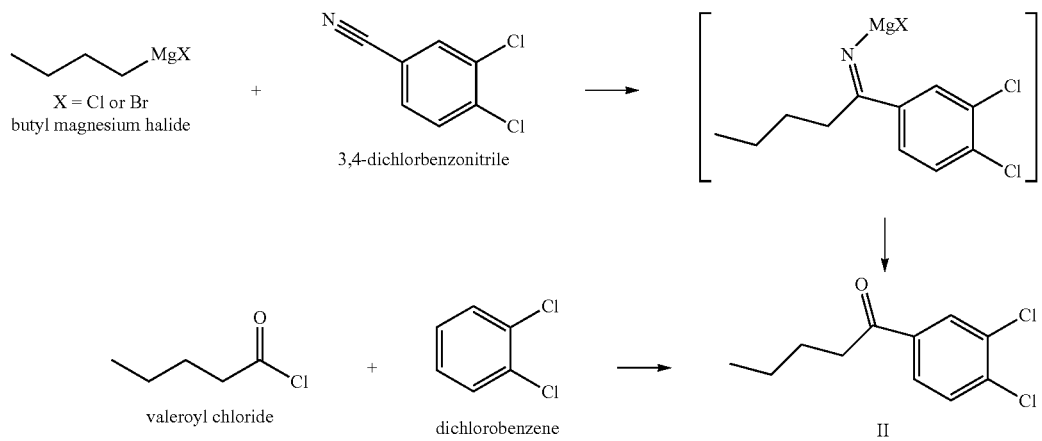

A certain embodiment of the invention is a process as described herein, further comprising methylenation of a compound of formula II to a compound of formula IV

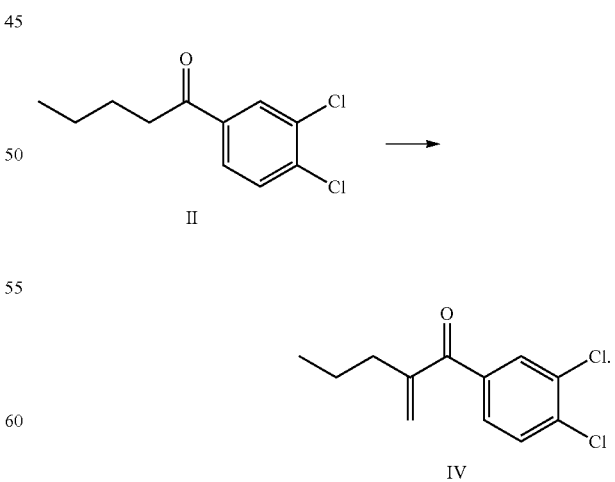

A certain embodiment of the invention is a process as described herein, whereby the compound of formula VIII is resolved by chiral chromatography.

A certain embodiment of the invention is a process as described herein, whereby the compound of formula VIII is resolved by chiral Supercritical Fluid Chromatography.

A certain embodiment of the invention is a process as described herein, whereby the compound of formula VIII is resolved by chiral HPLC.

A certain embodiment of the invention is a process as described herein, whereby the compound of formula VIII is deprotected using 2-ethyl chloroformate.

A certain embodiment of the invention is a process as described herein, whereby the compound of formula VIII is deprotected using 2-ethyl chloroformate in the presence of a tertiary amine like Hünig's base or tripropylamine or triethylamine, in particular Hünig's base or tripropylamine, even more particular, Hünig's base.

A certain embodiment of the invention is a process to synthesize (3,4-Dichloro-phenyl)-((S)-3-propyl-pyrrolidin-3-yl)-methanone hydrochloride of formula I

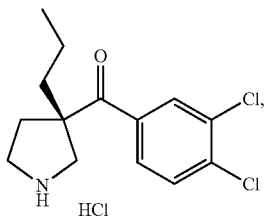

I or a hydrate thereof, consisting of a reaction of a compound of formula IV with a compound of formula VI,

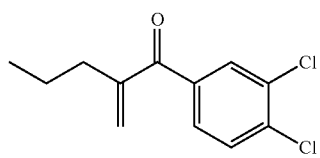

IV

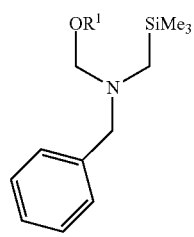

VI with $R^1$=H or $C_{1-4}$-alkyl, to yield a compound of formula VIII,

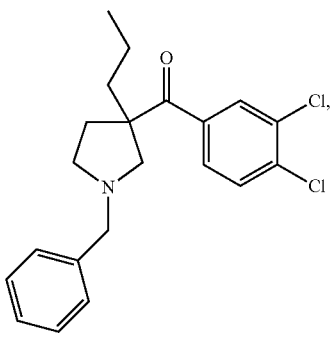

VIII and
a) resolving the compound of formula VIII into its enantiomers followed by the deprotection of a compound of formula IX-1 to a compound of formula I,

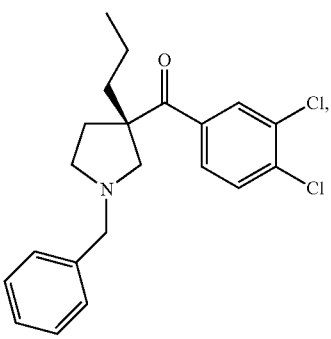

IX-1 or
b) deprotecting the compound of formula VIII to a compound of formula X followed by a chiral resolution to obtain a compound of formula I

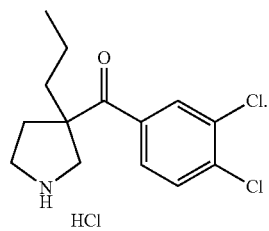

X

A certain embodiment of the invention is a [3+2] cycloaddition of an azomethine ylide to olefin IV to form pyrrolidine VIII, whereby a compound of formula I can be obtained by first resolving pyrrolidine VIII to form pyrrolidine IX-1 followed by deprotection.

A certain embodiment of the invention is a [3+2] cycloaddition of an azomethine ylide to olefin IV to form pyrrolidine VIII, whereby pyrrolidine VIII can be deprotected and the resolved to give compound of formula IA certain embodiment of the invention is a process as described herein, leading to the quarterhydrate of a compound of formula I.

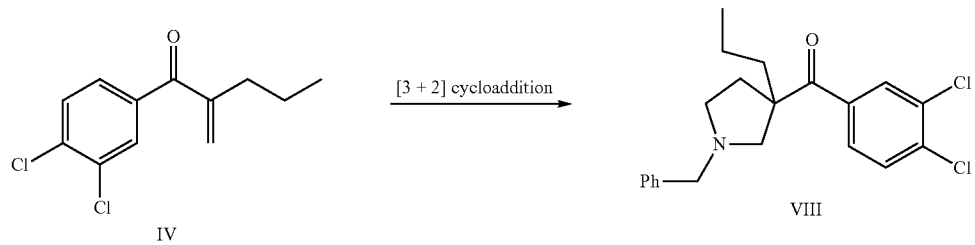

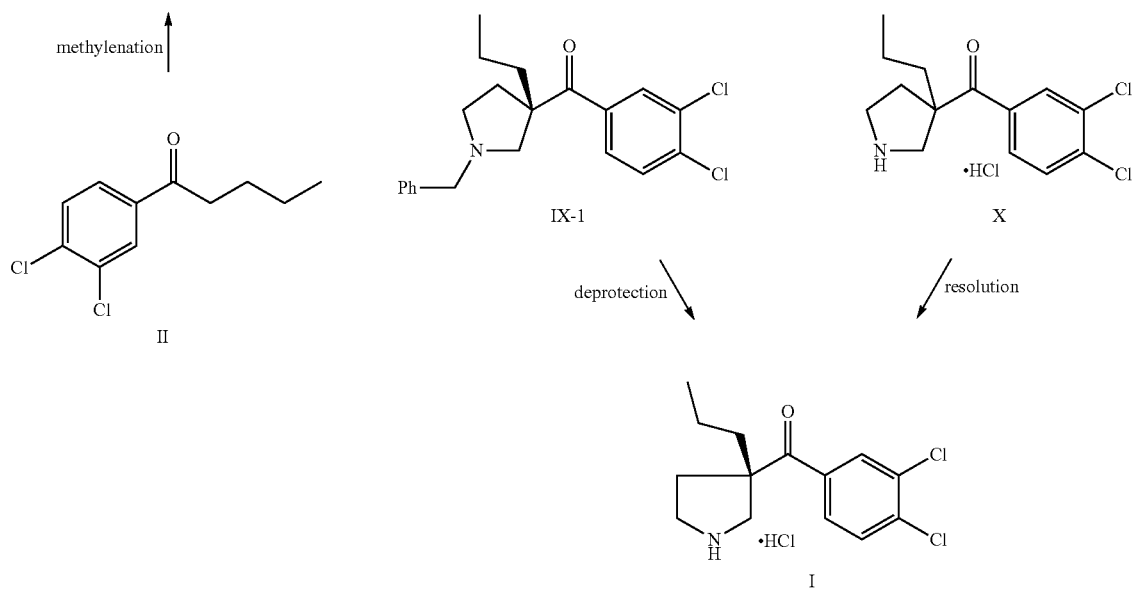

A certain embodiment of the invention is a process as described herein, whereby compound II can be obtained for instance by the addition of a butyl-metal reagent like for example butyl magnesium chloride or butyl magnesium bromide on an electrophile like for instance 3,4-dichlorbenzonitrile.

A certain embodiment of the invention is a process as described herein, whereby in a Friedel-Crafts between valeroyl chloride, valeroyl anhydride or valeroyl acid on dichlorobenzene, in the presence of a suitable catalyst or promoter like aluminum chloride (AlCl₃) a compound of formula I is obtained, whereby the acid chloride is slowly dosed on a mixture of AlCl₃ and dichlorobenzene.

A certain embodiment of the invention is a process as described herein, further consisting of methylenation of a compound of formula II to a compound of formula IV

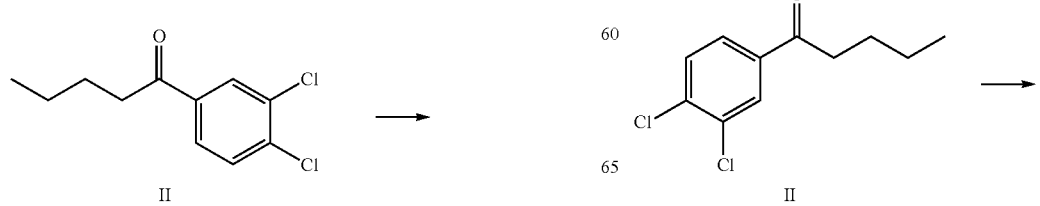

A certain embodiment of the invention is a process as described herein, whereby olefin IV is prepared by methylenation of the compound of formula II via a Mannich reaction and elimination of the β-amino group, whereby the methylenation can be performed with a source of formaldehyde in the presence of a dialkylamine and an acid.

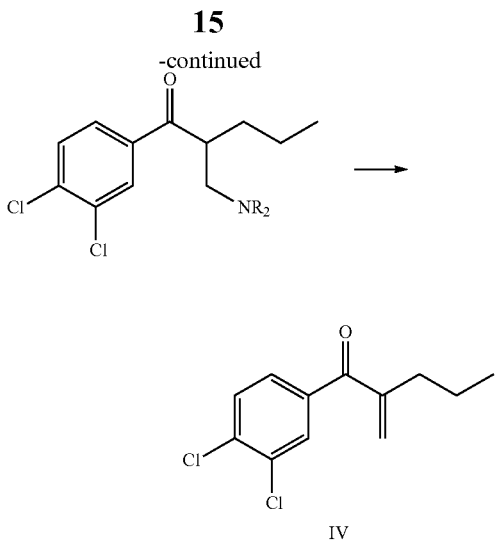

A certain embodiment of the invention is a process as described herein, whereby the methylenation technology involving a dialkylamine (such as diethylamine, morpholine, diisopropylamine, in particular diethylamine and diisopropylamine), a suitable acid (such as acetic acid) and a suitable formaldehyde source (such as paraformaldehyde or aqueous formaldehyde (e.g. >30%) is used to react a compound of formula II to a compound of formula IV. A suitable solvent can be selected from tetrahydrofuran (THF), 2-Methyltetrahydrofuran MeTHF, heptane and toluene, in particular from THF and heptane.

A certain embodiment of the invention is a process as described herein, whereby the [3+2] cycloaddition is performed via an N-benzyl azomethine glide generated from N-benzyl-(trimethylsilyl)amine (Bn-TMSMA) and a formadehyde source or an N-Benzyl-N-(alkoxymethyl)-(trimethylsilyl)amine reagent (Bn-TMSMA-CH₂OR), in the presence of a catalyst.

A certain embodiment of the invention is a process as described herein, whereby N-Benzyl-N-(methoxymethyl)-(trimethylsilyl)amine (Bn-TMSMA-CH₂OMe) is not isolated and the crude solution being introduced in the cycloaddition step.

A certain embodiment of the invention is a process as described herein, whereby Bn-TMSMA-CH₂OH can be generated in-situ by reacting of Bn-TMSMA with a formaldehyde source like aqueous formaldehyde (usually >30% m/m) or in particular paraformaldehyde.

A certain embodiment of the invention is a process as described herein, whereby paraformaldehyde can be depolymerized in-situ and reacted with Bn-TMSMA by using catalytic amount of bases like alkoxides (for example KOtBu) or tetramethylguanidine, in particular tetramethylguanidine.

A certain embodiment of the invention is a process as described herein, whereby Bn-TMSMA-CH₂OH is generated in THF by reacting Bn-TMSMA with paraformaldehyde in the presence of catalytic amount of tetramethyl guanidine, at 20 to 50° C. in particular between room temperature and 40° C. Further, Bn-TMSMA-CH₂OH solution is introduced without isolation into the cycloaddition step and reacted with olefin IV in the presence of a catalyst like TFA, in particular in amounts superior to the amount of the tetramethylguanidine used in the formation of Bn-TMSMA-CH₂OH.

A certain embodiment of the invention is a process as described herein, whereby pyrrolidine VIII can be resolved by chiral SFC or chiral HPLC to provide pyrrolidine IX-1.

A certain embodiment of the invention is a process as described herein, whereby pyrrolidine IX-1 is deprotected by 2-ethylchloroformate to form the corresponding carbamate intermediate in the presence of base like triethylamine or N-ethyldiisopropylamine, in particular N-ethyldiisopropylamine. The resulting carbamate intermediate can then be cleaved by the addition of an alcohol like ethanol or methanol, in particular methanol to form a compound of formula I.

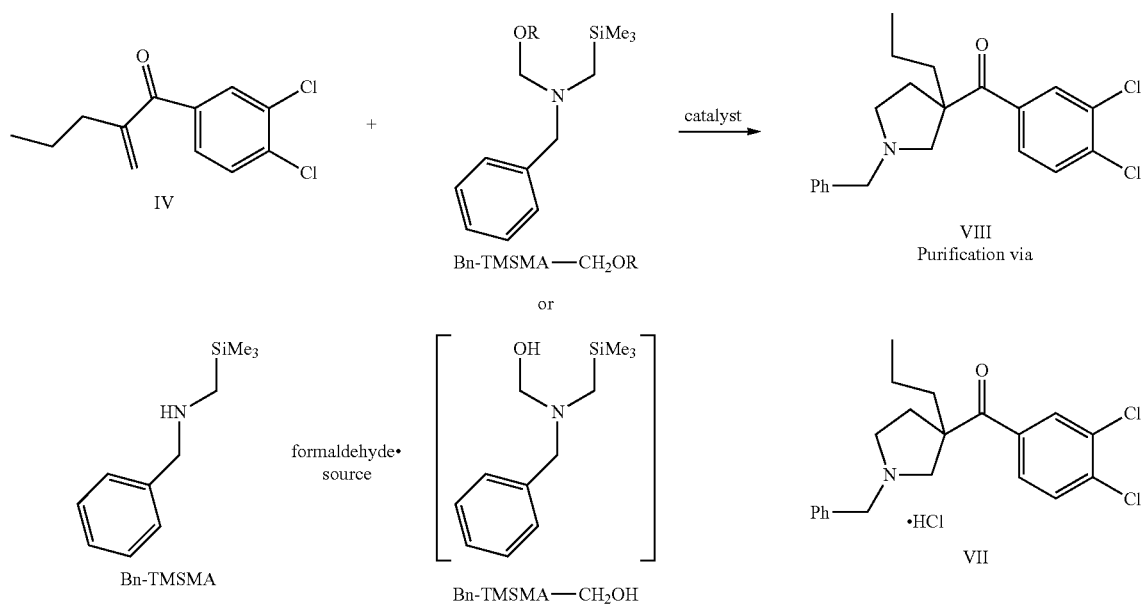

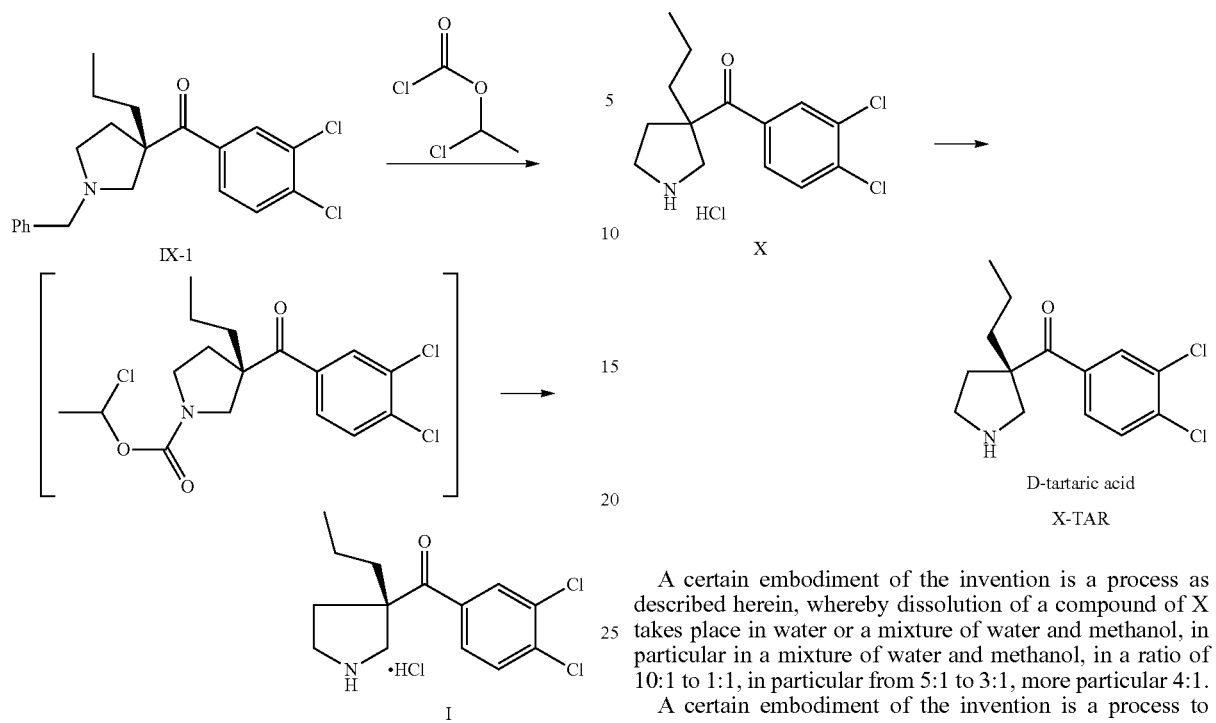

A certain embodiment of the invention is a process as described herein, whereby pyrrolidine VIII can be deprotected to compound of formula X

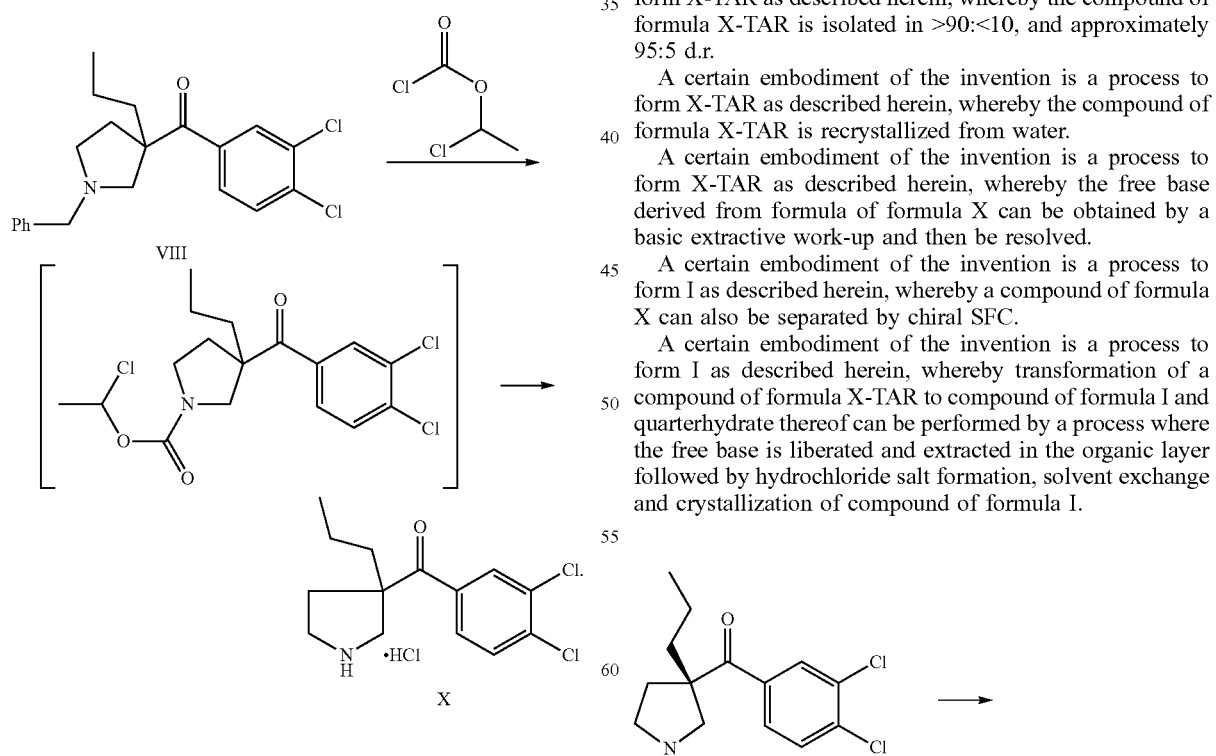

A certain embodiment of the invention is a process as described herein, whereby a compound of formula X can then be resolved via a classical resolution with D-tartaric acid.

A certain embodiment of the invention is a process as described herein, whereby dissolution of a compound of X takes place in water or a mixture of water and methanol, in particular in a mixture of water and methanol, in a ratio of 10:1 to 1:1, in particular from 5:1 to 3:1, more particular 4:1.

A certain embodiment of the invention is a process to form X-TAR as described herein, whereby D-tartaric acid is added between 0.4 and 0.7, in particular between 0.5 and 0.6 equiv., more particular around 0.5 equiv. and sodium hydroxide, in particular in equimolar amount to the D-tartaric acid used is added.

A certain embodiment of the invention is a process to form X-TAR as described herein, whereby the compound of formula X-TAR is isolated in >90:<10, and approximately 95:5 d.r.

A certain embodiment of the invention is a process to form X-TAR as described herein, whereby the compound of formula X-TAR is recrystallized from water.

A certain embodiment of the invention is a process to form X-TAR as described herein, whereby the free base derived from formula of formula X can be obtained by a basic extractive work-up and then be resolved.

A certain embodiment of the invention is a process to form I as described herein, whereby a compound of formula X can also be separated by chiral SFC.

A certain embodiment of the invention is a process to form I as described herein, whereby transformation of a compound of formula X-TAR to compound of formula I and quarterhydrate thereof can be performed by a process where the free base is liberated and extracted in the organic layer followed by hydrochloride salt formation, solvent exchange and crystallization of compound of formula I.

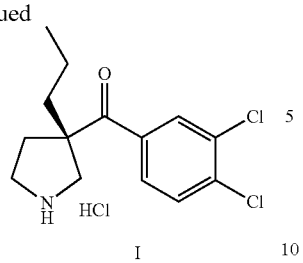

I

A certain embodiment of the invention is a process to form I as described herein, whereby the tartaric acid salt X-TAR is dissolved in water, MTBE is added followed by sodium hydroxide. The free base is extracted in the organic layer. Ethanol is added followed by HCl. The resulting mixture is dried azeotropically with ethanol and polish filtered. The solution is solvent exchanged to ethyl acetate, seeded and treated with wet ethanol leading to the formation of the desired compound of formula I quarterhydrate.

A certain embodiment of the invention is a process to form I as described herein, whereby compound of formula X can be dissolved in ethanol and treated with HCl.

A certain embodiment of the invention is a process to form I as described herein, whereby compound of formula X can be dissolved in ethanol and treated with HCl., whereby the hydrochloride salt is formed but at the same time, the tartaric acid which otherwise is not very soluble in organic solvents is transformed in situ to its corresponding soluble diethyl ester by Fischer esterification. The ethanolic solution is then dried azeotropically, polish filtered and solvent exchanged to ethyl acetate. The solution is seeded and treated with wet ethyl acetate, leading to the formation of the desired compound of formula I quarterhydrate.

A certain embodiment of the invention is a process to form the quarterhydrate of I as described herein, whereby a compound of formula I in the anhydrous form can be transformed into the corresponding quarterhydrate by exposure to a wet atmosphere or by digestion in a water-containing solvent or solvent mixture like for example wet ethyl acetate or a mixture of AcOEt/Ethanol/water.

A certain embodiment of the invention is a process as described herein, whereby the methylenation technology involving diethylamine, acetic acid and paraformaldehyde is used to react a compound of formula II to a compound of formula IV.

A certain embodiment of the invention is a process as described herein, whereby the methylenation technology involves diethylamine, acetic acid and paraformaldehyde is used to react a compound of formula II to a compound of formula IV via intermediate III-1.

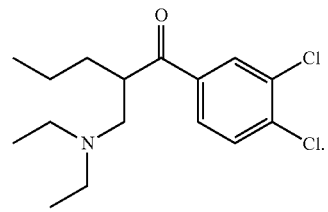

III-1

A certain embodiment of the invention is a process as described herein, whereby the methylenation technology involves diisopropylamine and acetic acid is used to react a compound of formula II to a compound of formula IV.

A certain embodiment of the invention is a process as described herein, whereby the methylenation technology involves diisopropylamine and acetic acid is used to react a compound of formula II to a compound of formula IV via intermediate III-2.

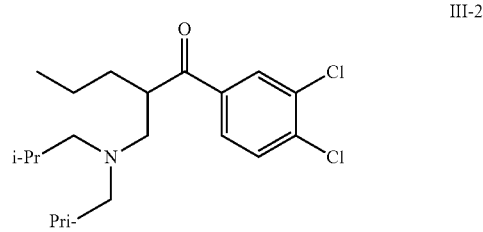

III-2

A certain embodiment of the invention is a process as described herein, whereby the compound of formula VIII is resolved by chiral Supercritical Fluid Chromatography (SFC).

A certain embodiment of the invention is a process as described herein, whereby the compound of formula VIII is resolved by chiral High Performance Liquid Chromatography (HPLC).

A certain embodiment of the invention is a process as described herein, whereby the compound of formula VIII is deprotected using a chloroformate reagent (such as 2-chloroethylchloroformate).

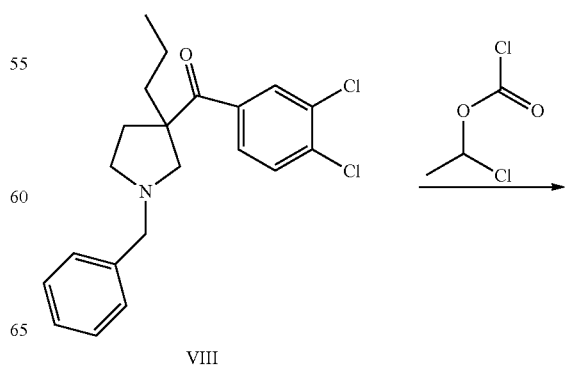

VIII

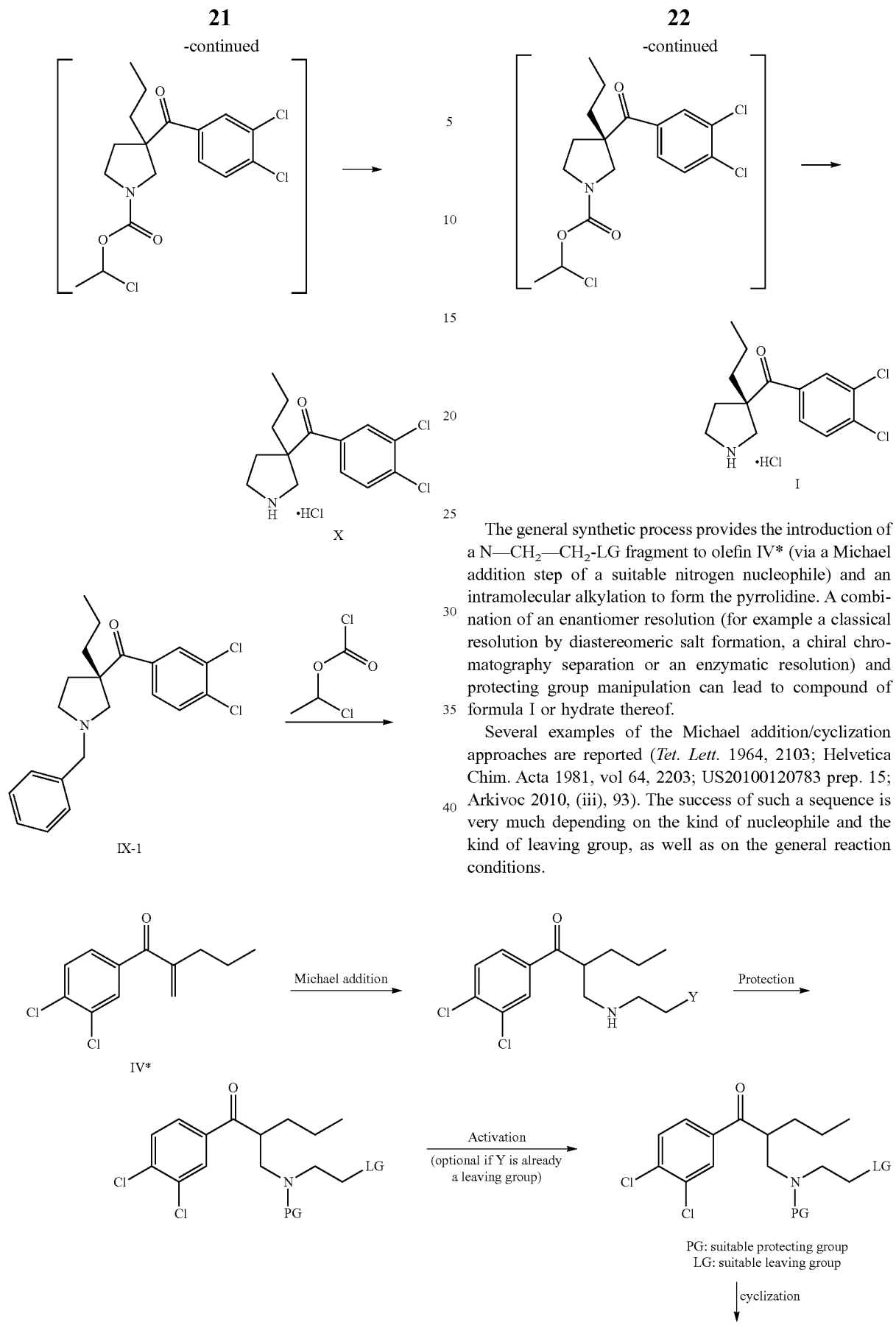

The general synthetic process provides the introduction of a N—CH$_2$—CH$_2$-LG fragment to olefin IV* (via a Michael addition step of a suitable nitrogen nucleophile) and an intramolecular alkylation to form the pyrrolidine. A combination of an enantiomer resolution (for example a classical resolution by diastereomeric salt formation, a chiral chromatography separation or an enzymatic resolution) and protecting group manipulation can lead to compound of formula I or hydrate thereof.

Several examples of the Michael addition/cyclization approaches are reported (*Tet. Lett.* 1964, 2103; *Helvetica Chim. Acta* 1981, vol 64, 2203; US20100120783 prep. 15; *Arkivoc* 2010, (iii), 93). The success of such a sequence is very much depending on the kind of nucleophile and the kind of leaving group, as well as on the general reaction conditions.

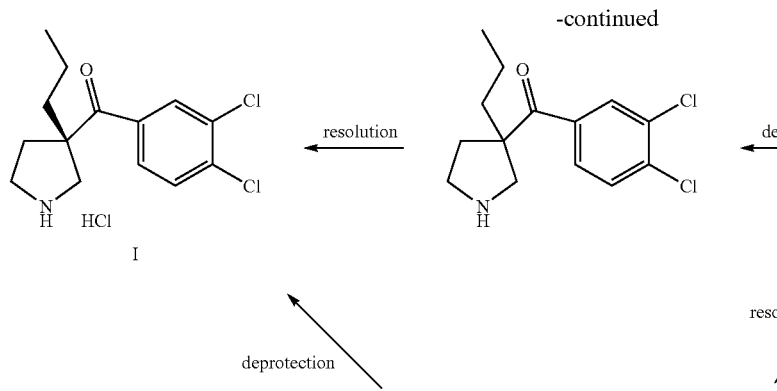

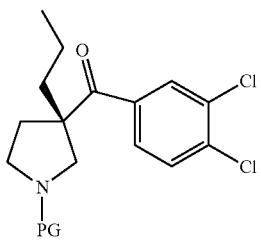

Suitable protecting groups (PG) are acyl groups like e.g. acetyl or benzoyl), benzyloxycarbonyl (Cbz) or Boc, in particular the Boc group.

Suitable substituent Y is OH or chloro, in particular OH.

Suitable leaving groups (LG) are for example (but not limited to) chloride, bromide, iodide, mesylate (OMs), tosylate (OTs), benzenesulfonate ($C_6H_5SO_3$), (o, m or p)-nitrobenzenesulfonate ($O_2NC_6H_4SO_3$) and triflate ($OSO_2CF_3$). Depending on its nature, LG can also be part of the N—$CH_2$—$CH_2$—Y fragment, for example when LG=Cl. Boc-N—$CH_2$—$CH_2$-LG fragments are known to exhibit instability and to decompose to the corresponding oxazolidinones (for leading references see: *Tetrathedron* 2001, 270).

Fragments like LG=OMs are reported to be instable (WO2010042445 p 75-76 compound 74). A certain embodiment of the invention is that these fragments can be used efficiently and exhibited sufficient reactivity for the intramolecular cyclization under the right conditions. The mesylate can easily be prepared from the corresponding alcohol intermediate which can be obtained by the Michael addition of ethanolamine to olefin IV* followed by Boc-protection.

A certain embodiment of the invention is that the olefin IV* is prepared by methylenation of the known compound of formula II* via a Mannich reaction and elimination of the β-amino group. The methylenation can be performed with a source of formaldehyde in the presence of a dialkylamine (like e.g. diethylamine) and an acid (like e.g. acetic acid).

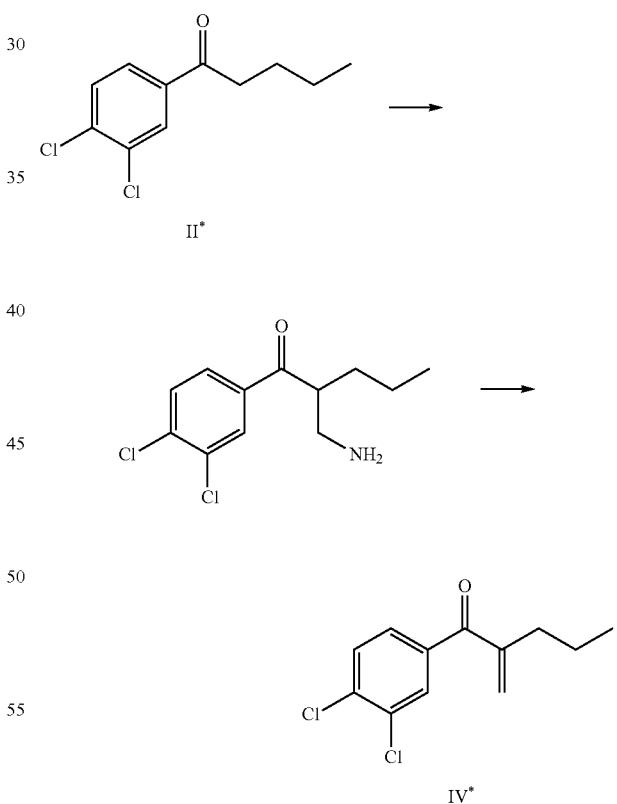

The compound of formula II* can be prepared by addition of a Grignard reagent (like BuMgBr) to 3,4-dichlorobenzonitrile (*J. Med. Chem.* 2006, 49, 1420-1432; WO2010121022). Compound of formula II* can also be prepared via Friedel-Crafts reaction on 1,2-dichlorobenzene (DE2809022).

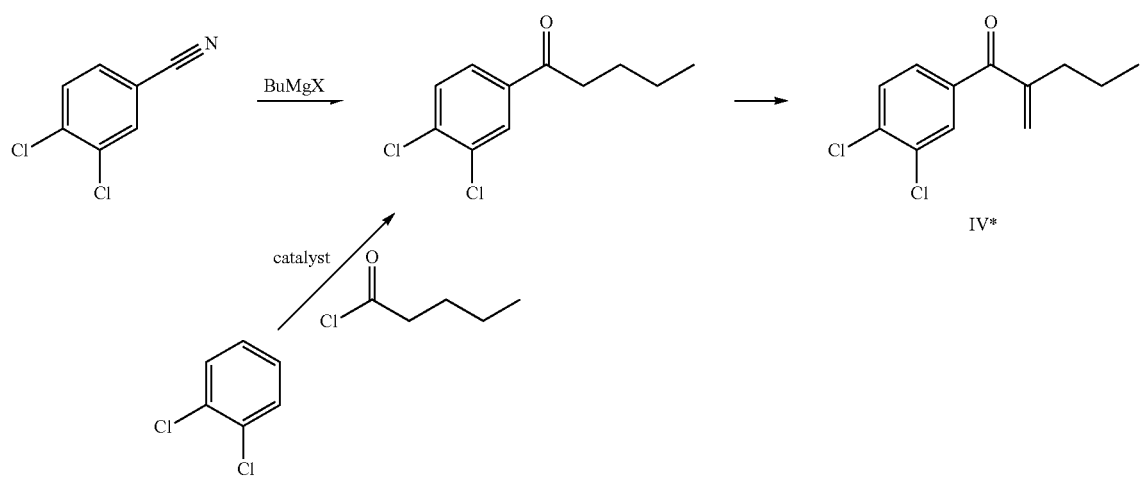

A certain embodiment of the invention is that the Friedel-Crafts route offers the advantage of using very cheap starting materials. The reference process (DE2809022) is not suitable for large scale production, as valeroyl chloride is added to a room temperature mixture of $AlCl_3$ and 1,2-dichlorobenzene upon which a significant exotherm occurs and upon further heating, the reaction appears to start in an uncontrolled manner.

A certain embodiment of the invention is that when firstly charging $AlC_3$ and 1,2-dichlorobenzene and heated the mixture to 60-100° C., in particular between 70-90° C. more particular to 80° C.±1° C., and secondly slowly adding valeroyl chloride, the exotherm and therewith the complete reaction can be controlled and is suitable for large scale production.

A certain embodiment of the invention is that the aza-Michael addition of ethanolamine to olefin IV to form compound of formula V can be performed without a catalyst when working in solvents like THF at high concentrations. A double Michael adduct can be controlled under 10 a % by HPLC (210 nm). The Michael addition is performed between 15 and 70° C., in particular between 20 and 40° C., more particular at 25° C.±1° C.

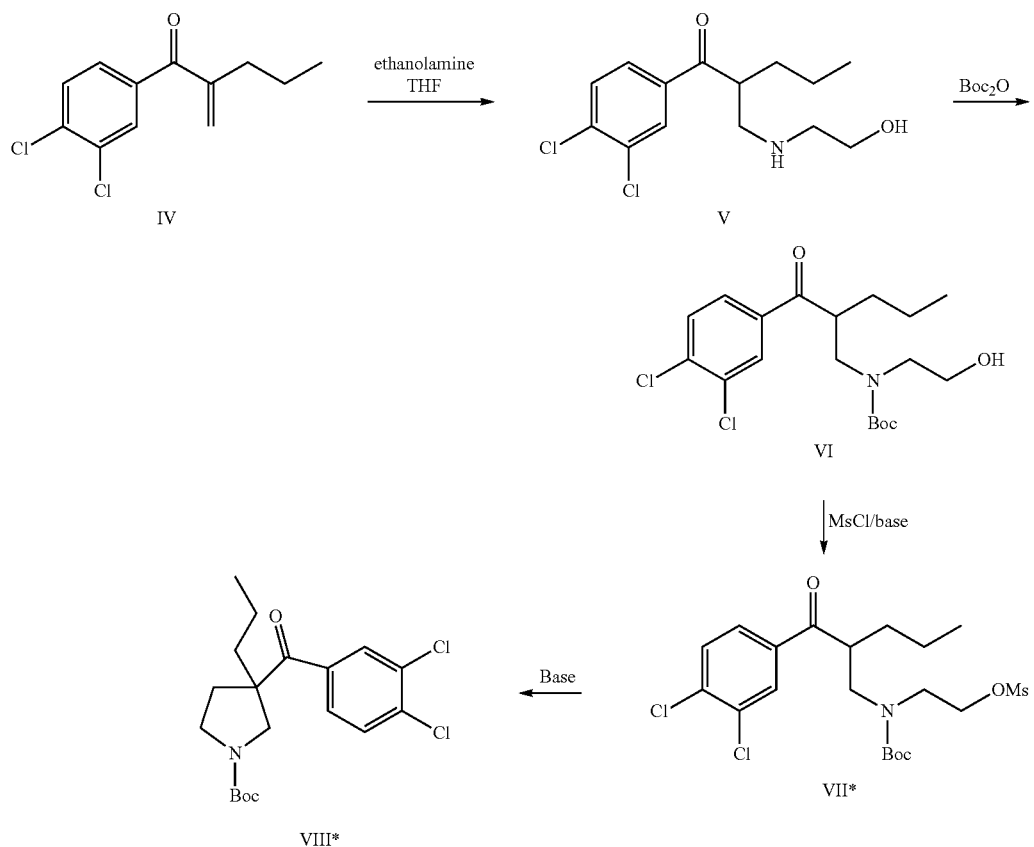

A certain embodiment of the invention is that the Boc protection of compound of formula V* can be performed under standard conditions with Di-t-butyl dicarbonate (Boc₂O) and leads to a compound of formula VI*. The mesylation of a compound of formula VI* can be performed with MsCl in the presence of a base like for example a trialkylamine base (like e.g. Et₃N, diisopropylethylamine or tripropylamine) and leads to compound of formula VII*.

A certain embodiment of the invention is that the cyclization step (compound of formula VII* to compound of formula VIII*) can be performed by but not limited to alkoxyde bases (like e.g. sodium t-amylate), either in THF, toluene or toluene/THF mixtures, or under biphasic conditions by using hydroxide bases (like e.g. NaOH) in combination with a phase transfer catalyst like a quaternary ammonium salt like a tetrabutylammonium halide salt, for example tetrabutylammonium bromide or Aliquat 336, in particular tetrabutylammonium bromide. Surprisingly we found that the cyclization did form the O-alkylation isomer VIII*' as by-product (between 5-15a % by GC):

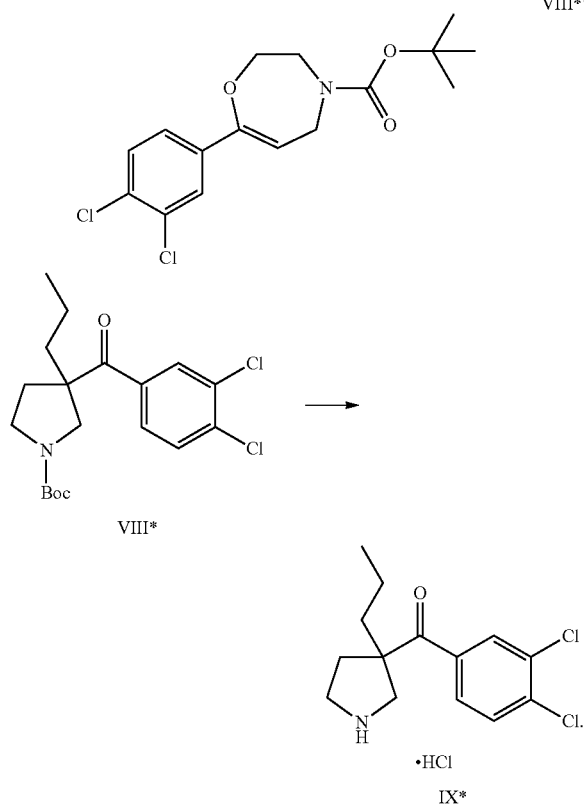

A certain embodiment of the invention is that the purification effect at the stage of hydrochloride IX* (after Boc deprotection of crude VIII*) has been found to be surprisingly high, allowing the isolation of >95% pure hydrochloride IX*, starting from 75-80% m/m pure VIII*. Under the Boc-deprotection, the O-alkylation isomer is hydrolyzed back to compound V*. The Boc-deprotection is performed in toluene in the presence of HCl, at 40 to 110° C., in particular between 50 and 80° C., more particular at 60° C.±1° C. The compound of formula VIII* can be added to a mixture of toluene and HCl in order to control the reaction (heat and gas release). After completion of the reaction, the reaction mixture can be dried azeotropically and the product is crystallized.

A certain embodiment of the invention is that the process for the transformation of compound IV* to compound VIII* can be optimized by introducing the intermediates in the following step without purification.

A certain embodiment of the invention is that it was surprisingly found that the Michael addition, the Boc protection and the cyclization steps can be performed in a fully telescoped one-pot-process without any extractive work-up in between the steps. This greatly increased the overall efficiency of the synthesis.

A certain embodiment of the invention is the classical resolution of compound of formula IX* is performed with D-tartaric acid.

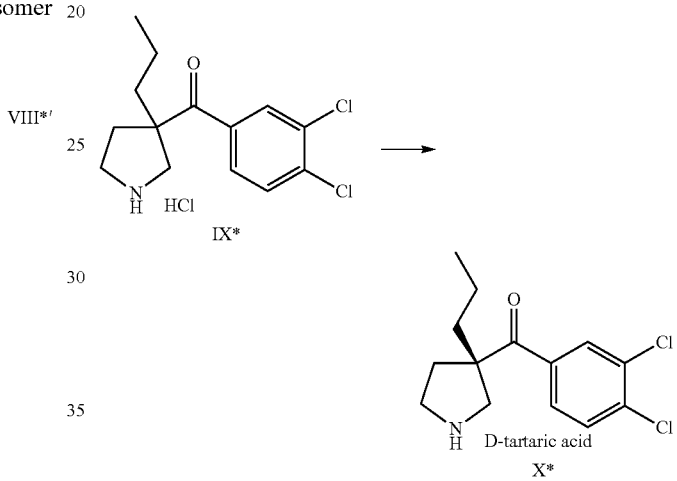

This process involves the dissolution of compound of IX* in water or a mixture of water and methanol, in particular in a mixture of water and methanol in a ratio of 10:1 to 1:1, in particular from 5:1 to 3:1, more particular 4:1. D-tartaric acid is added between 0.4 and 0.7, in particular between 0.5 and 0.6 equiv., more particular 0.5 equiv. Sodium hydroxide (in particular in equimolar amount to the D-tartaric acid) is added, partially neutralizing the hydrochloride salt and allowing for the formation of the desired tartaric acid salt of formula X* from the free base of compound of formula IX*. Compound of formula X* can then be isolated in >90:<10, and around ca 95:5 d.r. We surprisingly found that the diastereomeric purity can be improved to >99% by recrystallization from water. Salts X* of d.r. of 88:12 can even be upgraded to ca 99:1 d.r. upon this recrystallization. The process is very efficient and avoids unnecessary extractive work-up and solvent exchange.

A certain embodiment of the invention is that the free base derived from formula of formula IX* can be obtained by a basic extractive work-up and then be resolved.

A certain embodiment of the invention is the transformation of compound of formula X* to compound of formula I and quarterhydrate thereof can be performed by liberating the free base and extracting into the organic layer followed by hydrochloride salt formation, solvent exchange and crystallization of compound of formula I.

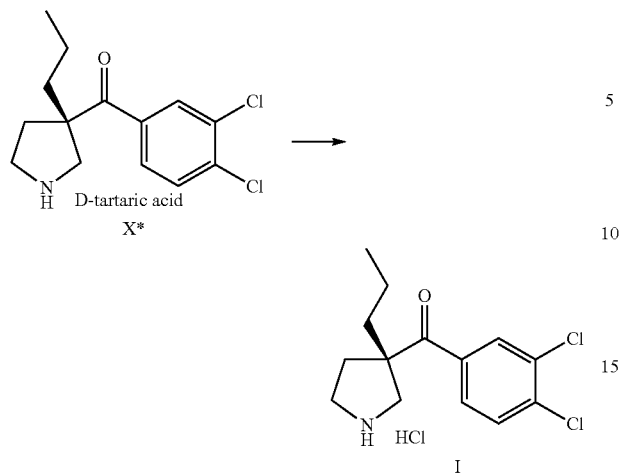

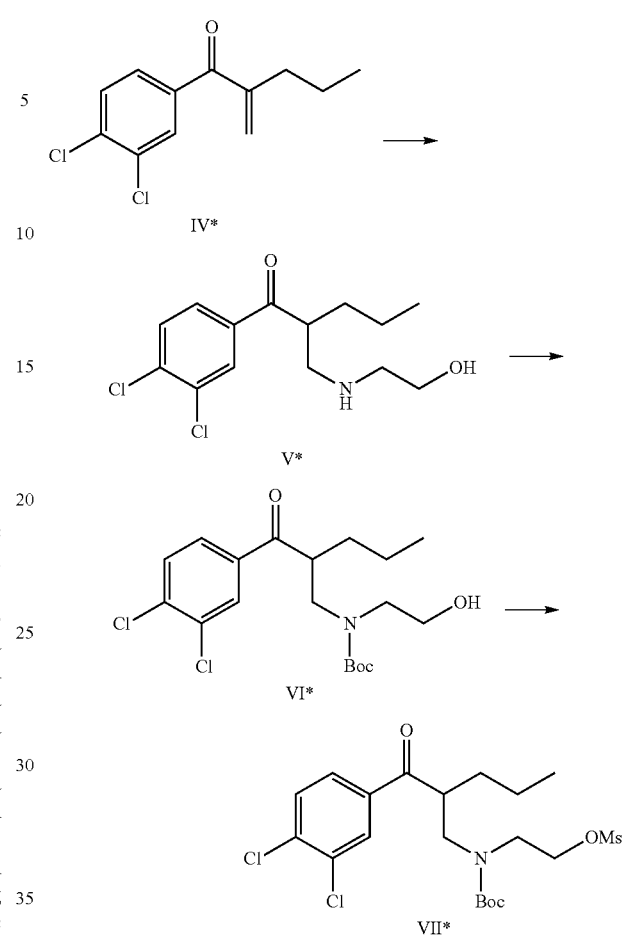

A certain embodiment of the invention is that the tartaric acid salt X* can be dissolved in water. Methyl-tert-butyl ether (MTBE) can be added followed by sodium hydroxide. The free base is extracted into the organic layer. Ethanol is added followed by HCl. The resulting mixture is dried azeotropically with ethanol and polish filtered. The solution is solvent exchanged to ethyl acetate, seeded and treated with wet ethanol leading to the formation of the desired compound of formula I quarterhydrate.

A certain embodiment of the invention is that a compound of formula X* can be dissolved in ethanol and treated with HCl. The hydrochloride salt is formed but at the same time, the tartaric acid which otherwise is not very soluble in organic solvents, is transformed in situ to its corresponding soluble diethyl ester by Fischer esterification. The ethanolic solution is then dried azeotropically, polish filtered and solvent exchanged to ethyl acetate. The solution is seeded and treated with wet ethyl acetate, leading to the formation of the desired compound of formula I as quarterhydrate.

A certain embodiment of the invention is that a compound of formula I in the anhydrous form can be transformed into the corresponding quarterhydrate by exposure to a wet atmosphere or by digestion in a water-containing solvent or solvent mixture like for example wet ethyl acetate or a mixture of AcOEt/Ethanol/water. In the right solvent mixture only small amount of water (even slightly over the theoretical amount) are required to effect the transformation.

A certain embodiment of the invention is a process as described herein to synthesize (3,4-Dichloro-phenyl)-((S)-3-propyl-pyrrolidin-3-yl)-methanone hydrochloride of formula I

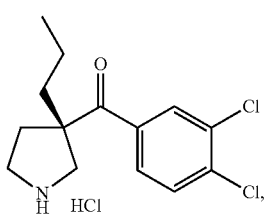

or a hydrate thereof, comprising reaction of a compound of formula IV* via a compound of formula V* to a compound of formula VI* and further to a compound of formula VII*,

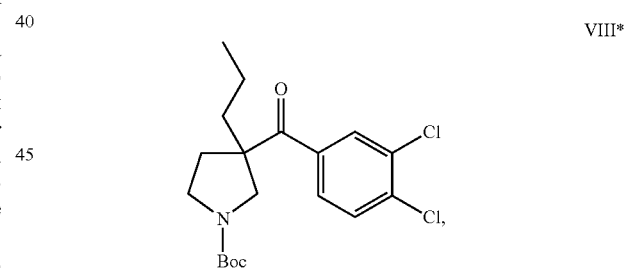

to yield a compound of formula VIII*,

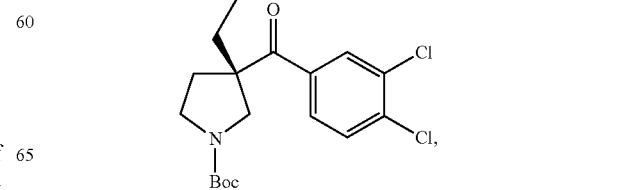

and a) resolving the compound of formula VIII* into its enantiomers to a compound of formula VIII*-1 followed by its deprotection to a compound of formula I, b) deprotecting the compound of formula VIII* to a compound of formula IX* followed by a classical resolution to obtain a compound of formula X* and salt exchange to a compound of formula I

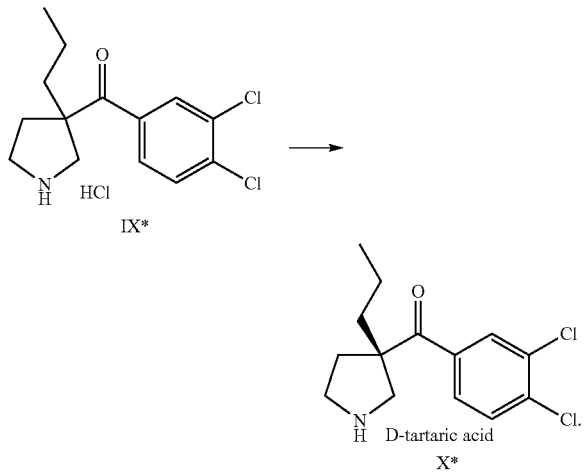

IX*

A certain embodiment of the invention is a process as described herein, whereby an intermediate of formula V* is formed as by-product

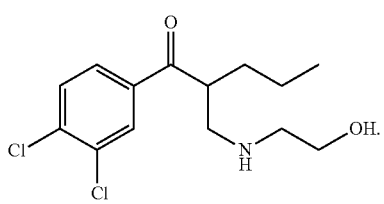

V*

A certain embodiment of the invention is a process as described herein, whereby 1%±0.9% of an intermediate of formula V* is formed as by-product.

A certain embodiment of the invention is a process as described herein, whereby 1% of an intermediate of formula V* is formed as by-product.

A certain embodiment of the invention is a process as described herein to synthesize (3,4-Dichloro-phenyl)-((S)-3-propyl-pyrrolidin-3-yl)-methanone hydrochloride of formula I,

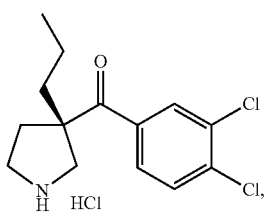

I or a hydrate thereof, in particular the quarterhydrate, comprising reaction of a compound of formula IV* via a compound of formula V* to a compound of formula VI* and further to a compound of formula VII*,

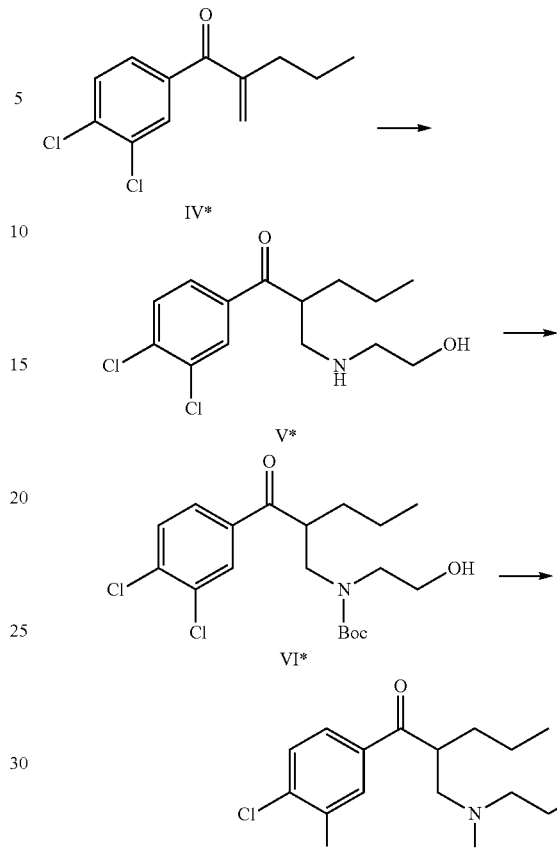

to yield a compound of formula VIII*,

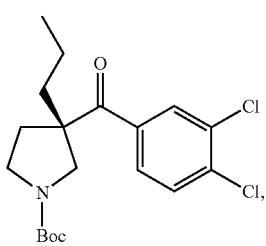

and
a) resolving the compound of formula VIII* into its enantiomers to a compound of formula VIII*-1 followed by its deprotection to a compound of formula I,

VIII*-1 or
b) deprotecting the compound of formula VIII* to a compound of formula IX* followed by a classical resolution to obtain a compound of formula X* and salt exchange to a compound of formula I

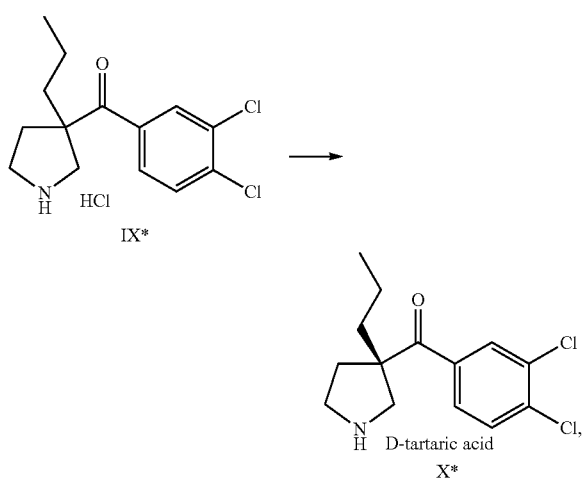

IX*

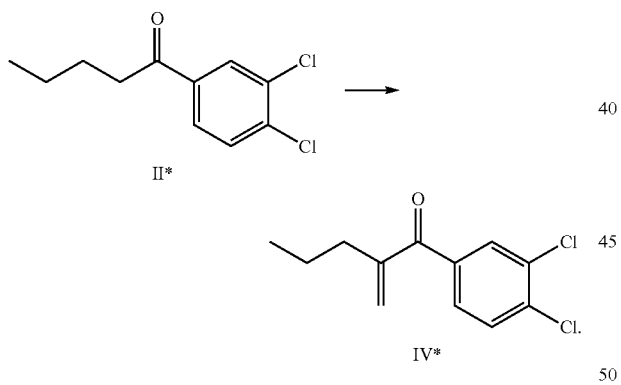

X* or c) deprotecting the compound of formula VIII* to a compound of formula IX* (or its corresponding free base) followed by an enantiomer separation by chiral chromatography to a compound of formula I.

A certain embodiment of the invention is a process as described herein, leading to the quarterhydrate of a compound of formula I.

A certain embodiment of the invention is a process as described herein, further comprising methylenation of a compound of formula II* to a compound of formula IV*

II*

IV*

A certain embodiment of the invention is a process as described herein to synthesize (3,4-Dichloro-phenyl)-((S)-3-propyl-pyrrolidin-3-yl)-methanone hydrochloride of formula I

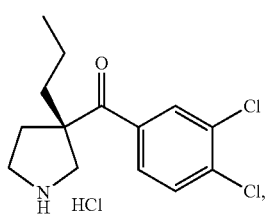

I or a hydrate thereof, consisting of reaction of a compound of formula IV* via a compound of formula V* to a compound of formula VI* and further to a compound of formula VII*,

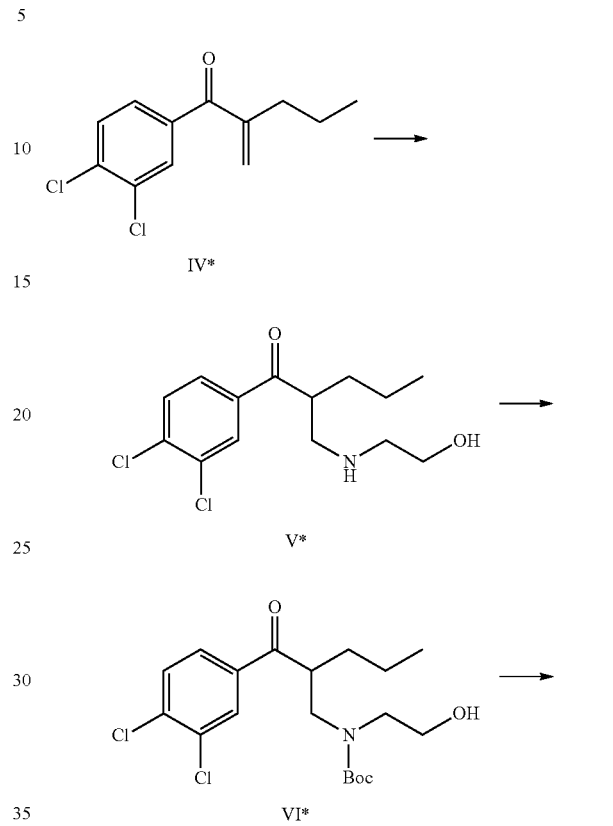

IV*

V*

VI*

VII* to yield a compound of formula VIII*,

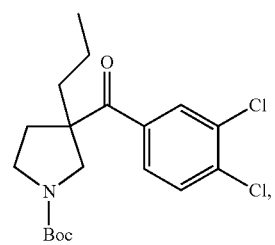

VIII* and a) resolving the compound of formula VIII* into its enantiomers to a compound of formula VIII*-1 followed by its deprotection to a compound of formula I,

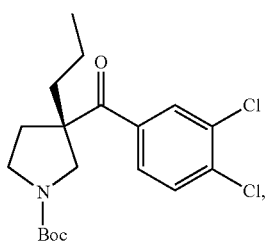

VIII*-1 or b) deprotecting the compound of formula VIII* to a compound of formula IX* followed by a classical resolution to obtain a compound of formula X* and salt exchange to a compound of formula I

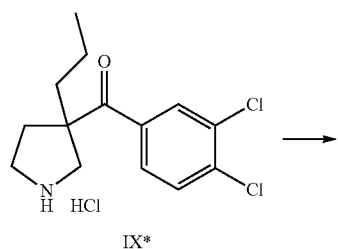

IX*

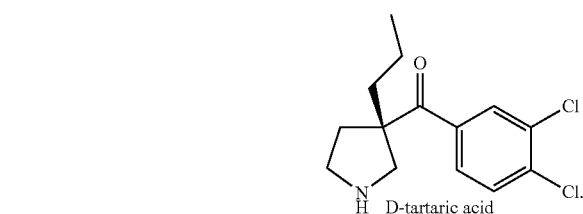

X*

A certain embodiment of the invention is a process as described herein, further consisting of methylenation of a compound of formula II* to a compound of formula IV*

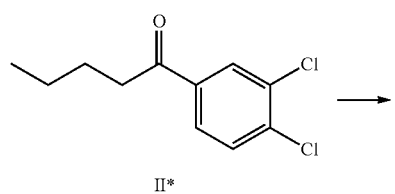

II*

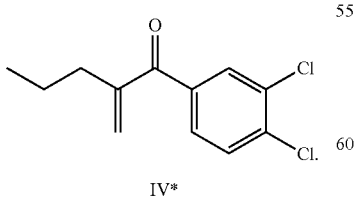

IV*

A certain embodiment of the invention is a process as described herein, further comprising methylenation of a compound of formula II* to a compound of formula IV*

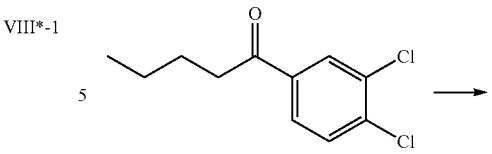

II*

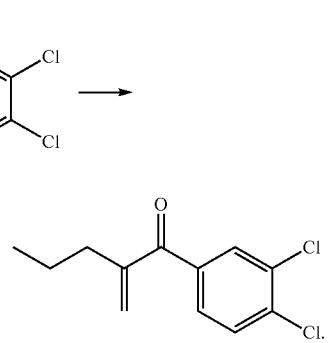

IV*

A certain embodiment of the invention is a process as described herein to synthesize (3,4-Dichloro-phenyl)-((S)-3-propyl-pyrrolidin-3-yl)-methanone hydrochloride of formula I

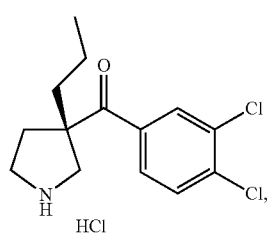

I or a hydrate thereof, consisting of reaction of a compound of formula IV* via a compound of formula V* to a compound of formula VI* and further to a compound of formula VII*,

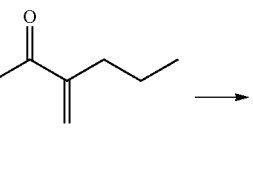

IV*

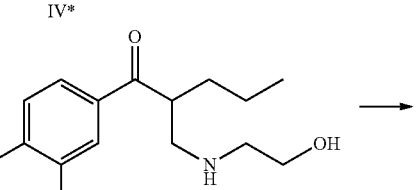

V*

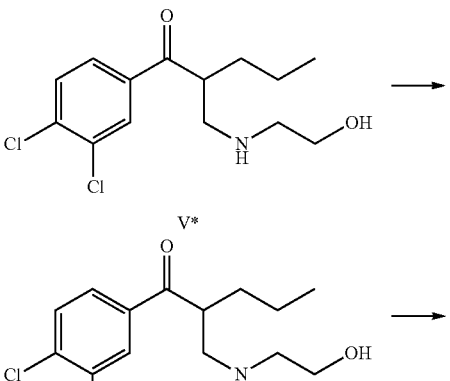

VI*

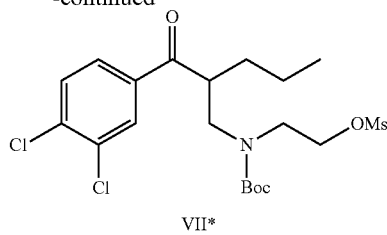

VII* to yield a compound of formula VIII*,

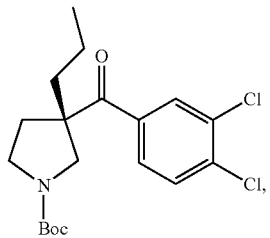

VIII* and resolving the compound of formula VIII* into its enantiomers to a compound of formula VIII*-1 followed by its deprotection to a compound of formula I,

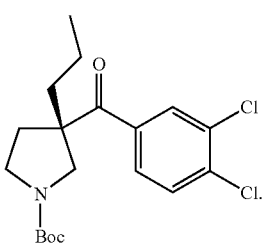

VIII-1

A certain embodiment of the invention is a process as described herein, further comprising methylenation of a compound of formula II* to a compound of formula IV*

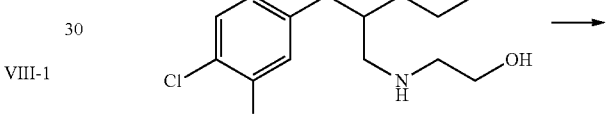

II*

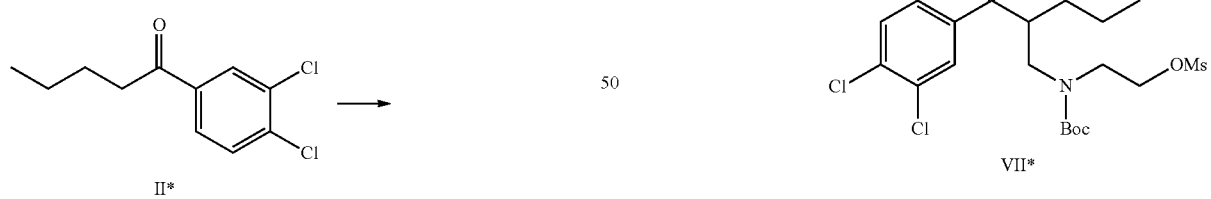

IV*

A certain embodiment of the invention is a process as described herein to synthesize (3,4-Dichloro-phenyl)-((S)-3-propyl-pyrrolidin-3-yl)-methanone hydrochloride of formula I

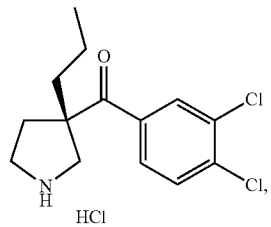

I or a hydrate thereof, consisting of reaction of a compound of formula IV* via a compound of formula V* to a compound of formula VI* and further to a compound of formula VII*,

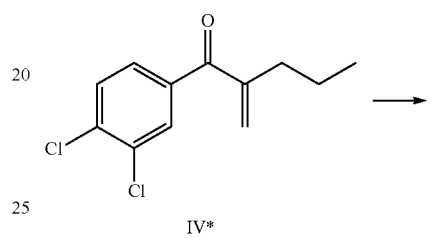

IV*

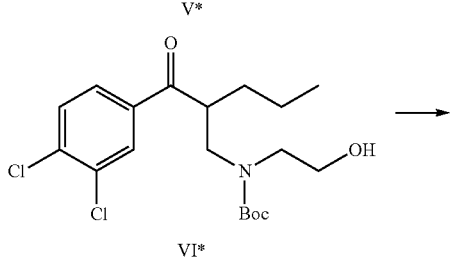

V*

VI*

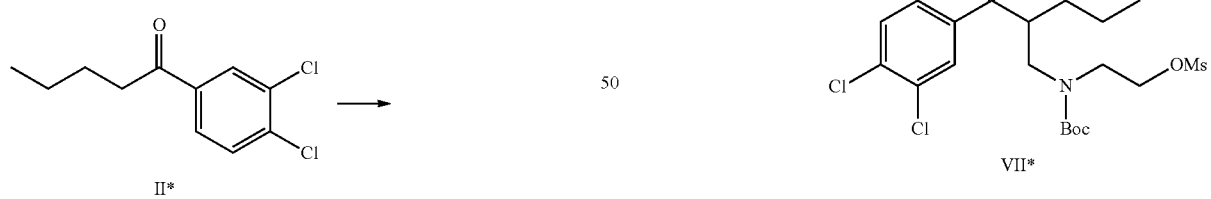

VII* to yield a compound of formula VIII*,

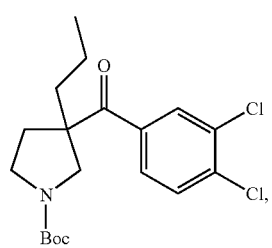

VIII* and deprotecting the compound of formula VIII* to a compound of formula IX* followed by a classical resolution to obtain a compound of formula X* and salt exchange to a compound of formula I

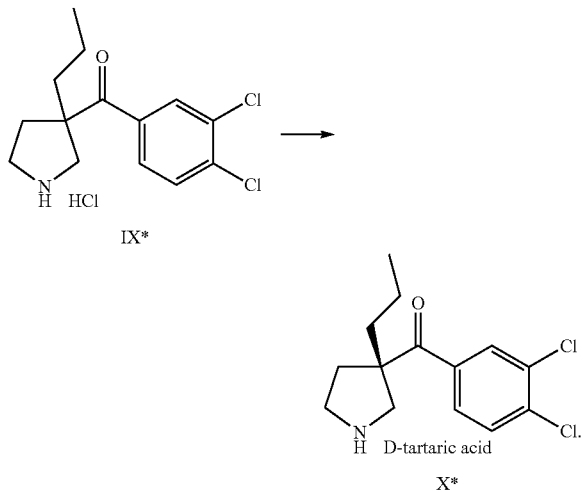

A certain embodiment of the invention is the reaction of a compound of formula IV* via a compound of formula V* to a compound of formula VI* further to a compound of formula VII* and then to a compound of formula VIII* in a telescoped process, where all intermediates could be introduced in the next step without extractive work-up.

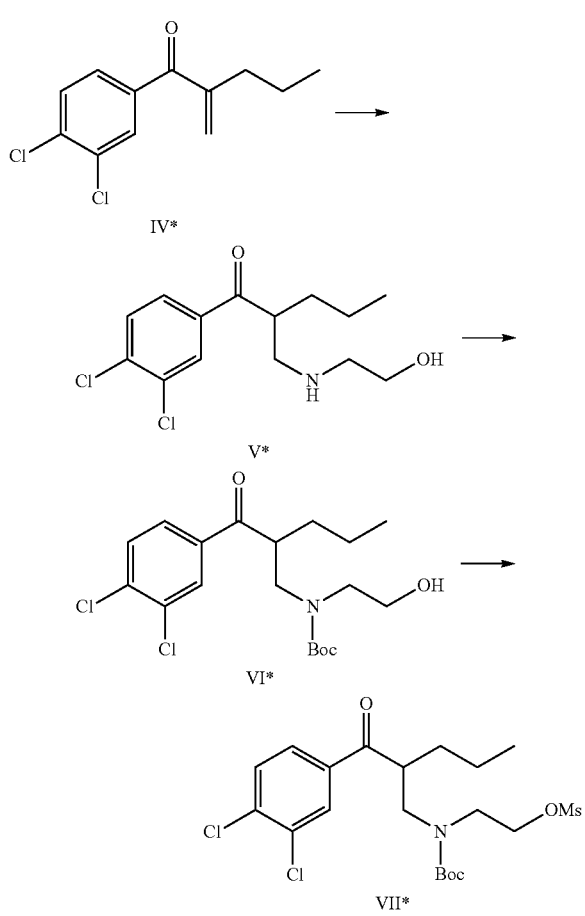

A certain embodiment of the invention is that the aza-Michael addition could be performed without the need of catalysts when working in solvents like THF at high concentration. The Boc protection is performed under standard conditions. For the N-protection, acylic protection groups (for example but not limited to, acetyl, benzoyl, trifluoroacetyl, in particular acetyl) can be suitable for the cyclization.

The purification effect at the stage of hydrochloride IX* (after Boc deprotection of crude VIII*) is surprisingly high, allowing the isolation of >95% hydrochloride IX*, starting from 75-80% m/m pure VIII*. Under the Boc-deprotection, the O-alkylation isomer is hydrolyzed back to compound V*.

A certain embodiment of the invention is that the cyclization step can be performed by using alkoxyde bases (like e.g. sodium t-amylate) in THF, toluene or toluene/THF mixtures, or under biphasic conditions by using hydroxide bases (like e.g. NaOH) in combination with a phase transfer catalyst (for example a quaternary ammonium salt like e.g. tetrabutylammonium bromide). It was however surprisingly found that the cyclization did not only produce the expected pyrrolidine VIII*, but also an O-alkylation isomer VIII*' (between 5-15a % by GC depending on the conditions):

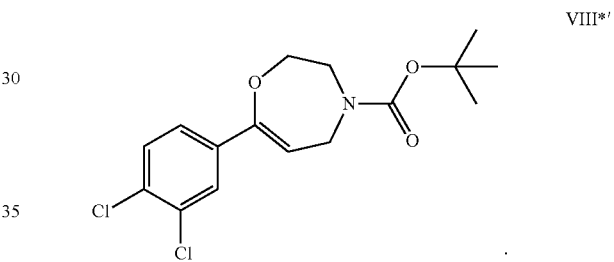

A certain embodiment of the invention is a process as described herein, whereby the methylenation technology involving a dialkylamine, a suitable acid and a formaldehyde source is used to react to a compound of formula II* to a compound of formula IV*.

A certain embodiment of the invention is a process as described herein, whereby the methylenation technology involving diethylamine, acetic acid and paraformaldehyde is used to react a compound of formula II* to a compound of formula IV*.

A certain embodiment of the invention is a process as described herein, whereby the methylenation technology involves diethylamine, acetic acid and paraformaldehyde is used to react a compound of formula II* to a compound of formula IV* via intermediate III*-1.

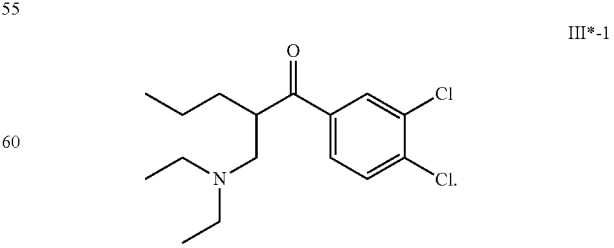

A certain embodiment of the invention is a process as described herein, whereby the methylenation technology involves diisopropylamine and acetic acid is used to react a compound of formula II* to a compound of formula IV*.

A certain embodiment of the invention is a process as described herein, whereby the methylenation technology involves diisopropylamine and acetic acid is used to react a compound of formula II* to a compound of formula IV* via intermediate III*-2.

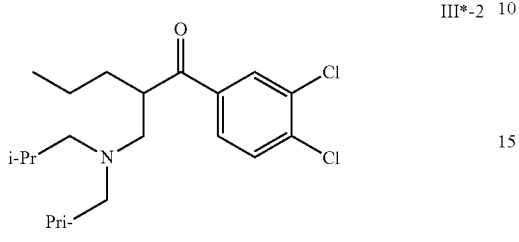

III*-2

A certain embodiment of the invention is a process as described herein, whereby the compound of formula VIII* is resolved by chiral Supercritical Fluid Chromatography.

A certain embodiment of the invention is a process, whereby the compound of formula VIII* is resolved by chiral chromatography.

A certain embodiment of the invention is a process as described herein, whereby the compound of formula VIII* is resolved by chiral high performance liquid chromatography (HPLC).

A certain embodiment of the invention is a process as described herein, whereby the compound of formula VIII* is deprotected using hydrochloric acid.

A certain embodiment of the invention is an intermediate of formula X*

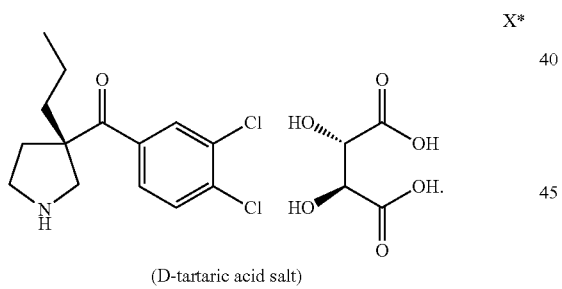

X*

(D-tartaric acid salt)

A certain embodiment of the invention is an intermediate of formula IV*

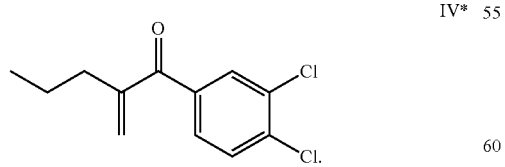

IV*

A certain embodiment of the invention is a process for the preparation of a compound of formula I as described herein, which process comprises one or more of the following steps, whereby R is $C_{1-6}$-alkyl like methyl, ethyl isopropyl, or is benzyl, in particular R is methyl and ethyl:

a) conversion of a compound of formula 12 to the corresponding compound of formula 13

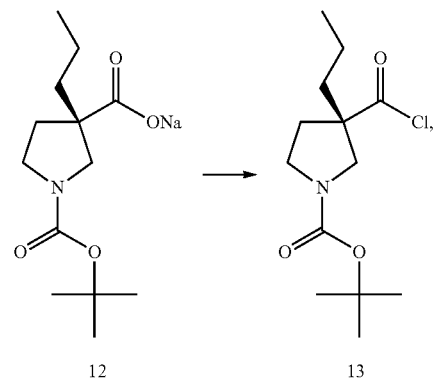

12      13 b) conversion the acyl chloride of formula 13 to a compound of formula 14

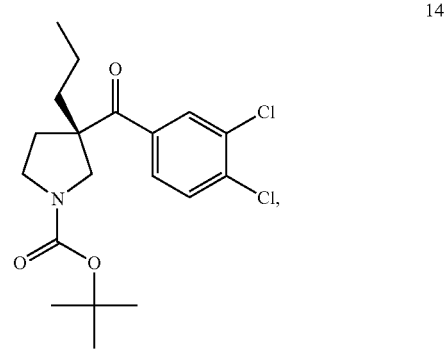 [SMILES: CCC[C@]1(C(=O)c2ccc(Cl)c(Cl)c2)CCN(C(=O)OC(C)(C)C)C1]

14 c) deprotection of a compound of formula 14 to its corresponding compound of formula I, and

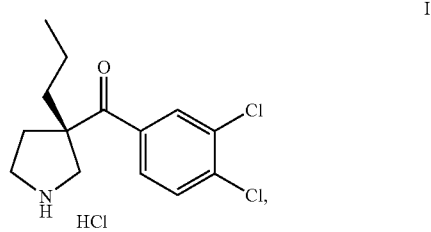 [SMILES: CCC[C@]1(C(=O)c2ccc(Cl)c(Cl)c2)CCNC1 ; Cl]

I d) subsequent isolation of a compound of formula I or its quarterhydrate.

A certain embodiment of the invention is a process for the preparation of a compound of formula I as described herein, which process comprises the following steps a) conversion of a compound of formula 12 to the corresponding compound of formula 13

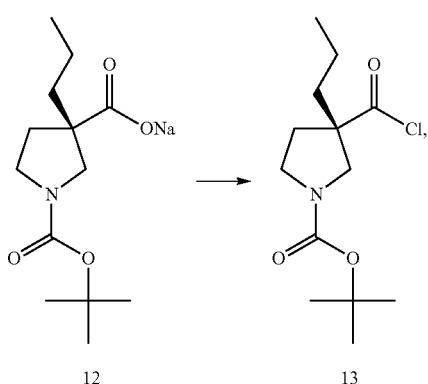

12 → 13 b) conversion the acyl chloride of formula 13 to a compound of formula 14

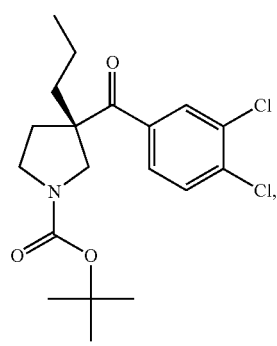

14 c) deprotection of a compound of formula 14 to its corresponding compound of formula I, and

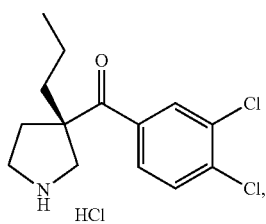

I d) subsequent isolation of a compound of formula I or its quarterhydrate.

A certain embodiment of the invention is a process, wherein a compound of formula 12 is replaced by a compound of formula 12a or by a compound of formula 12b.

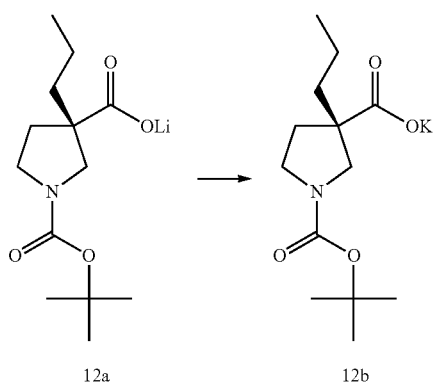

12a    12b

A certain embodiment of the invention is a process, wherein a compound of formula 12 is prepared from a compound of formula 9, comprising one or more of the following steps a) hydrolysis of a compound of formula 9 to a compound of formula 10

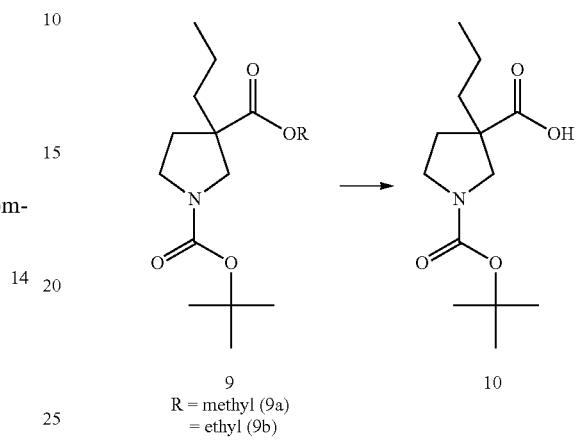

9         10
R = methyl (9a)
  = ethyl (9b)

b) resolution of a compound of formula 10 to the salt of formula 11

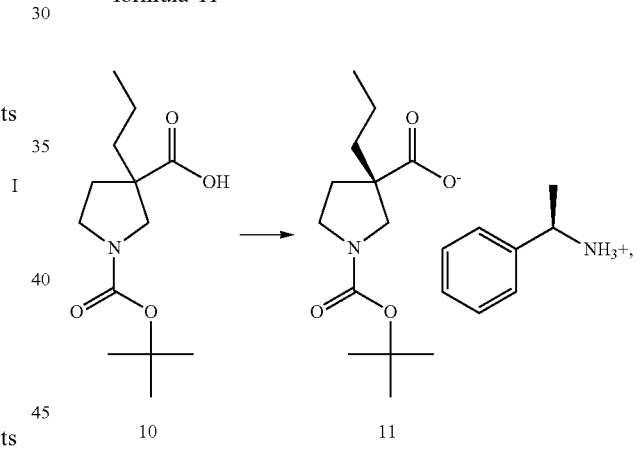

10         11 c) conversion of a compound of formula 11 to the corresponding sodium salt of formula 12

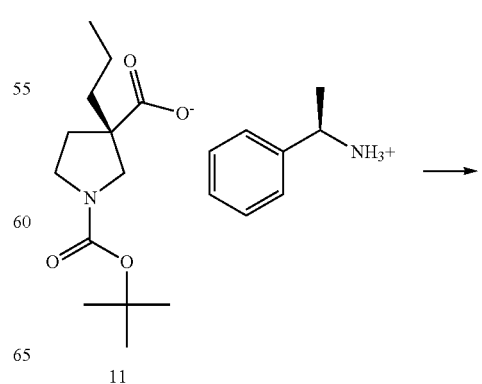

11

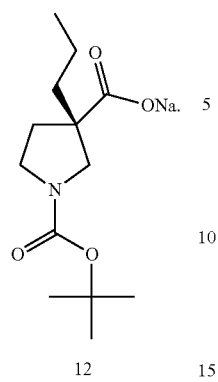

12

A certain embodiment of the invention is a process, wherein a conversion of a compound of formula 11 to the corresponding salt of formula 12, 12a or 12b is formed via acid of formula 10 followed by deprotonation with an appropriate base.

A certain embodiment of the invention is a process, wherein a compound of formula 12 is prepared from a compound of formula 9, comprising the following steps a) hydrolysis of a compound of formula 9 to a compound of formula 10

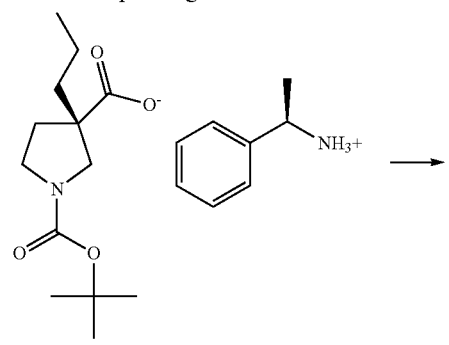

R = methyl (9a)
= ethyl (9b)

9

10 b) resolution of a compound of formula 10 to the salt of formula 11

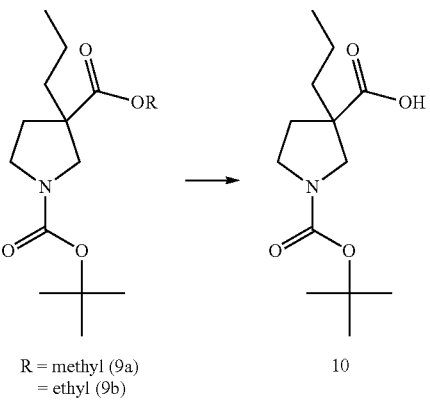

10

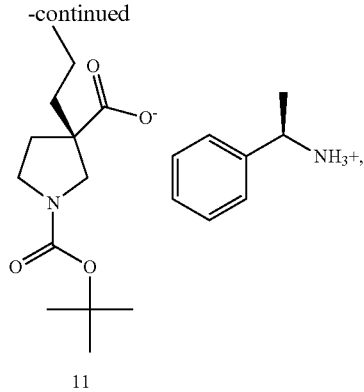

11 d) conversion of a compound of formula 11 to the corresponding sodium salt of formula 12

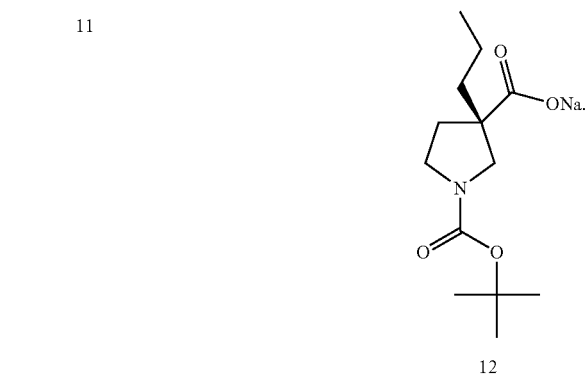

11

12

A certain embodiment of the invention is a process as described herein, wherein a compound of formula 9 is prepared from a compound of formula 7, comprising one or more of the following steps a) debenzylation of a compound of formula 7 to a compound of formula 8

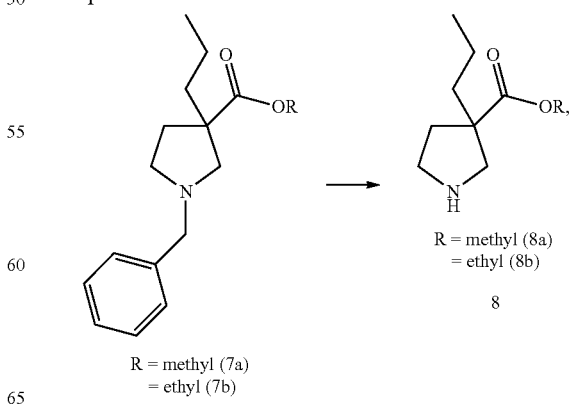

R = methyl (7a)
= ethyl (7b)

7

R = methyl (8a)
= ethyl (8b)

8 b) BOC protection of a compound of formula 8 to result in a compound of formula 9

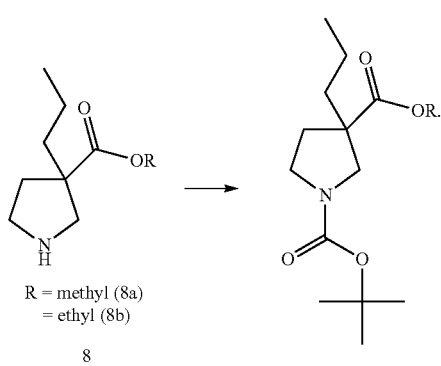

a) debenzylation of a compound of formula 7 to a compound of formula 8

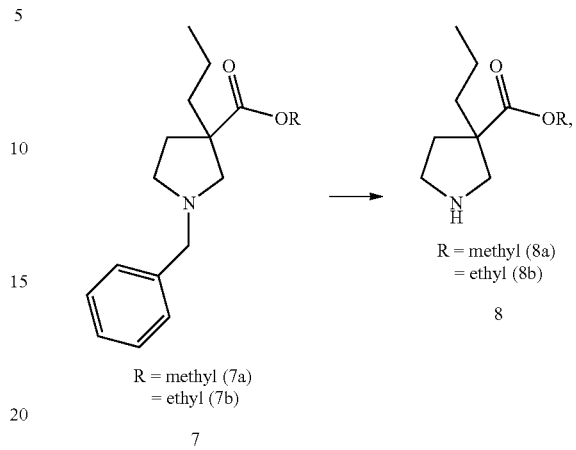

A certain embodiment of the invention is conversion of a compound of formula 11 to the corresponding sodium salt of formula 12 b) BOC protection of a compound of formula 8 to result in a compound of formula 9

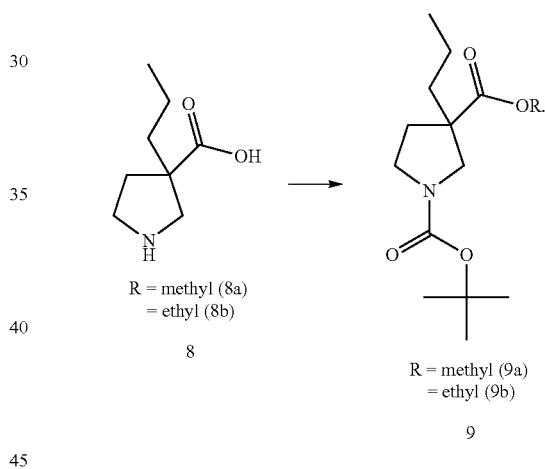

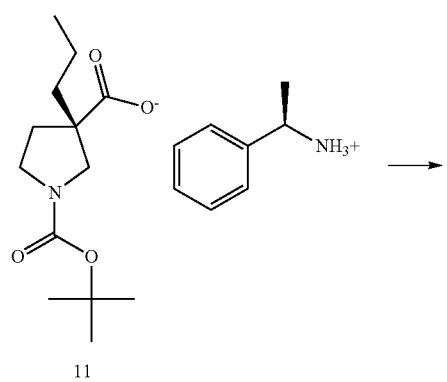

A certain embodiment of the invention is a process as described herein, wherein a compound of formula 7b or 21 is prepared from a compound of formula 2, comprising one or more of the following steps a) reacting a compound of formula 2 to a compound of formula 3

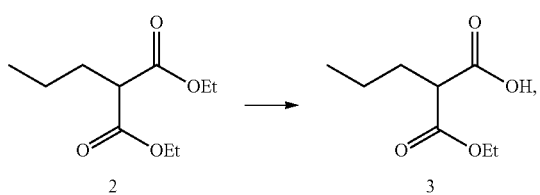

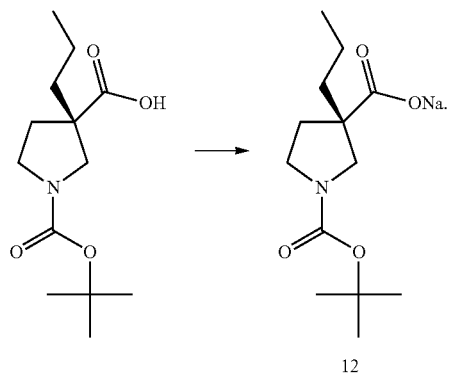

A certain embodiment of the invention is a process as described herein, wherein a compound of formula 9 is prepared from a compound of formula 7, comprising the following steps b) methylenation of a compound of formula 3 to a compound of formula 4

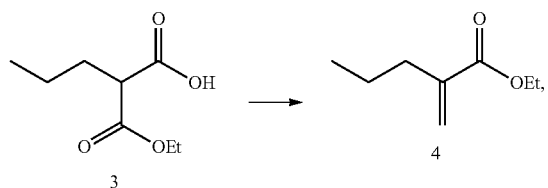

c) reacting a compound of formula 5 to a compound of formula 6

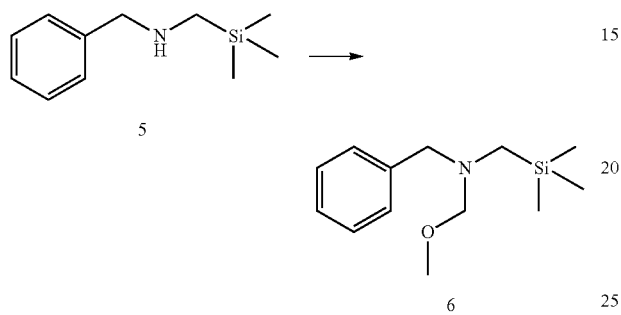

d-1) reacting a compound of formula 6 with a compound of formula 4 to a compound of formula 7b

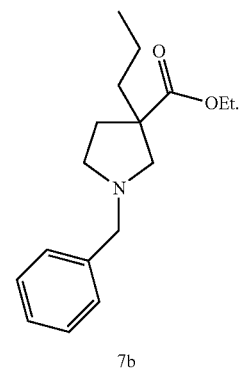

or
d-1) reacting a compound of formula 6 with methyl acrylate to a compound of formula 21

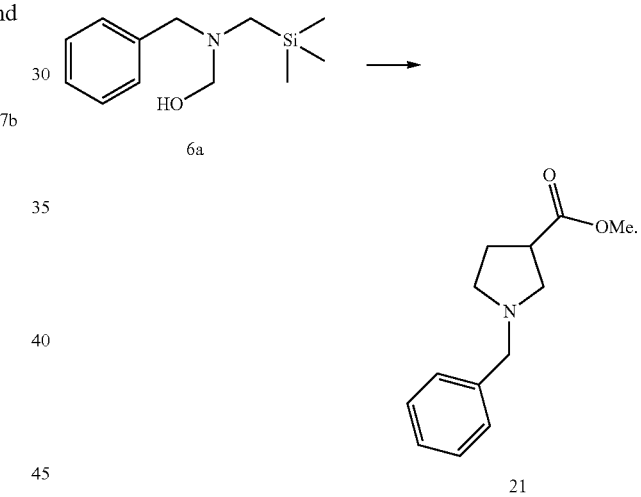

A certain embodiment of the invention is a process as described herein, wherein a compound of formula 6a reacts with a compound of formula 4 to a compound of formula 7b A certain embodiment of the invention is a process as described herein, wherein a compound of formula 6a reacts with methyl acrylate to a compound of formula 21

A certain embodiment of the invention is a process as described herein, wherein a compound of formula 7b or 21 is prepared from a compound of formula 2, comprising the following steps a) reacting a compound of formula 2 to a compound of formula 3

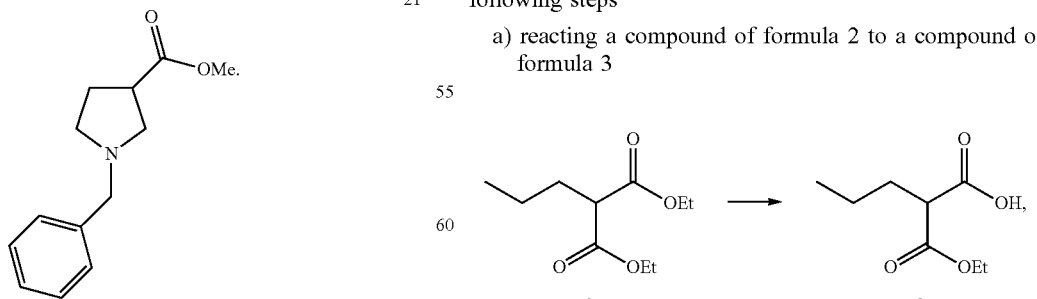

b) methylenation of a compound of formula 3 to a compound of formula 4

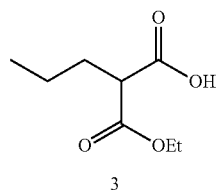
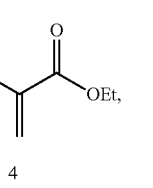
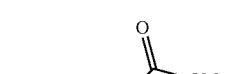

a) reacting a compound of formula 21 to a compound of formula 22,

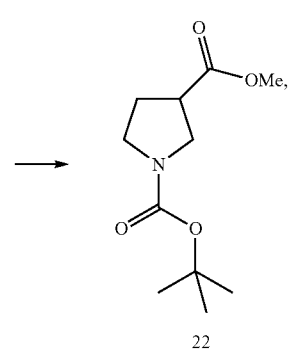

c) reacting a compound of formula 5 to a compound of formula 6

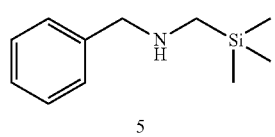

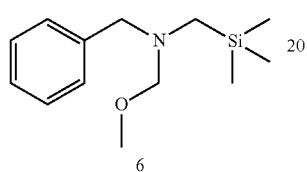

b) reacting a compound of formula 22 to a compound of formula 9a

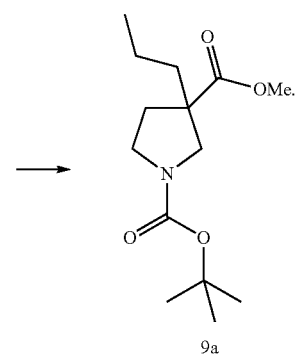

d-1) reacting a compound of formula 6 with a compound of formula 4 to a compound of formula 7b

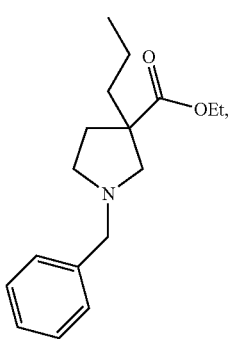

A certain embodiment of the invention is reacting a compound of formula 21 to a compound of formula 22

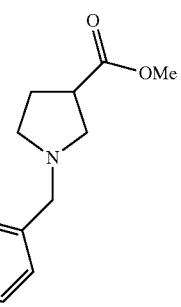

or d-1) reacting a compound of formula 6 with methyl acrylate to a compound of formula 21

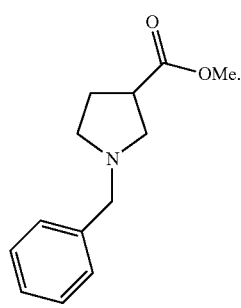

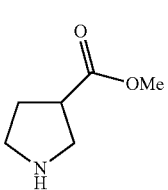
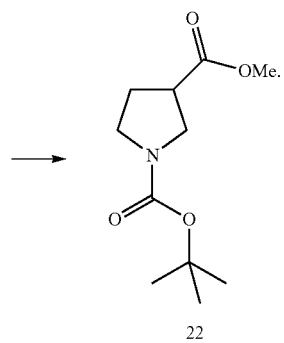

A certain embodiment of the invention is a process as described herein, wherein a compound of formula 9a is prepared from a compound of formula 21, comprising one or more of the following steps A certain embodiment of the invention is a process as described herein, wherein a compound of formula 9a is prepared from a compound of formula 21, comprising the following steps a) reacting a compound of formula 21 to a compound of formula 22,

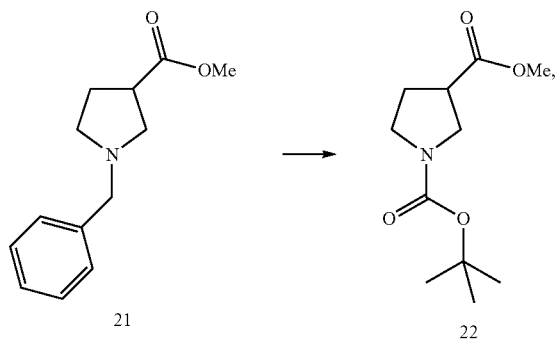 [SMILES: COC(=O)C1CCN(Cc2ccccc2)C1 ; COC(=O)C1CCN(C(=O)OC(C)(C)C)C1]

b) reacting a compound of formula 22 to a compound of formula 9a,

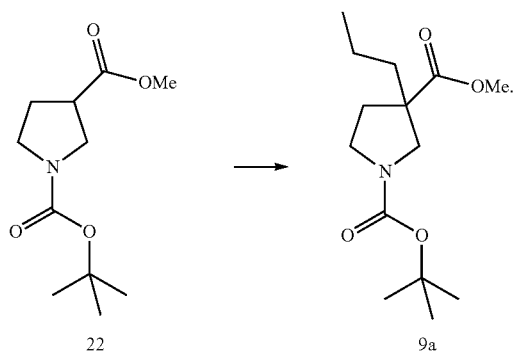 [SMILES: COC(=O)C1CCN(C(=O)OC(C)(C)C)C1 ; CCCC1(C(=O)OC)CCN(C(=O)OC(C)(C)C)C1]

A certain embodiment of the invention is a process as described herein, wherein a compound of formula 12 is prepared from a compound of formula 15, comprising one or more of the following steps a) reacting a compound of formula 15 to a compound of formula 16

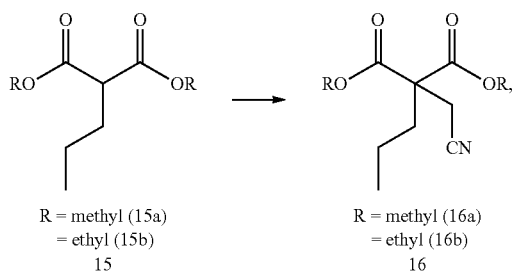

b) desymmetrization of a compound of formula 16 to a compound of formula 17

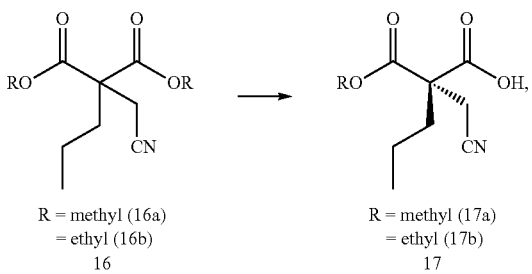

c) reducing a compound of formula 17 to a compound of formula 18

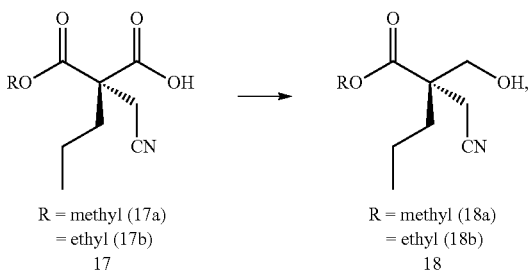

d) reacting a compound of formula 18 to a compound of formula 20

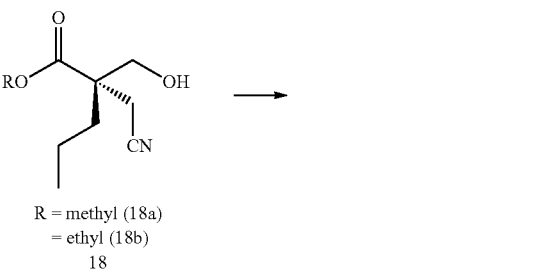

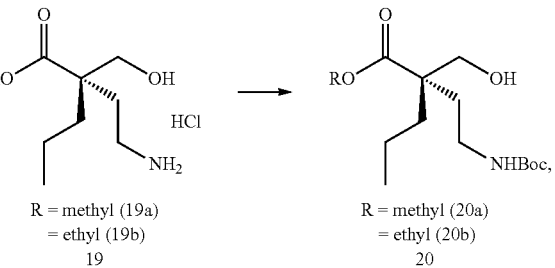

e) reacting a compound of formula 20 to a compound of formula formula 9x

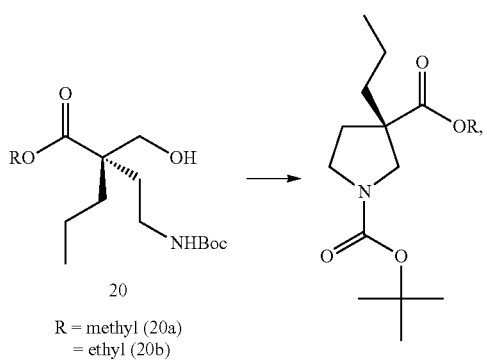

f) conversion of a compound of formula 9x to the corresponding sodium salt of formula 12

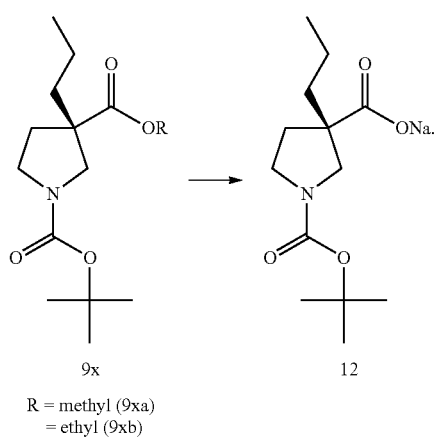

A certain embodiment of the invention is a process as described herein, wherein the desymmetrization of a compound of formula 16 to a compound of formula 17 is enzymatic hydrolysis using hydrolases like lipase from porcine pancreas.

A certain embodiment of the invention is a process as described herein, wherein the acid 10x is an intermediate for the conversion of 9x to 12

A certain embodiment of the invention is a process as described herein, wherein a compound of formula 12 is prepared from a compound of formula 15, comprising the following steps a) reacting a compound of formula 15 to a compound of formula 16

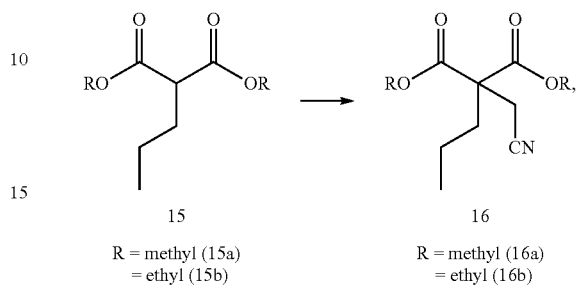

b) desymmetrization of a compound of formula 16 to a compound of formula 17 c) reducing a compound of formula 17 to a compound of formula 18

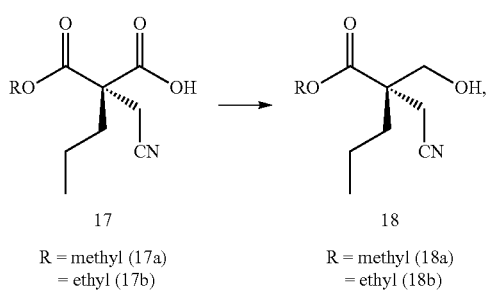

d) reacting a compound of formula 18 to a compound of formula 20

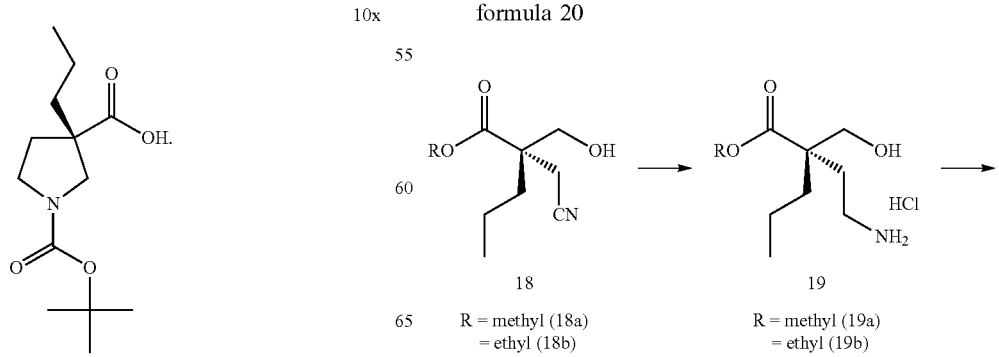

-continued

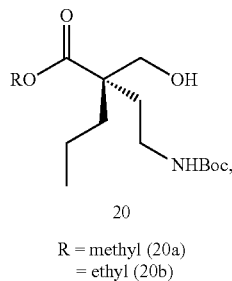

20
R = methyl (20a)
= ethyl (20b)

e) reacting a compound of formula 20 to a compound of formula 9x

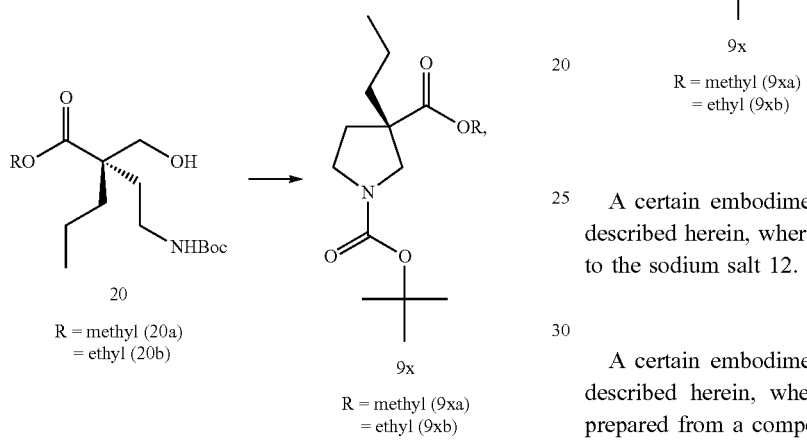

20
R = methyl (20a)
= ethyl (20b)

9x
R = methyl (9xa)
= ethyl (9xb)

f) conversion of a compound of formula 9x to the corresponding sodium salt of formula 12

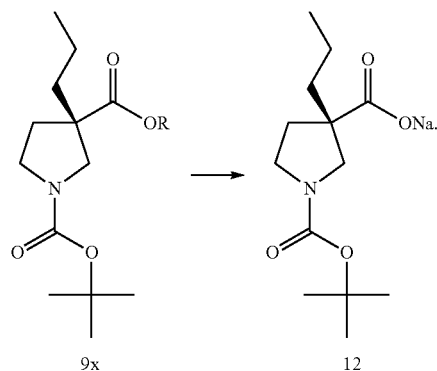

9x
R = methyl (9xa)
= ethyl (9xb)

12

A certain embodiment of the invention is a process as described herein, wherein the acid 20 is directly converted to the sodium salt 12.

A certain embodiment of the invention is a process as described herein, wherein a compound of formula I is prepared from a compound of formula 15, comprising the following steps

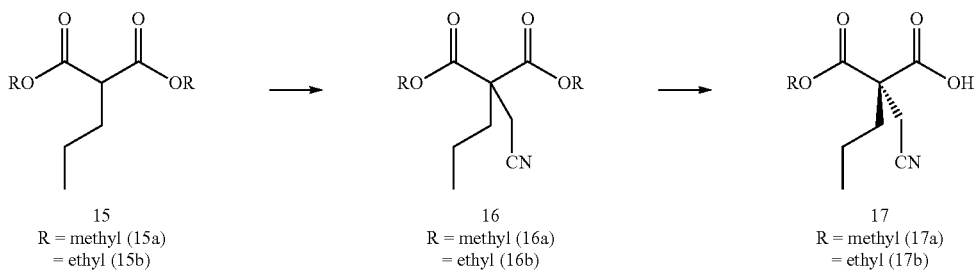

15
R = methyl (15a)
= ethyl (15b)

16
R = methyl (16a)
= ethyl (16b)

17
R = methyl (17a)
= ethyl (17b)

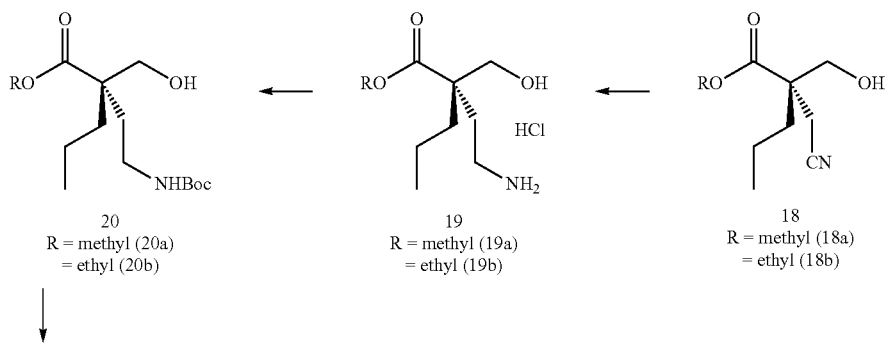

20
R = methyl (20a)
= ethyl (20b)

19
R = methyl (19a)
= ethyl (19b)

18
R = methyl (18a)
= ethyl (18b)

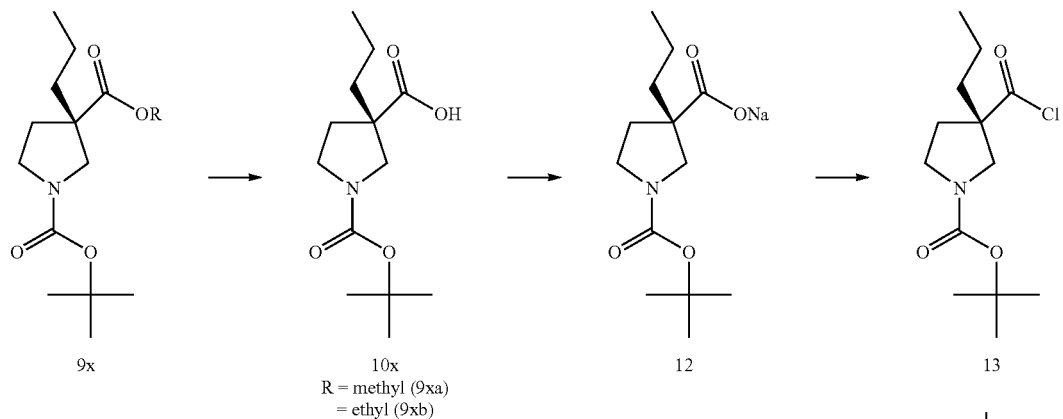
and optionally subsequent isolation of a compound of formula I or its quarterhydrate.
A certain embodiment of the invention is a process as described herein, wherein a compound of formula I is prepared from a compound of formula 2, comprising one or more of the following steps
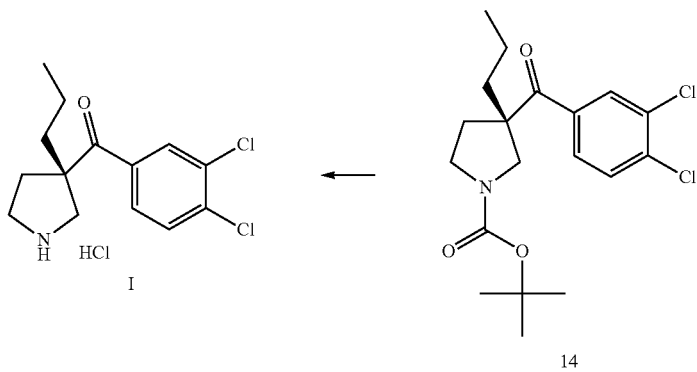
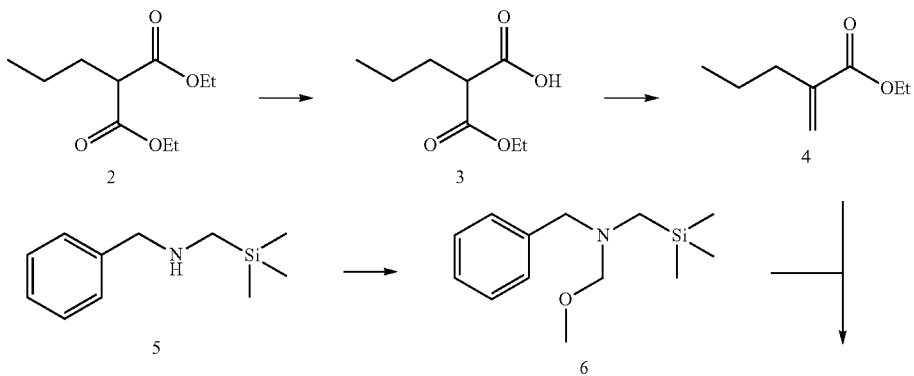

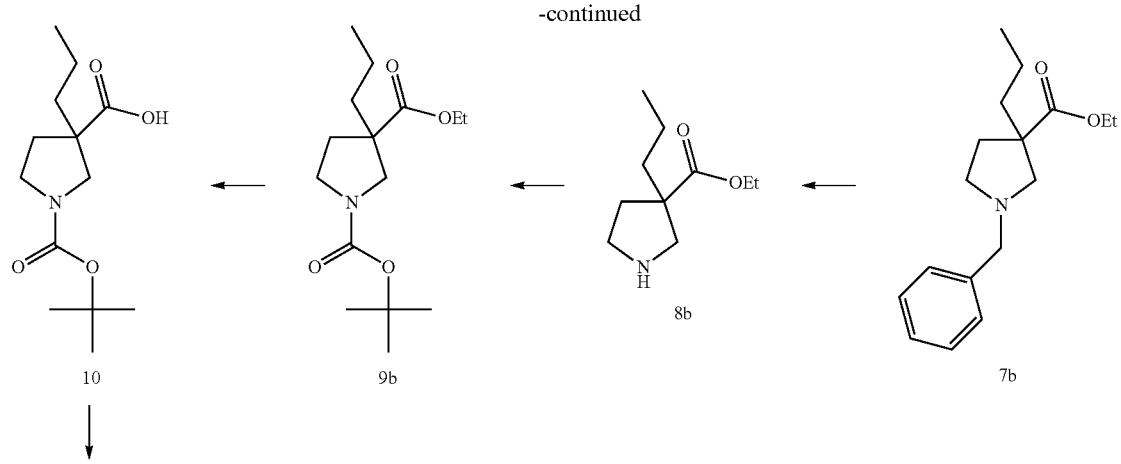
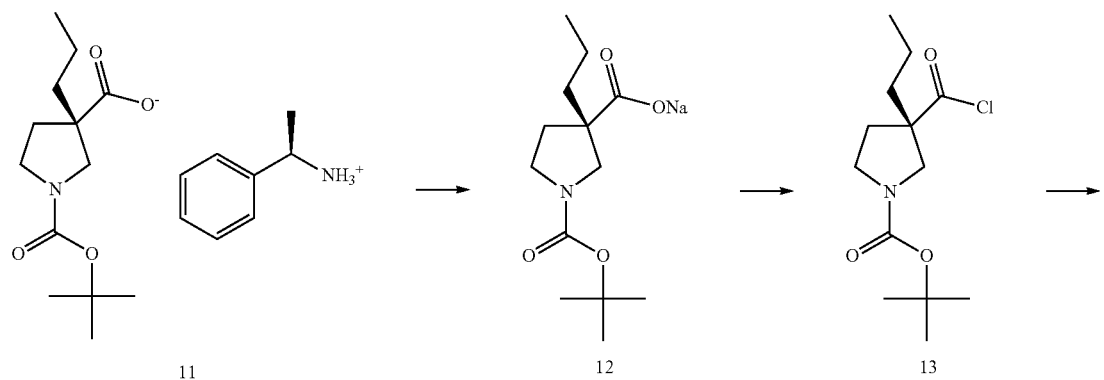
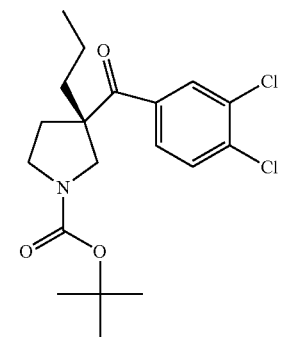
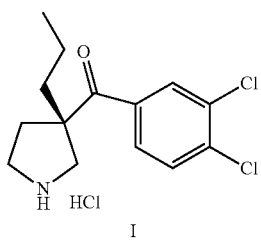
and optionally subsequent isolation of a compound of formula I or its quarterhydrate.

A certain embodiment of the invention is a process as described herein, wherein a compound of formula I is prepared from a compound of formula 2, comprising one or more of the following steps
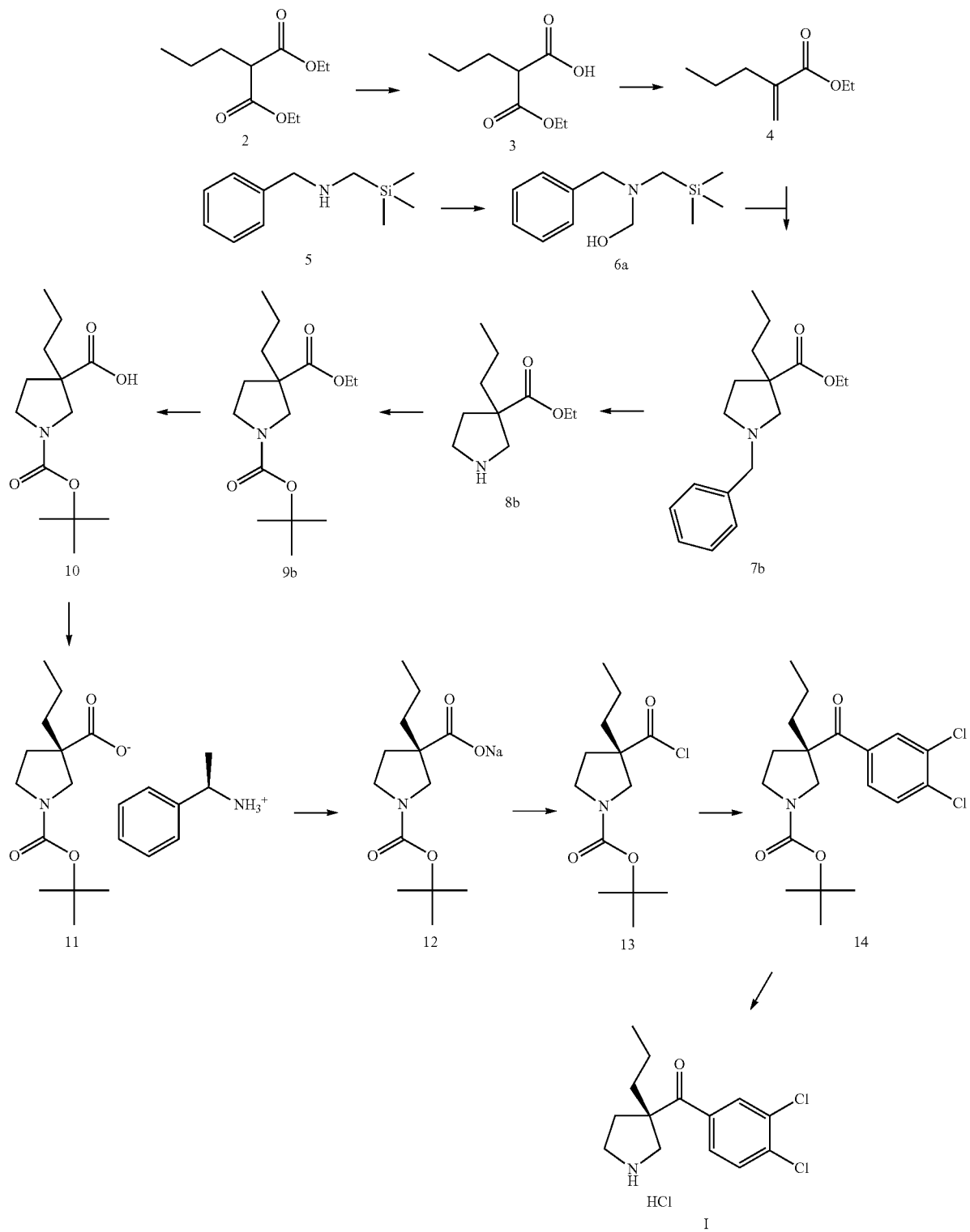
and optionally subsequent isolation of a compound of formula I or its quarterhydrate.

A certain embodiment of the invention is a process as described herein, wherein a compound of formula I is prepared from an acrylic acid ester, comprising the following steps.

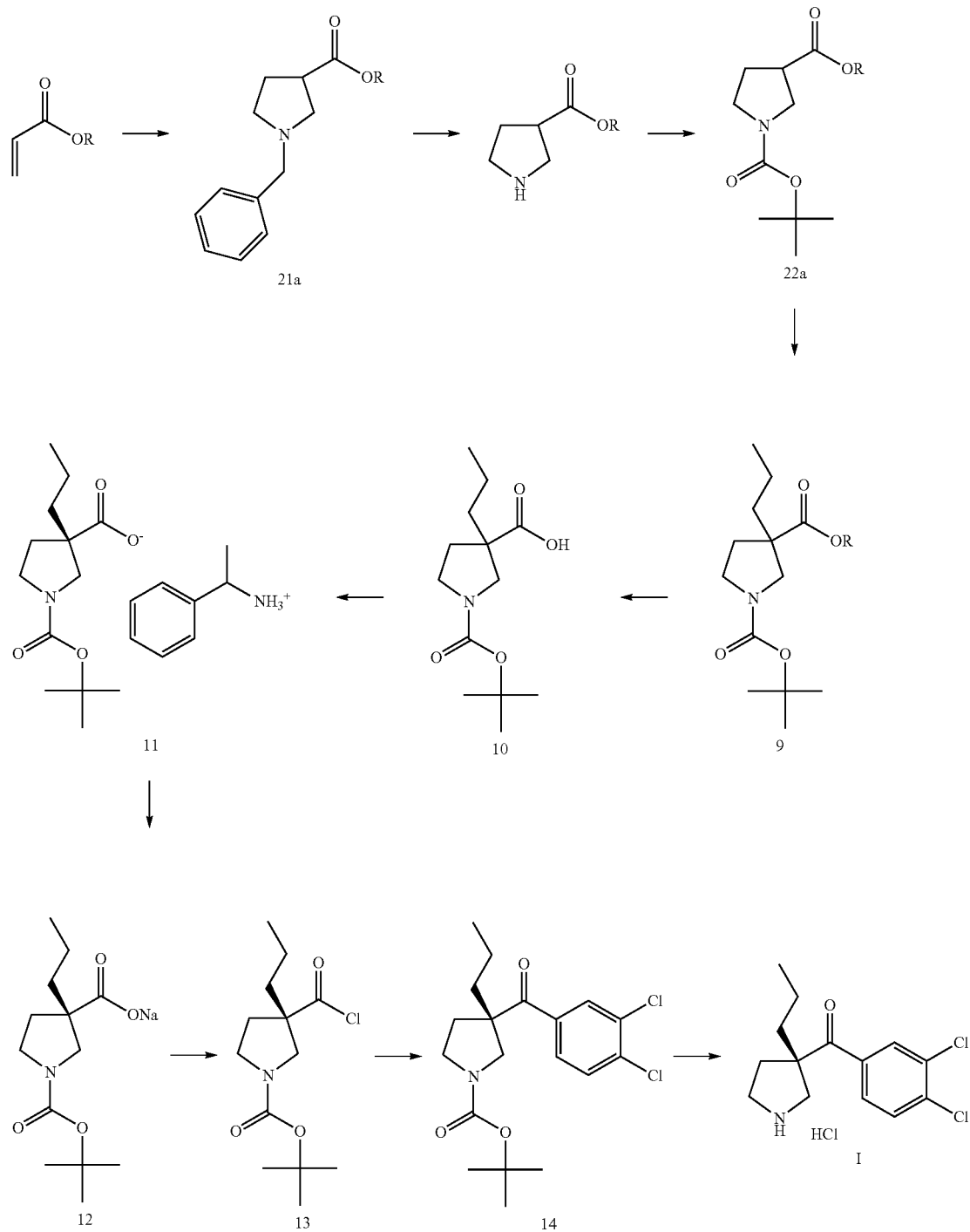

R = C$_{1-6}$alkyl

A certain embodiment of the invention is a process as described herein, wherein a compound of formula I is prepared from a compound of formula 2, comprising one or more of the following steps

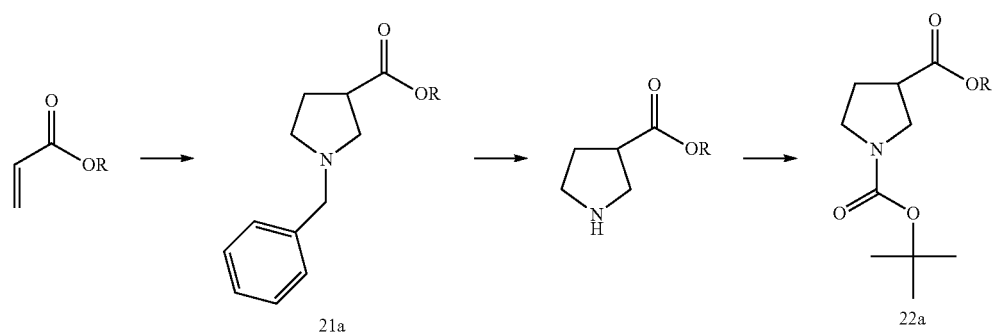
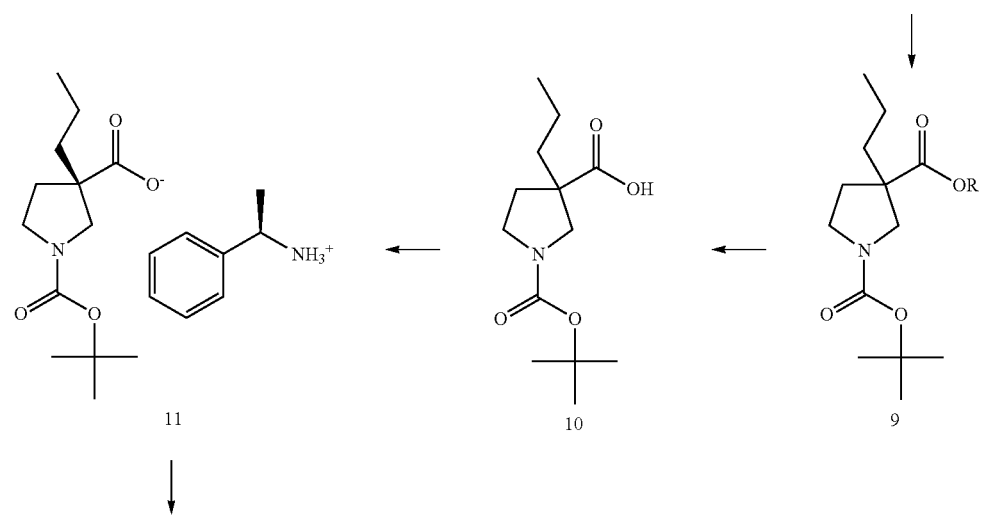
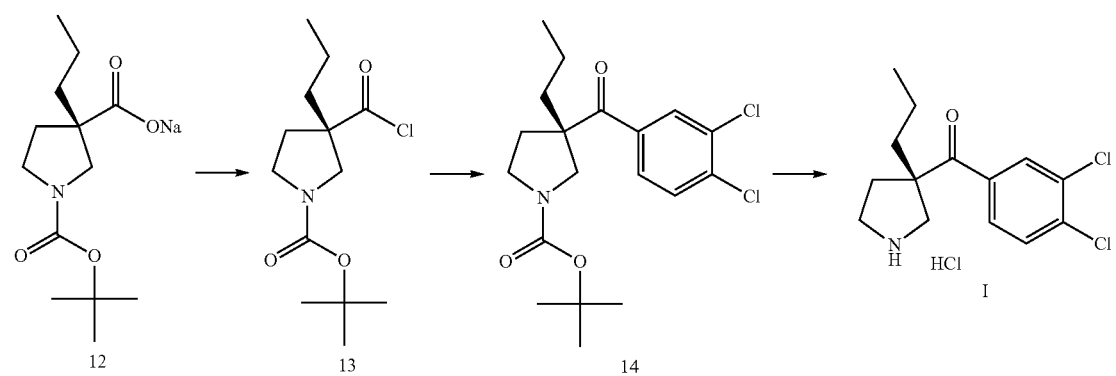
R = C$_{1-6}$alkyl
A certain embodiment of the invention is a process to synthesize a compound of formula 21a via [3+2] cycloaddition of acrylic acid esters.
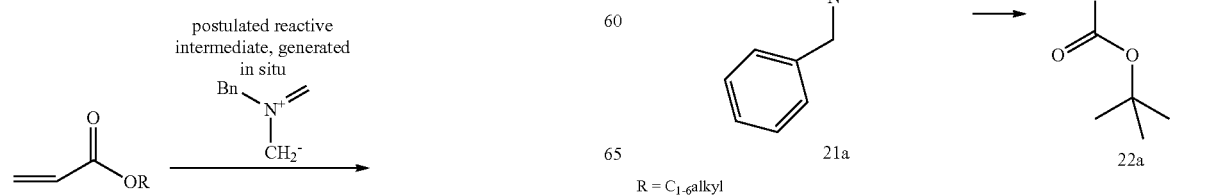
R = C$_{1-6}$alkyl The postulated azomethine ylide reactive intermediates like Bn-N$^+$—CH$_2^-$ can be generated in situ from the condensation of a glycine precursor and formaldehyde, followed by decarboxylation. Alternatively, the postulated azomethine ylide reactive intermediates can be generated in situ by iminium formation/desilylation (or desilylation/iminium formation) from precursor of type XCH$_2$OR (with X=benzyl and R=H or C$_{1-6}$alkyl), for example BCH$_2$OR. BCH$_2$OR can be prepared by reaction of (TMS-CH$_2$)—NH-Bn in methanol with a formaldehyde source like paraformaldehyde or aqueous formaldehyde.

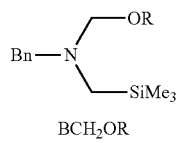

BCH$_2$OR
R = C$_{1-6}$alkyl, in particular Me
H

A certain embodiment of the invention is a process to synthesize a compound of formula 21a by not isolating of BCH$_2$OR out of the reaction mixture when preparing the azomethine ylide reactive intermediates. The process is simplified and isolation of the compound BCH$_2$OR (R=Me), which has been shown to be potentially thermally unstable (*Org. Proc. Res. & Dev.* 2005, 9, 193-197) can be avoided.

A certain embodiment of the invention is a process to synthesize a compound of formula 21a by using the azomethine ylide reactive intermediates prepared from BCH$_2$OR using an acid catalyst like trifluoroacetic acid (TFA), formic acid, acetic acid, in particular trifluoroacetic acid in a suitable solvent like THF and 2-Me-THF, in particular THF at for example room temperature.

A certain embodiment of the invention is a process to synthesize a compound of formula 21a at room temperature by first mixing the (TMS-CH$_2$)—NH-Bn and aqueous formaldehyde to form the corresponding hemiaminal (BCH$_2$OR, R=H), followed by addition of the olefin and a catalyst like 1-10 mol %, in particular between 1-5 mol %, more particular around 2 mol % TFA.

The use of aqueous formaldehyde to form in-situ the ylid precursor is known in the art (*Chemistry Lett.* 1996, 748). In this art, the cycloaddition is then performed under thermal conditions. Present process with the use of acid which catalyzed the process provides significant advantages over the art in terms of process robustness and reactivity and even allows for conducting the reactions at room temperature.

A certain embodiment of the invention is a process to synthesize a compound of formula 21 at room temperature by first mixing the (TMS-CH$_2$)—NH-Bn and aqueous formaldehyde to form the corresponding hemiaminal (BCH$_2$OR, R=H), followed by addition of the olefin and a catalyst like 1-10 mol %, in particular between 1-5 mol %, more particular around 2 mol % TFA using methyl acrylate as educt. A compound of formula 21 can further undergo a charcoal treatment prior to the debenzylation and Boc protection to provide a compound of formula 22.

A certain embodiment of the invention is a process to synthesize a compound of formula 21a by adding the premixed (TMS-CH$_2$)—NH-Bn and aqueous formaldehyde solution to a hot mixture of 40-60° C., in particular 50° C.±2° C. of the olefin and a catalyst like 1-10 mol %, in particular between 1-5 mol %, more particular around 2 mol % TFA.

A certain embodiment of the invention is a process to synthesize a compound of formula 21 by adding the premixed (TMS-CH$_2$)—NH-Bn and aqueous formaldehyde solution to a hot mixture of 40-60° C., in particular 50° C.±2° C. of the olefin and a catalyst like 1-10 mol %, in particular between 1-5 mol %, more particular around 2 mol % TFA using methyl acrylate as dipolarophile. A compound of formula 21 can further undergo a charcoal treatment prior to the debenzylation and Boc protection to provide a compound of formula 22.

A certain embodiment of the invention is a process to synthesize a compound of formula 21a by using the cheap and stable starting material (TMS-CH$_2$)—NH-Bn and by generating the ylide precursor in situ and avoid the crystallization of the cycloadduct hydrochloride. The art (*Org. Process Res. Dev.*, 2009, 13 (2), pp 292-296) indicates that the quality of compound 21a (R=Me) was critical to the outcome of the following debenzylation. The crude product obtained in the art did not allow a direct the debenzylation and required an additional purification step. Present process allows for an effective debenzylation of the crude cycloadduct 21a followed by in-situ Boc-protection and yet delivering high quality product 22a.

A certain embodiment of the invention is a process to synthesize a compound of formula 22a from a compound of formula 21a by deprotonation with strong bases like LiHMDS, KHMDS, NaHMDS, LDA, in particular LiHMDS and LDA, more particular LDA.

A certain embodiment of the invention is a process to synthesize a compound of formula 22a from a compound of formula 21a by deprotonation with LDA.

A certain embodiment of the invention is a process to synthesize a compound of formula 22a from a compound of formula 21a by deprotonation with LDA between –60° C. and –30° C., in particular between –50° C. and –40° C., more particular at –50° C.±2° C.

A certain embodiment of the invention is a process to synthesize a compound of formula 9 from a compound of formula 22a by alkylation with a propyl halide or mesylate, in particular a propyl iodide or mesylate, more particular 1-iodopropane.

A certain embodiment of the invention is a process to synthesize a compound of formula 9 from a compound of formula 22a by alkylation with a propyl halide or mesylate, in particular a propyl iodide or mesylate, more particular 1-iodopropane in a suitable solvent like THF or 2-MeTHF, in particular THF.

A certain embodiment of the invention is a process to synthesize a compound of formula 9 by cycloaddition of an azomethine ylide to the acrylate 4, debenzylation and Boc protection.

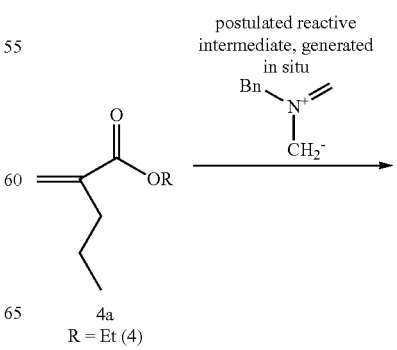

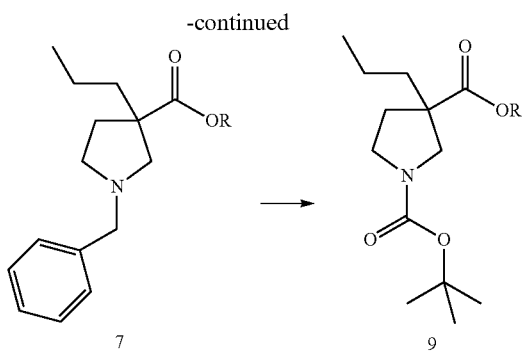

R = C$_{1-6}$alkyl

The intermediate azomethine ylid can be derived from BCH$_2$OR, as described herein.

A certain embodiment of the invention is a process to synthesize a compound of formula 9, wherein the cycloadduct 7 (R=Me (7a) or Et (7b), in particular R=Et) can be obtained by reaction of BCH$_2$OR with olefin 4, in the presence of a catalyst like TFA in an aprotic solvent like but not limited to THF or 2-MeTHF, in particular THF.

A certain embodiment of the invention is a process to synthesize a compound of formula 9, wherein the amount of water is minimized by using paraformaldehyde as a source of formaldehyde in the synthesis of the azomethine ylide.

A certain embodiment of the invention is a process to synthesize a compound of formula 9, wherein one equivalent of water/ylide is generated.

A certain embodiment of the invention is a process to synthesize a compound of formula 9, wherein the (TMS-CH$_2$)—NH-Bn precursor is reacted with paraformaldehyde in an aprotic solvent like THF or 2-MeTHF, in particular THF, in the presence of a base to provide the corresponding hemiaminal (BCH$_2$OR, R═H). Suitable bases include alkali alkoxides like KOtBu or organic bases like DBU and TMG, in particular KOtBu and TMG, more particular TMG. The azomethyne ylid precursor so obtained exhibit a higher reactivity compared to a process using aqueous formaldehyde. Decreasing the amount of water present in the reagent also decreases the chances of ylid quench during the cycloaddition process.

A certain embodiment of the invention is a process to synthesize a compound of formula 9, wherein a catalytic amount of TMG is used which is in particular 1-10%, more particular 1-5%, more particular around 2% at room temperature (RT) to 45° C., in particular between RT and 40° C., more particular at RT.

A certain embodiment of the invention is a process to synthesize a compound of formula 7, wherein the in situ generated azomethine ylide precursor exhibits a high reactivity and can be reacted with olefin 4 (R=Me or Et, in particular R=Et) in the presence of a catalyst like TFA to give the corresponding cycloadduct of formula 7. The amount of acid catalyst is in particular higher (in mol equiv.) than the amount of base used for the hemiaminal formation. Particular conditions use 2 mol % of TMG for the hemiaminal formation and 4 mol % of TFA to trigger the cycloaddition.

A certain embodiment of the invention is a process to synthesize a compound of formula 7, whereby alternative to olefin 4, dipolarophiles of suitable reactivity like, but not limited to, acrylic acid ester like e.g. methyl and ethyl acrylate which would lead to compounds of formula 21a, or fumaric acid diesters are used.

A certain embodiment of the invention is a process to synthesize a compound of formula 9 via classical resolution.

A certain embodiment of the invention is a process to synthesize a compound of formula 9, whereby intermediate 11 is obtained by resolution of the corresponding racemic acid 10 using R-phenyl-ethylamine as resolving agent. The resolution can be performed in organic solvents like heptane, Methyl-tert-butylether (MTBE), butyl acetate, methyl acetate, ethyl acetate, isopropyl acetate, in particular isopropyl acetate.

A certain embodiment of the invention is a process to synthesize a compound of formula 11 via classical resolution, whereby R-phenyl-ethylamine is used in 0.45-0.7 equivalents, in particular 0.5-0.6 equivalents.

A certain embodiment of the invention is a process to synthesize a compound of formula 11 via classical resolution, whereby an achiral tertiary amine base can be used as additive, for example 0.3-0.5 equiv. of the achiral tertiary amine base like diisopropylethylamine. In particular, the resolution can be performed without an achiral amine additive.

A certain embodiment of the invention is a process to synthesize a compound of formula 11, whereby a compound of formula 11 is obtained in >95:<5 diastereomeric purity.

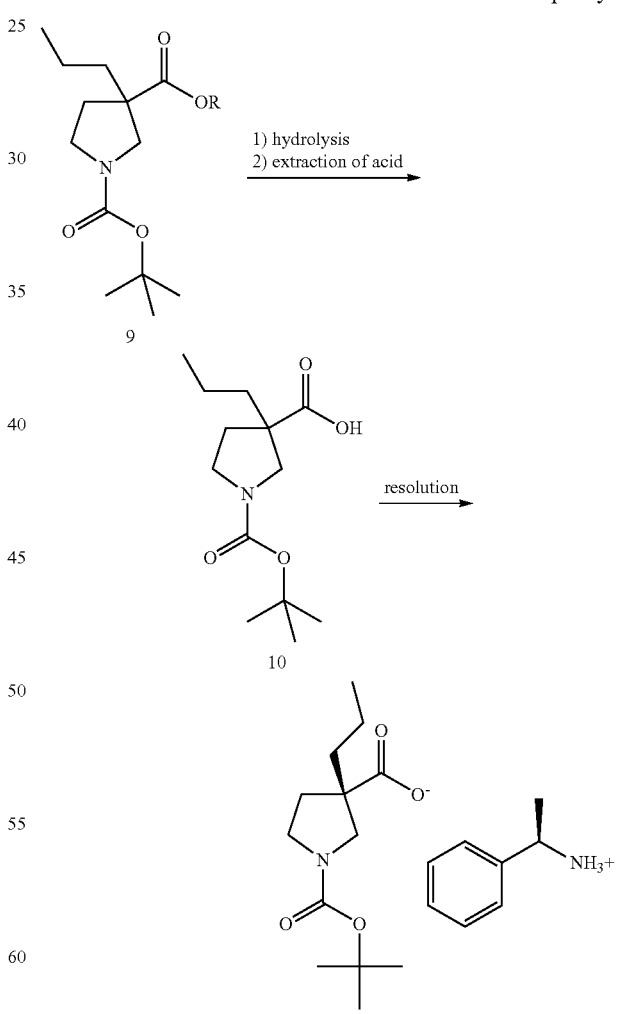

R = Me, Et

A certain embodiment of the invention is a process to hydrolyze a compound of formula 9 to a compound of formula 10 in an alcoholic solvent like methanol or ethanol by addition of a base like NaOH or KOH and with heating.

A certain embodiment of the invention is a process to synthesize a compound of formula 10, whereby the extraction of 10 is performed with isopropyl acetate.

A certain embodiment of the invention is a process to synthesize a compound of formula 10, whereby the solution of 10 after extraction is dried azeotropically and the resolution is performed by addition of R-phenyl-ethylamine.

A certain embodiment of the invention is a process to synthesize a compound of formula 17 via an enzymatic desymmetrization of intermediate 16.

A certain embodiment of the invention is a process to synthesize a compound of formula 17, whereby several microbial and mammalian hydrolases catalyze the formation of intermediate 17 with an enantiomeric excess above 70% such as the lipases from *Candida Antarctica* (A and B), *Chromobacterium viscosum*, *Humicola insolens*, porcine pancreas, *Rhizomucor miehei* and the esterase from rabbit liver and proteases from bovine pancreas, *Bacillus licheniformis*, in particular bovine pancreas protease and porcine pancreas lipase, more particular porcine pancreas lipase.

A certain embodiment of the invention is a process to synthesize a compound of formula 17, whereby malonate 16 is desymmetrized with R as $C_{1-5}$-alkyl or substituted $C_{1-3}$-alkyl, substituted by one or more substituents selected from the group consisting of hydroxy, methoxy, ethoxy and halogen, such as chloromethyl and methoxymethyl.

A certain embodiment of the invention is a process to synthesize a compound of formula 17, whereby malonate 16 is hydrolyzed at concentrations up to 20%, in particular 10% in a pH range of 6-9, in particular 8 in the presence of a water miscible organic solvent like THF and polyhydric alcohol like PEG at a temperature range from 25° C. to 45° C., in particular 30° C. by porcine pancreas lipase A certain embodiment of the invention is a process to synthesize a compound of formula 17, achieving an enantiomeric excess above 99% of the monoacid 17.

A certain embodiment of the invention is a process to synthesize a compound of formula 16, whereby the corresponding 2-propylmalonate 15 is alkylated with bromo- or chloroacetonitrile, in particular chloroacetonitrile.

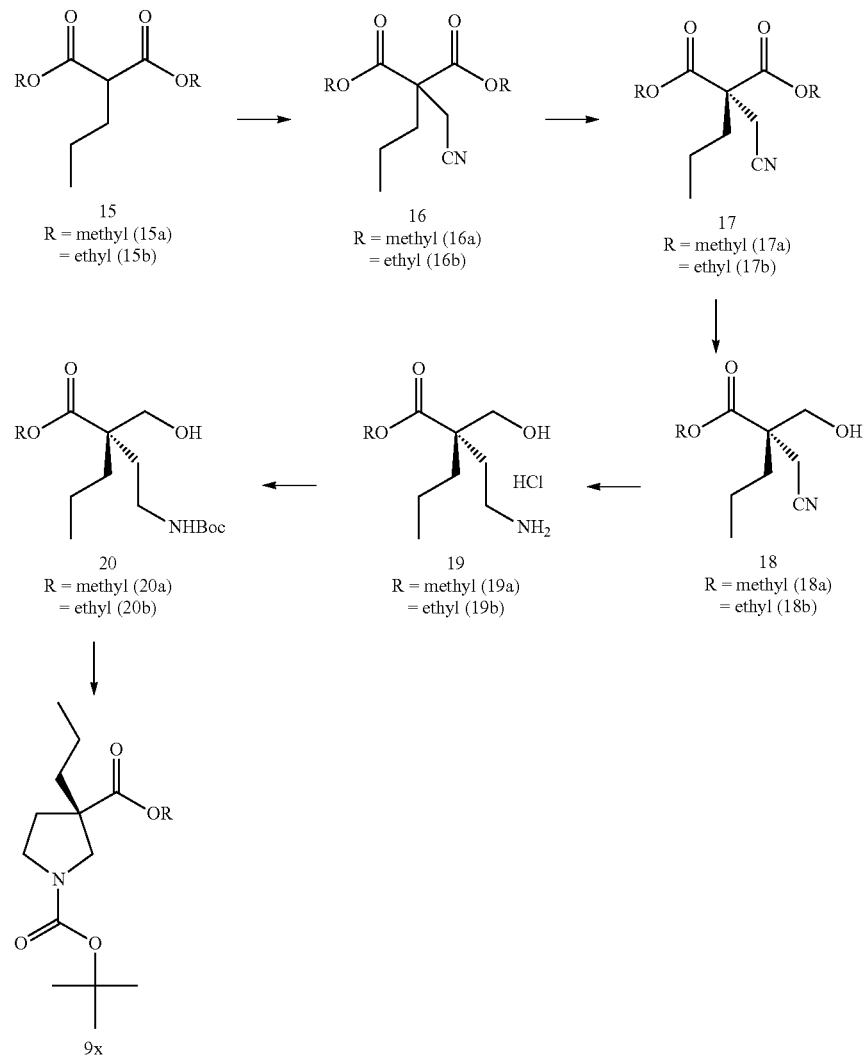

A certain embodiment of the invention is a process to synthesize a compound of formula 17, whereby malonate 16

A certain embodiment of the invention is a process to synthesize a compound of formula 18, whereby the enantiomerically enriched monoester monoacid 17 is reduced to the corresponding monoester alcohol 18, for example by activation of the acid function as a mixed anhydride, in particular derived from IBCF, followed by a selective reduction with a suitable reducing agent like NaBH$_4$ in the presence of an low molecular weight alcohol like MeOH or EtOH, in particular MeOH.

A certain embodiment of the invention is a process to synthesize a compound of formula 18, whereby the nitrile function of intermediate 18 can be reduced to the corresponding amine 19 with the use of platinum catalysts like PtO$_2$ or Pt/C, in particularly Pt/C in the presence of an acid like hydrochloric acid.

A certain embodiment of the invention is a process to synthesize a compound of formula 18, whereby the amine 19 is Boc protected to give intermediate 20.

A certain embodiment of the invention is a process to synthesize a compound of formula 18, whereby intermediate 20 is converted to pyrrolidine 9x by a Mitsunobu reaction.

A certain embodiment of the invention is a process to synthesize a compound of formula 18, whereby intermediate 20 is converted to pyrrolidine 9x activation of the hydroxyl function and intramolecular alkylation of the NHBoc, in particular the conditions involve the activation of the hydroxyl group by formation of the corresponding mesylate which undergoes an intramolecular alkylation to form 9x. The cyclization can be performed by treating the mesylate with trialkylamine bases like triethylamine, tripropylamine or Hünig's base, in particular triethylamine.

A certain embodiment of the invention is a process to synthesize a compound of formula 12, whereby a compound 9x is transformed to a compound 10x by hydrolysis followed by an acidic extraction. The acid 10x is then transformed to the sodium salt 12 by addition of NaOH or an alkoxide base like NaOMe or NaOEt in a suitable solvent like alcohols such as MeOH, EtOH, iPrOH or mixture thereof. After solvent exchange to EtOH or iPrOH, in particular iPrOH, the sodium salt 12 can be crystallized.

A certain embodiment of the invention is a process to synthesize a compound of formula 12, whereby an ester 9x can be hydrolyzed using NaOH in an alcohol like MeOH or EtOH under heating. The resulting sodium salt 12 can be directly isolated by performing a solvent exchange to EtOH or iPrOH, in particular iPrOH followed by crystallization.

A certain embodiment of the invention is a process to synthesize a compound of formula 12, whereby the free acid 10x is formed by liberation of amine salt 11 and extraction. The acid 10x is then transformed to sodium salt 12 by addition of NaOH or an alkoxide base like NaOMe or NaOEt. Suitable solvents include alcohols like MeOH, EtOH, iPrOH or mixture thereof. The sodium salt can then be isolated after solvent exchange to EtOH or iPrOH, preferably iPrOH and crystallization.

A certain embodiment of the invention is a process to synthesize a compound of formula 12, whereby amine salt 11 is directly transformed into salt 12 by addition of NaOH, NaOMe or NaOEt, in particular NaOH in a suitable solvent like MeOH, EtOH or iPrOH or a mixture thereof. Suitable conditions involve the use of a methanolic solution of NaOH in a suitable solvent like MeOH or iPrOH. A solvent exchange to EtOH or iPrOH, in particular iPrOH allows for the isolation of salt 12 by crystallization.

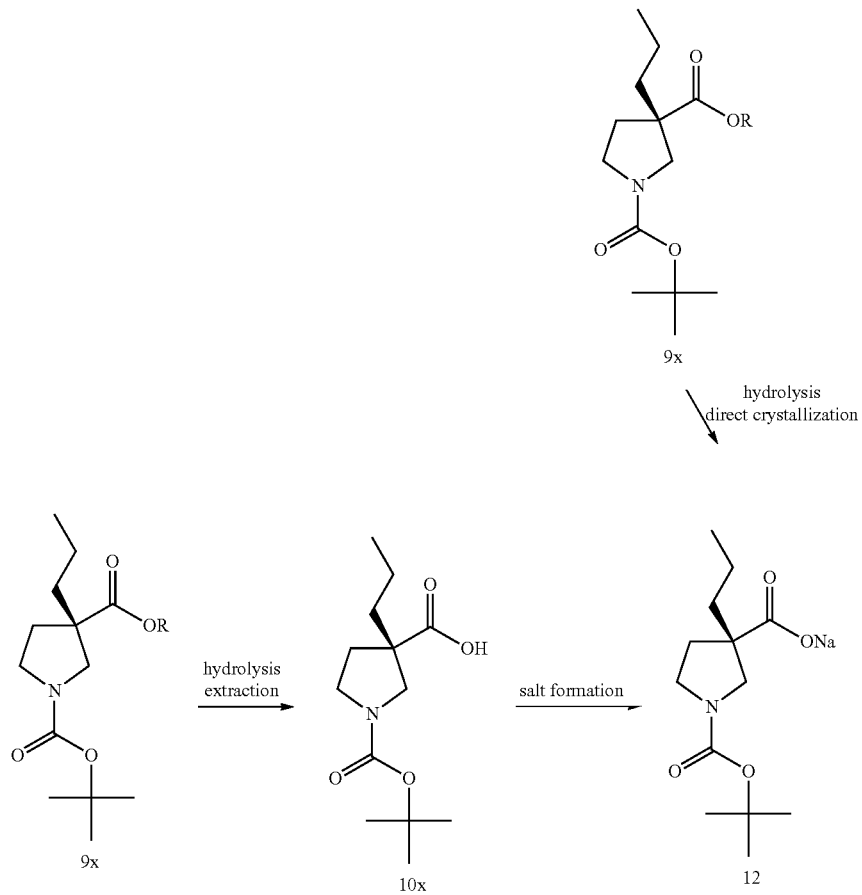

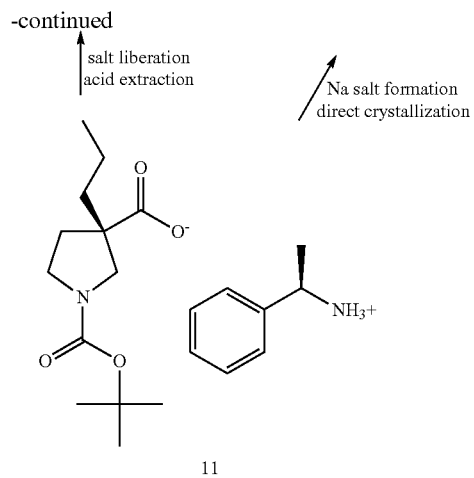

11

R = C$_{1-6}$alkyl, in particular Me or Et

A certain embodiment of the invention is a process to synthesize a compound of formula 12, whereby sodium salt 12 of enantiomeric ratio of >98.5:<1.5, in particular >99:<1 is obtained from amine salt 11 of for example 97:3 d.r.

A certain embodiment of the invention is a process to synthesize a compound of formula 13, by reaction of sodium salt 12 with oxalyl chloride in a suitable solvent like dichloromethane or toluene, in particular toluene.

A certain embodiment of the invention is a process to synthesize a compound of formula 13, by reaction of sodium salt 12 with oxalyl chloride in a suitable solvent like dichloromethane or toluene, in particular toluene in the presence of a secondary amide catalyst like DMF at a temperature between −20° C. and 40° C., in particular between −20° C. and RT, more particular between −10° C. and 0° C.

A certain embodiment of the invention is a process to synthesize a compound of formula 13 by reaction of sodium salt 12 with oxalyl chloride, whereby the reaction mixture is warmed to RT after complete addition of the oxalyl chloride.

A certain embodiment of the invention is a process to synthesize a compound of formula 13 by reaction of sodium salt 12 with oxalyl chloride, whereby a catalytic amount of DMF is present.

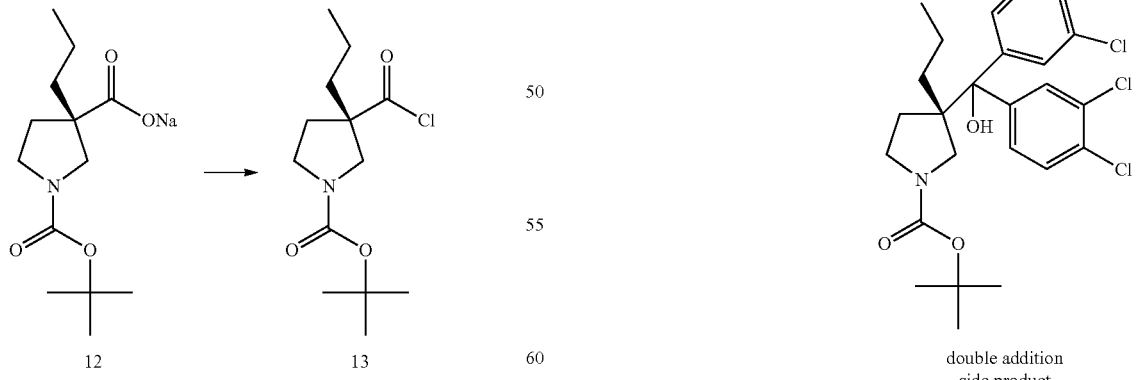

A certain embodiment of the invention is a process to synthesize a compound of formula 14 via addition of a Grignard reagent.

A certain embodiment of the invention is a process to synthesize a compound of formula 14 via addition of a Grignard reagent, whereby the Grignard reagent is prepared by reaction of 1-bromo-3,4-dichlorobenzene and magnesium in solvents like THF or 2-MeTHF, in particular THF.

A certain embodiment of the invention is a process to synthesize a compound of formula 14 via addition of a Grignard reagent, whereby the formation of the double addition side product is reduced by performing the reaction in the presence of a Cu(I) catalyst like CuCl, CuI, CuBr, in particular CuCl.

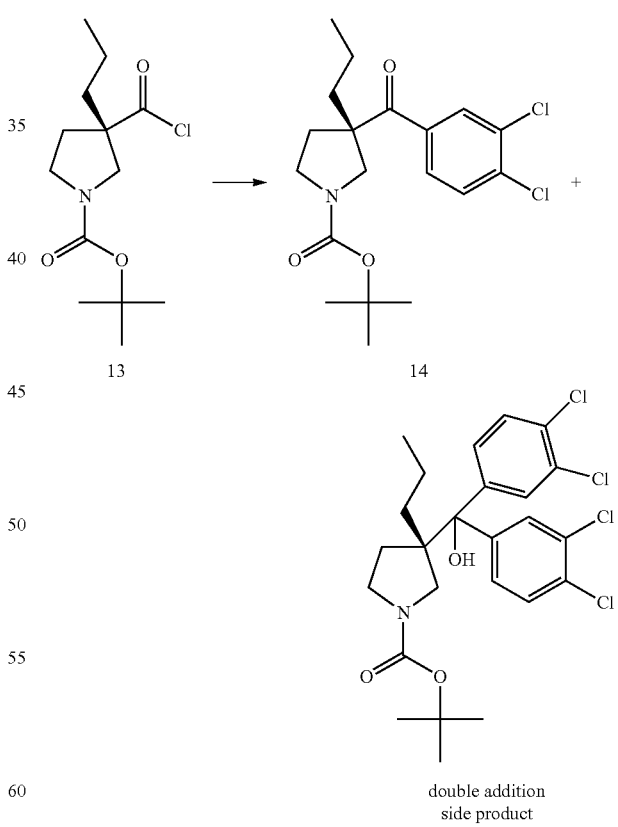

double addition
side product

A certain embodiment of the invention is a process to synthesize a compound of formula 14 via addition of a Grignard reagent, whereby the CuCl catalyst is used in 1-10 mol %, in particular 2-5 mol %, more particular between 1-2 mol %.

A certain embodiment of the invention is a process to synthesize a compound of formula 14 via addition of a Grignard reagent, whereby reaction is performed in THF/toluene mixtures (the acid chloride is used as a toluene solution) at −20° C. to 40° C., in particular between −10° C. and RT, more particular at 0° C.±2° C.

A certain embodiment of the invention is a process to synthesize a compound of formula 14 via addition of a Grignard reagent, whereby the Grignard needs to be used in slight excess like 1.1-1.5 equiv, in particular 1.3 equiv.

A certain embodiment of the invention is a process to synthesize a compound of formula 14 via addition of a Grignard reagent at 0° C., by the addition of 1.3-1.4 equiv. of Grignard over >30 min, in particular >1 h.

A certain embodiment of the invention is a process to synthesize a compound of formula 14 via addition of a Grignard reagent, whereby the tetrachlorobiphenyl by-product is removed by crystallization of compound of formula I after Boc-deprotection.

A certain embodiment of the invention is a process to synthesize a compound of formula 14 via addition of a Grignard reagent at 0° to 50° C., in particular between RT and 40° C., in the presence of PMDTA (1-2 equiv., in particular 1.5 equiv.).

A certain embodiment of the invention is a process to synthesize a compound of formula I via deprotection of ketone 14, whereby a toluene solution of ketone 14 is added to a hot (between 50-80° C., in particular around 60° C.) mixture of toluene and concentrated aqueous HCl (in particular >30% concentration, more particular >35%).

A certain embodiment of the invention is a process to isolate a compound of formula I under anhydrous conditions.

A certain embodiment of the invention is a process to isolate a quarterhydrate of a compound of formula I by conducting the crystallization in a toluene/water mixture or in a toluene/AcOEt/water mixture, in particular in a toluene AcOEt/water mixture, whereby the amount of water required is >0.25 equiv.

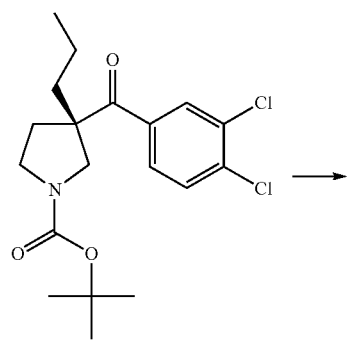

14

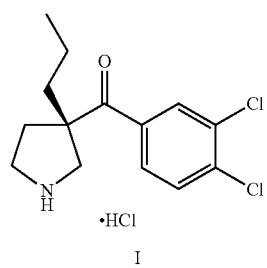

·HCl

I

A certain embodiment of the invention is the transformation of an anhydrate of a compound of formula I to a quarterhydrate of a compound of formula I.

A certain embodiment of the invention is the transformation of an anhydrate of a compound of formula I to a quarterhydrate of a compound of formula I, whereby the anhydrate form of I can be transformed into its quarterhydrate form by dissolution in ethanol followed by a crystallization in AcOEt/EtOH/water mixture or AcOEt/water mixture after a suitable solvent exchange and the addition of the required amount of water, i.e. at least 0.25 equiv., in particular between 0.25 and 5 equiv, more particular between 0.25 and 1 equiv., most particular 0.5 equiv. water.

A certain embodiment of the invention is the transformation of an anhydrate of a compound of formula I to a quarterhydrate of a compound of formula I, whereby the anhydrate form of I can be transformed into its quarterhydrate form by digestion in a AcOEt/EtOH/water mixture or AcOEt/water mixture.

A certain embodiment of the invention is a compound as described herein, whenever prepared using a process as described herein.

A certain embodiment of the invention is a compound as described herein for use as a medicament.

A certain embodiment of the invention is a compound of formula I as described herein for use as a medicament.

A certain embodiment of the invention is a compound as described in any of the embodiments for the use as therapeutically active substance or medicament.

A certain embodiment of the invention is a compound of formula I as described in any of the embodiments for the use as therapeutically active substance or medicament.

A certain embodiment of the invention is a compound as described in any of the embodiments for the use as monoamine transporter inhibitor, wherein said monoamine transporter is a member selected from the group consisting of serotonin transporter (SERT), dopamine transporter (DAT), norepinephrine transporter (NET) and combinations thereof, in particular the combination of the three transporters.

A certain embodiment of the invention is a compound as described in any of the embodiments for a use in the prevention or treatment central nervous system disorder, in particular the central nervous system disorder is a disorder selected from the group consisting of depression, cognitive deficit, fibromyalgia, pain such as neuropathic pain, sleep disorder such as sleep apnea, narcolepsy, excessive daytime sleepiness and the like, attention deficit disorder (ADD), attention deficit hyperactivity disorder (ADHD), restless leg syndrome, schizophrenia, anxiety, obsessive compulsive disorder, posttraumatic stress disorder, metabolic disorders such as obesity (juvenile and adolescent) and the like, premenstrual dysphoria, and neurodegenerative disease such as Parkinson's disease.

A certain embodiment of the invention is a compound as described in any of the embodiments for a use in the prevention or treatment of depression, anxiety or both. In particular said depression is a member selected from the group consisting of anxious depression, major depressive disorder (MDD), unipolar depression, bipolar disorder type I (juvenile and adolescent) and type II (juvenile and adolescent), seasonal affective disorder (SAD), postpartum depression, clinical depression, treatment resistant depression (TRD), drug-induced depression, somatic depression and dysthymia.

A certain embodiment of the invention is a pharmaceutical composition comprising a compound as described in any of the embodiments.

Starting materials are commercially available, known in the art or can be prepared by methods known in the art or in analogy thereto.

It will be appreciated that the compounds of formula I in this invention can be derivatised at functional groups to provide derivatives which are capable of conversion back to the parent compound in vivo.

Pharmaceutical Compositions

The compounds of formula I as well as their pharmaceutically acceptable salts can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The compounds of formula I and their pharmaceutically acceptable salts can be processed with pharmaceutically inert, inorganic or organic excipients for the production of tablets, coated tablets, dragées and hard gelatine capsules. Lactose, corn starch or derivatives thereof, talc, stearic acid or its salts etc can be used as such excipients e.g. for tablets, dragées and hard gelatine capsules. Suitable excipients for soft gelatine capsules are e.g. vegetable oils, waxes, fats, semisolid and liquid polyols etc.

Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary within wide limits and will, of course, be fitted to the individual requirements in each particular case. In general, in the case of oral administration a daily dosage of about 10 to 1000 mg per person of a compound of formula I should be appropriate, although the above upper limit can also be exceeded when necessary.

Examples of compositions according to the invention are, but are not limited to:

Example A

Tablets of the following composition are manufactured in the usual manner:

TABLE 1 possible tablet composition

| ingredient | mg/tablet | | | |
|---|---|---|---|---|
| | 5 | 25 | 100 | 500 |
| 1. compound of formula I | 5 | 25 | 100 | 500 |
| 2. lactose | 45 | 105 | 30 | 150 |
| 3. corn starch | 15 | 6 | 6 | 60 |
| 4. microcrystalline cellulose | 34 | 30 | 30 | 450 |
| 5. magnesium stearate | 1 | 1 | 1 | 1 |
| total | 100 | 167 | 167 | 831 |

Manufacturing Procedure
1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Example B-1

Capsules of the following composition are manufactured:

TABLE 2 possible capsule ingredient composition

| ingredient | mg/capsule | | | | |
|---|---|---|---|---|---|
| | 5 | 10 | 25 | 100 | 500 |
| 1. compound of formula I | 5 | 10 | 25 | 100 | 500 |
| 2. lactose | 159 | 155 | 123 | 148 | — |
| 3. corn starch | 25 | 30 | 35 | 40 | 70 |
| 4. talc | 10 | 5 | 15 | 10 | 25 |
| 5. magnesium stearate | 1 | — | 2 | 2 | 5 |
| total | 200 | 200 | 200 | 300 | 600 |

Manufacturing Procedure
1. Mix ingredients 1, 2 and 3 in a suitable mixer for 30 minutes.
2. Add ingredients 4 and 5 and mix for 3 minutes.
3. Fill into a suitable capsule.

The compound of formula I, lactose and corn starch are firstly mixed in a mixer and then in a comminuting machine. The mixture is returned to the mixer, the talc (and magnesium stearate) is added thereto and mixed thoroughly. The mixture is filled by machine into suitable capsules, e.g. hard gelatine capsules.

Example B-2

Soft Gelatine Capsules of the following composition are manufactured:

TABLE 3 possible soft gelatine capsule ingredient composition

| ingredient | mg/capsule |
|---|---|
| compound of formula I | 5 |
| yellow wax | 8 |
| hydrogenated soybean oil | 8 |
| partially hydrogenated plant oils | 34 |
| soybean oil | 110 |
| total | 165 |

TABLE 4 possible soft gelatine capsule composition

| ingredient | mg/capsule |
|---|---|
| gelatine | 75 |
| glycerol 85% | 32 |
| karion 83 | 8 (dry matter) |
| titaniumdioxide | 0.4 |
| iron oxide yellow | 1.1 |
| total | 116.5 |

Manufacturing Procedure
The compound of formula I is dissolved in a warm melting of the other ingredients and the mixture is filled into soft gelatin capsules of appropriate size. The filled soft gelatin capsules are treated according to the usual procedures.

Example C

Suppositories of the following composition are manufactured:

TABLE 5 possible suppository composition

| ingredient | mg/supp. |
|---|---|
| compound of formula I | 15 |
| suppository mass | 1285 |
| total | 1300 |

Manufacturing Procedure

The suppository mass is melted in a glass or steel vessel, mixed thoroughly and cooled to 45° C. Thereupon, the finely powdered compound of formula I is added thereto and stirred until it has dispersed completely. The mixture is poured into suppository moulds of suitable size, left to cool; the suppositories are then removed from the moulds and packed individually in wax paper or metal foil.

Example D

Injection solutions of the following composition are manufactured:

TABLE 6 possible injection solution composition

| ingredient | mg/injection solution. |
|---|---|
| compound of formula I | 3 |
| polyethylene Glycol 400 | 150 |
| acetic acid | q.s. ad pH 5.0 |
| water for injection solutions | ad 1.0 ml |

Manufacturing Procedure

The compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example E

Sachets of the following composition are manufactured:

TABLE 7 possible sachet composition

| ingredient | mg/sachet |
|---|---|
| compound of formula I | 50 |
| lactose, fine powder | 1015 |
| microcrystalline cellulose (AVICEL PH 102) | 1400 |
| sodium carboxymethyl cellulose | 14 |
| polyvinylpyrrolidon K 30 | 10 |
| Magnesium stearate | 10 |
| flavoring additives | 1 |
| total | 2500 |

Manufacturing Procedure

The compound of formula I is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

EXPERIMENTAL PART

The following experiments are provided for illustration of the invention. They should not be considered as limiting the scope of the invention, but merely as being representative thereof.

Synthesis of 1-(3,4-Dichloro-phenyl)-pentan-1-one (II)

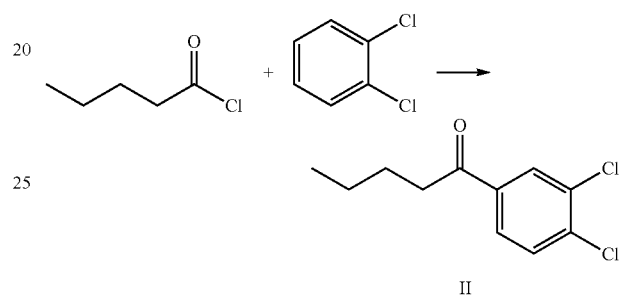

Aluminum chloride (12.4 g, 93.3 mmol, Eq: 1.5) was charged in the reactor followed by 1,2-dichlorobenzene (27.4 g, 21.0 ml, 187 mmol, Eq: 3). The suspension was heated to 80° C. in 10 min and pentanoyl chloride (7.5 g, 7.58 ml, 62.2 mmol, Eq: 1.00) was added dropwise over 30 min. The reaction mixture went from a yellow suspension to an orange/brown viscous solution. After 5 h reaction at 80° C. the deep orange/brown reaction mixture was cooled to 25° C. and stirred at 25° C. overnight. The reaction mixture was poured onto a mixture of n-heptane (68.4 g, 100 ml) and water/ice 50:50 (100 g, 100 ml). The organic phase was separated and washed with water (50.0 g, 50 ml) then with $NaHCO_3$aq 5% (50 ml) and finally with water (50.0 g, 50 ml). The organic phase was dried azeotropically (60° C./ca 150 mbar) with n-heptane (205 g, 300 ml) to give 28 g of crude product as an orange oil (ca 96:4 Product/2,3-dichlorovalerophenone isomer). The crude oil was dissolved in n-heptane (27.4 g, 40 ml) and the solution was cooled to −20° C. for 2 h. The suspension was filtered. The filter was washed with cold n-heptane (10.3 g, 15 ml) and dried at 35° C./10 mbar to give 8.8 g of the title product (>98a % GC, isomer<1%).

Synthesis of 1-(3,4-Dichloro-phenyl)-2-methylene-pentan-1-one (IV)

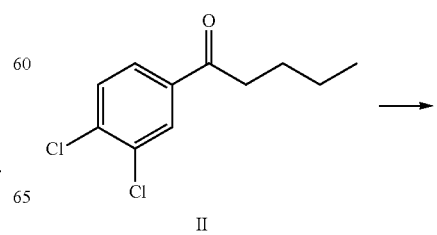

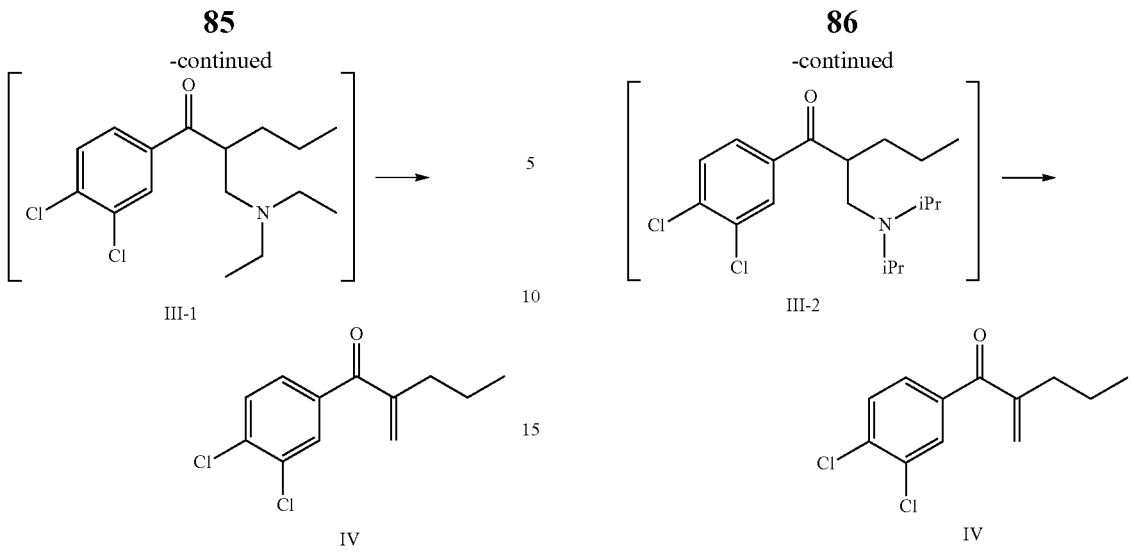

Alternative A 1-(3,4-dichlorophenyl)pentan-1-one II (15 g, 63.0 mmol, equivalents: 1.00) and paraformaldehyde (3.58 g, 113 mmol, equivalents: 1.8) were charged in the reactor followed by heptane (30.0 ml). Temperature was set at 25° C. Diethylamine (8.84 g, 12.5 ml, 120 mmol, equivalents: 1.9) was added. Paraformaldehyde partially dissolved over time. Acetic acid (11.4 g, 10.9 ml, 189 mmol, equivalents: 3) was slowly added and the reaction mixture was heated to 60° C. After 17 h reaction (<2% starting material), deionized water (30.0 ml) was added and the reaction mixture was heated to 80° C. After completion of the reaction (usually <5 h, <1% intermediate by HPLC), the reaction mixture was cooled to room temperature. The organic phase was separated and washed twice with 20 mL deionized water. The organic phase was concentrated under reduced pressure and dried azeotropically with heptane to give 15.32 g of the olefin IV as orange oil (96% yield corrected for 96a % purity by HPLC).

Alternative B 1-(3,4-dichlorophenyl)pentan-1-one II (15 g, 63.0 mmol, equivalents: 1.00) and paraformaldehyde (3.58 g, 113 mmol, equivalents 1.8) were charged in the reactor followed by heptane (20.5 g, 30.0 ml). Temperature was set to 25° C. Acetic acid (11.4 g, 10.9 ml, 189 mmol, equivalents: 3) was added followed by diethylamine (8.84 g, 12.5 ml, 120 mmol, equivalents: 1.9). The reaction mixture was heated to 60° C. After 17 h30 reaction (<2% starting material), deionized water (30.0 ml) was added and the reaction mixture was heated to 80° C. After completion of the reaction (usually <5 h; <1% intermediate by HPLC), the reaction mixture was cooled to room temperature and polish filtered. The aqueous phase was separated and discarded. The organic phase was washed twice with 20 mL deionized water and once with 10 mL 25% aqueous sodium chloride. The organic phase was concentrated under reduced pressure and dried azeotropically with heptane to give 15.53 g of the desired product IV as orange oil (99% yield, corrected for 97.7%).

Alternative C 1-(3,4-dichlorophenyl)pentan-1-one II (15 g, 63.0 mmol, equivalents: 1.00) was charged in the reactor followed by tetrahydrofuran (THF) (45.0 ml). 37.5% aqueous formaldehyde (8.57 g, 7.91 ml, 107 mmol, equivalents: 1.7) was added followed by diisopropylamine (11.6 g, 16.2 ml, 113 mmol, equivalents: 1.8). Acetic acid (7.6 g, 7.24 ml, 126 mmol, equivalents: 2) was added and the reaction mixture was heated to 60° C. overnight (IPC by HPLC). After 18 hrs reaction, the reaction mixture was cooled to RT. Water (15 mL) and heptane (40 mL) were added. The THF was removed at the rotavap (250 mbar/50° C.). The organic phase was separated and washed twice with water (40 ml). The crude product solution was dried azeotropically under reduced pressure (ca 150 mbar/60° C.) with heptane and concentrated to give 15.53 g of product IV as an orange oil (93% yield corrected for 92a % purity by HPLC).

Alternative D

The reaction can be performed in analogy to alternative C with paraformaldehyde instead of aqueous formaldehyde.

Synthesis of (1-Benzyl-3-propyl-pyrrolidin-3-yl)-(3,4-dichloro-phenyl)-methanone VIII

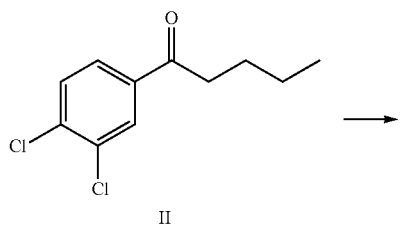

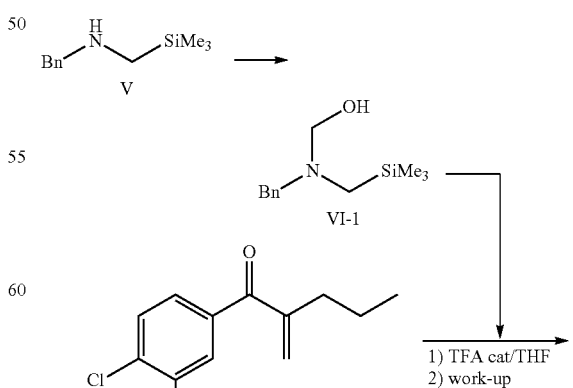

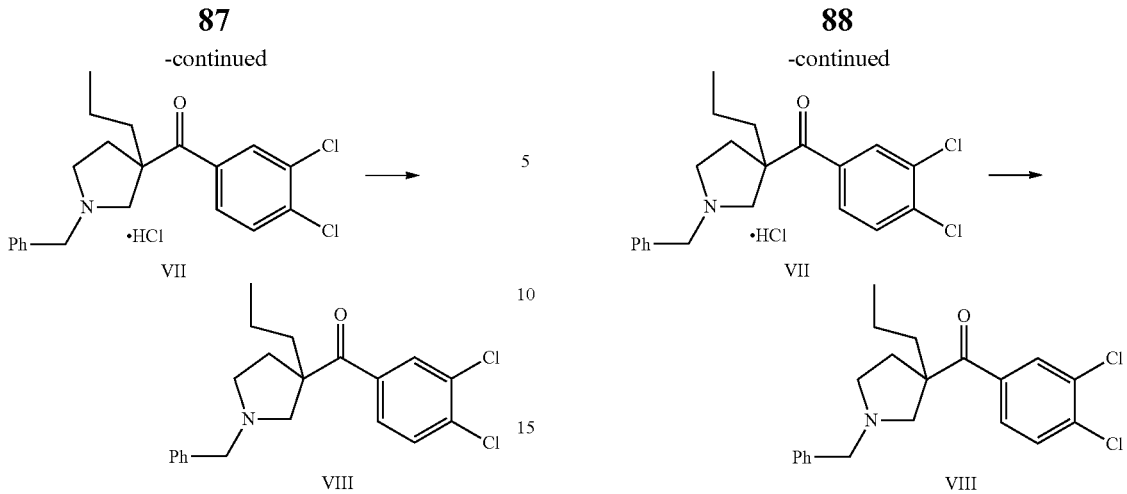

Alternative A

Paraformaldehyde (3.51 g, 111 mmol, Eq: 1.35) was suspended in THF (106 g, 120 ml). N-benzyl-1-(trimethylsilyl)methanamine VI-1 (21.5 g, 111 mmol, Eq: 1.35) and 1,1,3,3-tetramethylguanidine (239 mg, 261 µl, 2.06 mmol, Eq: 0.025) were added and the white suspension was heated to 40° C. within 20 min. After 30 min at 40° C., the resulting colorless solution was cooled to RT and added at 20-25° C. over 1 h to a solution of 1-(3,4-dichlorophenyl)-2-methylenepentan-1-one (20 g, 82.3 mmol, Eq: 1.00) and trifluoroacetic acid (586 mg, 394 µl, 5.14 mmol, Eq: 0.0625) in THF (40.0 ml). After 1 h at RT, the yellow solution was transferred in a 500 ml round bottom flask. The reactor was washed with 40 ml THF. The solution was concentrated at 40° C./250-15 mbar. The resulting oily residue was dissolved in toluene (360 ml) and washed with a solution consisting of 1 M aqueous HCl (180 ml), brine (180 ml) and ethanol (36 ml). The organic phase was separated concentrated under reduced pressure at 40° C. to give 100.5 g crude solid. The yellow solid was solvent chased twice with 50 mL ethyl acetate and dried at 40° C. under reduced pressure to give 65 g product hydrochloride. The crude product was suspended in ethyl acetate (310 ml) and ethanol (17 ml). The light yellow suspension was stirred 16 h at RT and was filtered. The white filter cake was washed with ethyl acetate (100 ml) and dried 2 h at 40° C./15 mbar to give 23.42 g of product hydrochloride VII.

The 23.42 g crude product hydrochloride VII was extracted with methyl tertiary butyl ether (230 ml) and a mixture consisting of NaOH 1M (80 ml) and water (40 ml). The organic phase was separated, dried over sodium sulfate and filtered. The filter cake was washed with methyl tertiary butyl ether (50 ml). The colorless filtrate was concentrated at 40° C. under reduced pressure to give 21.2 g of product VIII (68% yield, >99a % by HPLC).

Alternative B 1-(3,4-dichlorophenyl)-2-methylenepentan-1-one IV (40 g, 143 mmol, Eq: 1.00) was dissolved in THF (120 ml). Trifluoro acetic acid (833 mg, 559 µl, 7.16 mmol, Eq: 0.05) was added and the solution was heated to 50° C. A solution of N-benzyl-1-methoxy-N-((trimethylsilyl)methyl)-methanamine VI-2 (44.2 g, 179 mmol, Eq: 1.25) in tetrahydrofuran (THF) (40.0 ml) was added over 1 h. The reaction mixture was stirred 1 h at 50° C. and concentrated at 40° C. under reduced pressure. The oily residue was dissolved in ethyl acetate (200 ml). 2 M aqueous HCl (93.0 ml) and half saturated aqueous NaCl solution (50 ml) were added. The aqueous phase was separated, extracted with ethyl acetate (50 ml) and discarded. The organic phases were combined and washed with 2 M aqueous NaOH (79 ml). The basic aqueous phase was separated, extracted with ethyl acetate (50 ml) and discarded. The organic phases were washed with deionized water (50 ml), combined and concentrated under reduced pressure to ca 120 mL. 2.2 M HCl solution in ethyl acetate (71.6 ml, 157 mmol, Eq: 1.1) was added. After a few minutes, the product started to crystallize. After 30 min at RT, heptane (380 ml) was added over 30 min. The suspension was cooled to 0-2° C. After 1 h, the suspension was filtered. The filter cake was washed with heptane (100 ml) and dried at 50° C. under reduced pressure to give 33.9 g of the pyrrolidine hydrochloride VII.

33.7 g pyrrolidine hydrochloride was suspended in ethyl acetate (100 ml). 10% aqueous sodium carbonate 10% (50 ml) were added. After 30 min stirring at RT, the aqueous phases was separated, extracted with ethyl acetate (50 ml) and discarded. The organic phases were washed with half saturated aqueous sodium chloride (50 ml). The combined organic phases were dried over magnesium sulfate, filtered and concentrated under reduced pressure to give 29.8 g of the desired product VIII as an oil (54% yield).

Resolution of (1-Benzyl-3-propyl-pyrrolidin-3-yl)-(3,4-dichloro-phenyl)-methanone VIII

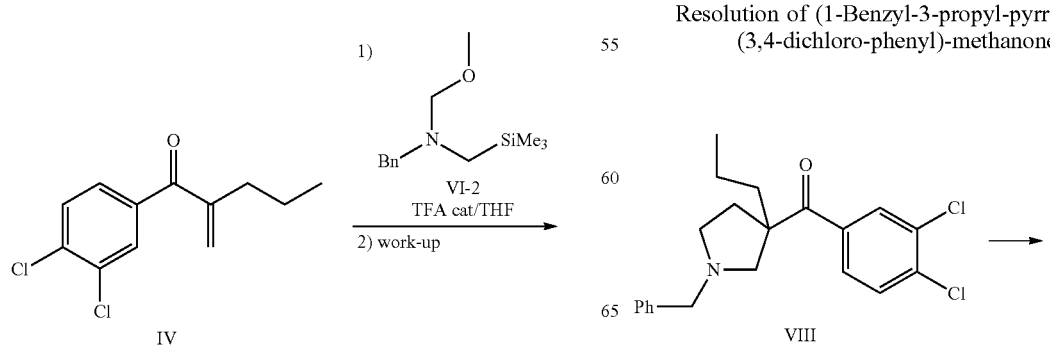

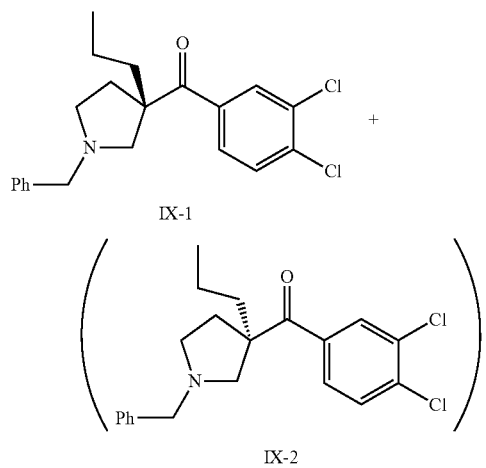

HPLC

The enantiomers can, for example, be separated on polysaccharide-based chiral stationary phases. The separation can be performed for example (but not limited to) on phases of type Chiralpak AD, Chiralpak IA or Chiralpak AY (preferably AD and IA, even preferably AD), using a mobile phase consisting of a mixture of heptane or hexane (preferentially heptane) with an appropriate alcohol like for example ethanol, in the appropriate ratio and at an appropriate temperature, optionally in the presence of a modifier like diethylamine. 24 g of N-Bn-pyrrolidine VIII were separated by preparative chiral HPLC (Chiralpak AD, heptane/ethanol 60:40 v/v, 40° C.) to give 10.8 g of the desired enantiomer IX-1 (first eluting) in >99% e.e. Optical rotation: $[\alpha]_D^{20}$=30.45 (c=1.005 in chloroform).

SFC

The enantiomers can, for example, be separated on polysaccharide-based chiral stationary phases. The separation can be performed for example (but not limited to) on phases of type Chiralpak IA, Chiralpak AD or Chiralpak AY (preferably Chiralpak AD) using a mobile phase consisting of a mixture of carbon dioxide with an appropriate alcohol, for example ethanol, in the appropriate solvent ratio and optionally in the presence of a modifier like for example diethylamine. 3 g Bn-pyrrolidine was separated by stacked injections on a Chiralpak AD-H column, carbon dioxide/ethanol 80:20, 40° C. to give 1.1 g of the desired enantiomer (first eluting).

Synthesis of (3,4-Dichloro-phenyl)-((S)-3-propyl-pyrrolidin-3-yl)-methanone hydrochloride

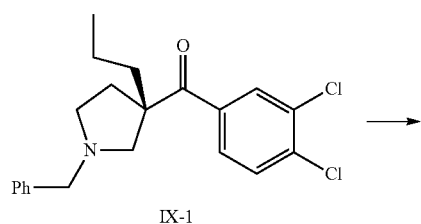

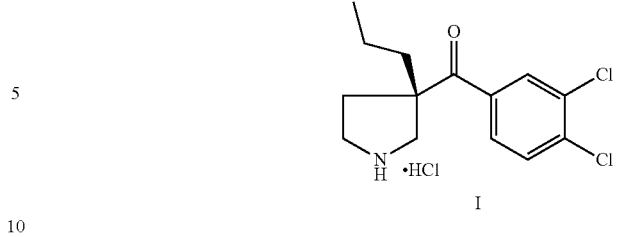

(S)-(1-benzyl-3-propylpyrrolidin-3-yl)(3,4-dichlorophenyl)methanone IX-1 (5 g, 13.3 mmol, Eq: 1.00) was dissolved in dichloromethane (30 ml). The light yellow solution was cooled down to 0-5° C. and N-Ethyldiisopropylamine (172 mg, 226 µl, 1.33 mmol, Eq: 0.1) was added. 1-chloroethyl chloroformate (2.28 g, 1.74 ml, 15.9 mmol, Eq: 1.2) was added dropwise keeping the temperature between 0-5° C. The reaction was warmed to RT over ca 30 min and stirred 1 h at RT (IPC by HPLC). Methanol (25 ml) was added and the light yellow solution was heated to 40° C. for 40 min (IPC by HPLC). The reaction mixture was concentrated under reduced pressure 40° C./600-15 mbar to give 5.48 g of crude product. Ethyl acetate (30.0 ml) was added and the suspension was heated to 50° C. A solution of water (239 mg, 239 µl, 13.3 mmol, Eq: 1.0) in ethyl acetate (35 ml) was added over 10 min. The white suspension was stirred 1 h at 50° C. and cooled to RT over 1.5 h. After 2 h at RT, the suspension was filtered. The filter cake was washed twice with ethyl acetate (10 ml) and dried under reduced pressure (40° C./15 mbar) to give 4.02 g of product I (93% yield) as quarterhydrate.

Synthesis of (3,4-Dichloro-phenyl)-(3-propyl-pyrrolidin-3-yl)-methanone hydrochloride

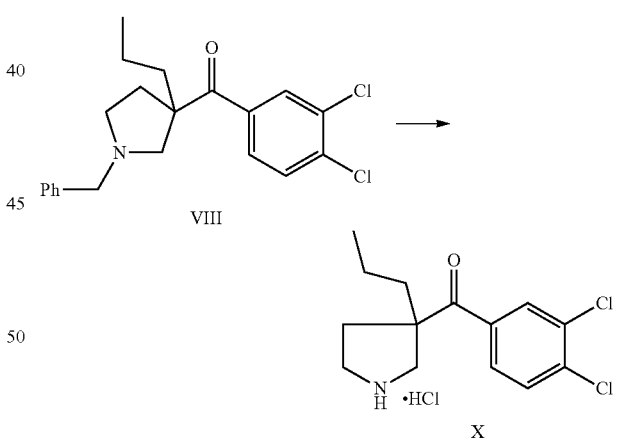

(1-benzyl-3-propylpyrrolidin-3-yl)(3,4-dichlorophenyl)methanone VIII (2 g, 5.31 mmol, Eq: 1.00) was dissolved in dichloromethane (12.0 ml). N-Ethyldiisopropylamine (137 mg, 181 µl, 1.06 mmol, Eq: 0.2) was added and the solution was cooled to 0° C. to 5° C. 1-chloroethyl chloroformate (912 mg, 696 µl, 6.38 mmol, Eq: 1.2) was added at 0° C.-5° C. After 50 min at 0-5° C., the reaction was warmed to 25° C. and stirred at RT. After 30 min at RT, methanol (5 ml) was added and the solution was heated at 35° C. overnight. The solution was solvent exchanged to ethyl acetate (with ca 40 ml ethyl acetate) to ca 30 g reaction mass, during which crystallization started. The suspension was stirred 2 h at RT, cooled to 0-5° C. for 1 h and filtered. The filter cake was washed with ethyl acetate (9.00 g, 10 ml) and dried at 50° C./10 mbar to give 1.48 g of product as an off white powder (86% yield).

Recrystallization of Compound Formula I Quaterhydrate 54.4 g of quarterhydrate of (I) were dissolved at RT in 550 mL ethanol. The solution was filtered and concentrated under reduce pressure at 60° C. to a volume of 140 mL. The volume was adjusted to 550 mL by addition of ethyl acetate. The rest of ethanol was solvent exchanged to ethyl acetate (Tj=60° C./reduced pressure). 55 mL ethanol were added to the resulting suspension at Tr=60° C. upon which a solution was obtained. 1.5 mL water was then added and the solution was slowly cooled to RT during which crystallization occurred. After stirring at RT overnight, the suspension was cooled to 0-5° C. for 1 h and filtered. The filter cake was washed with a mixture of 50 mL ethyl acetate and 5 mL ethanol followed by two washes with 50 mL ethyl acetate. The crystals were dried at 50° C. overnight under reduced pressure to give 48.9 g of quarterhydrate of (I) as a white powder.

Alternatively, the 55 mL ethanol and 1.5 mL water can be added together as a solution.

Transformation of Compound of Formula I Anhydrate to the Quaterhydrate Form

Compound of formula I (40 g, 124 mmol, Eq: 1.00, anhydrate) was suspended in a mixture of ethyl acetate (AcOEt) (340 ml), ethanol (36 ml) and water (0.6 ml) at room temperature. The suspension was heated to 40° C. and a mixture consisting of AcOEt (20 mL), ethanol (0.5 ml) and water (0.6 mL) was added over 1 h. The suspension was cooled to RT over 1 h. After stirring overnight at RT, the suspension was cooled to 2-3 h at 0-5° C., filtered and washed with a cold (0-5° C.) mixture of AcOEt (55 mL), ethanol (5 mL) and water (0.5 mL). The filter cake was dried at 50° C. under reduced pressure to give 38 g of product as quarterhydrate (1.5% water).

Chiral Separation of Compound of Formula X

The enantiomers can be separated on polysaccharide-based chiral stationary phases. The separation can be performed for example (but not limited to) on phases of type Chiralpak AD or Chiralpak AY using a mobile phase consisting of a mixture of $CO_2$ with an appropriate alcohol selected, for example, from methanol (MeOH), ethanol (EtOH), isopropanol (iPrOH) or a mixture thereof, in the appropriate solvent ratio and in the presence of a modifier like for example diethylamine. Chiralpak AD and Chiralpak AY are preferred stationary phases type, even more preferred is the Chiralpak AY. Preferred alcohols are MeOH and EtOH.

Resolution to (3,4-Dichloro-phenyl)-(3-(S)-propyl-pyrrolidin-3-yl)-methanone D-tartrate (3,4-dichlorophenyl)(3-propylpyrrolidin-3-yl)methanone hydrochloride X (10 g, 31.0 mmol, Eq: 1.00) and (2S,3S)-2,3-dihydroxysuccinic acid (2.4 g, 15.8 mmol, Eq: 0.51) were dissolved in deionized water (40.0 ml) and methanol (10.0 ml). The solution was heated to 60° C. 4 M aqueous sodium hydroxide (3.76 ml, 15.0 mmol, Eq: 0.485) were added. The solution was stirred at 60° C. for ca 30 min during which crystallization started. The suspension was slowly cooled to 50° C. and stirred at that temperature for 1 h then cooled to RT over 2 h and stirred overnight at RT. The suspension was cooled to 0-2° C. After 2 h at 0-2° C., the suspension was filtered, washed with cold (0-5° C.) deionized water (10.0 ml) and dried under reduced pressure (10 mbar/50° C.) to give 4.7 g of the title compound X-TAR in 98.5:1.5 d.r.

Resolution to (3,4-Dichloro-phenyl)-(3-(S)-propyl-pyrrolidin-3-yl)-methanone D-tartaric acid salt (3,4-dichlorophenyl)(3-propylpyrrolidin-3-yl)methanone hydrochloride X (87.5 g, 258 mmol, Equivalents: 1.00) and (2S,3S)-2,3-dihydroxysuccinic acid (19.9 g, 131 mmol, Equivalents: 0.510) were charged in the reactor. Deionized water (350 ml) and methanol (87.5 ml) were added. The solution was heated to 60° C. 4 M aqueous sodium hydroxide (32.9 ml, 132 mmol, Equivalents: 0.511) were added. The solution was seeded and slowly cooled to 50° C. After 1 h stirring at 50° C., the white suspension was cooled to room temperature over 2 h. The suspension was stirred overnight at room temperature, cooled to 0°-2° C. for 2 h and filtered. The filter cake was washed with cold (0-5° C.) deionized water (87.5 ml) and dried at 50° C. under reduced pressure to give 42 g of D-tartaric acid salt X-TAR (ca 95:5 d.r.).

Recrystallization (3,4-Dichloro-phenyl)-(3-(S)-propyl-pyrrolidin-3-yl)-methanone D-tartaric acid salt 40.0 g salt X-TAR were charged in the reactor followed by deionized water (480 ml). The suspension was heated to 95° C. The resulting solution was cooled to room temperature over 3 h (crystallization started around 80° C.) then cooled to 0-5-° C. for 2 h. The suspension was filtered. The filter cake was washed with cold (0-5° C.) deionized water (87.5 ml) and dried at 50° C. under reduced pressure to give 37 g of tartaric acid salt X-TAR (99.7:0.3 d.r.).

Synthesis of (3,4-Dichloro-phenyl)-(3-(S)-propyl-pyrrolidin-3-yl)-methanonehydrochloride I Alternative A (S)-(3,4-dichlorophenyl)(3-propylpyrrolidin-3-yl)methanone (2S,3S)-2,3-dihydroxysuccinate X-TAR (20 g, 45.7 mmol, Equivalents: 1.00) was suspended in methyl tert-butyl ether (150 ml) and treated with 2M aqueous sodium hydroxide (48.0 ml, 96.0 mmol, Equivalents: 2.1). The organic phase was separated and washed twice with water (50 ml). Ethanol (150 ml) was added to the organic extract followed by 37% hydrochloric acid (4.01 ml, 48.0 mmol, Equivalents: 1.05). The solution was concentrated under reduced pressure (300 mbar/60° C.) to ca 100 mL and was polish filtered. Ethyl acetate (300 ml) was added and the solution was seeded. The resulting mixture was concentrated under reduced pressure (300 mbar/60° C.) to a white suspension (ca 150 g). A solution of water (412 mg, 412 µl, 22.9 mmol, Equivalents: 0.5) in ethanol (15 ml) was added at room temperature. The suspension was stirred at room temperature overnight and cooled to 0° C. for 1 h. The suspension was filtered and the filter cake was washed with cold (0° C.) ethyl acetate (60 ml). The crystals were dried at 50° C. under reduced pressure to give 14.3 g of product I as quarterhydrate (96% yield).

Alternative B (S)-(3,4-dichlorophenyl)(3-propylpyrrolidin-3-yl)methanone (2S,3S)-2,3-dihydroxysuccinate X-TAR (5 g, 11.4 mmol, Equivalents: 1.00) were dissolved in 5 M hydrochloric acid in ethanol (12.5 ml, 62.5 mmol, Equivalents: 5.47). The solution was stirred overnight at room temperature. The solution was polish filtered. The filter was washed with ethanol (10 mL). Ethyl acetate (150 ml) was added to the filtrate, followed by seed crystals. The mixture was concentrated under reduced pressure (50° C./100 mbar) to ca 40 mL. A solution of water (206 mg, 206 µl, 11.4 mmol, Equivalents: 1.00) in ethyl acetate (20 mL) was added at room temperature. The suspension was stirred at room temperature overnight, cooled to 0° C. for 2 h and filtered. The filter cake was washed with cold (0° C.) ethyl acetate (20 mL). The crystals were dried at 50° C. under reduced pressure to give 3.3 g of product I as quarterhydrate (89% yield).

Alternative C (S)-(3,4-dichlorophenyl)(3-propylpyrrolidin-3-yl)methanone (2S,3S)-2,3-dihydroxysuccinate X-TAR (5 g, 11.4 mmol, Equivalents: 1.00) was dissolved in 1.25 M HCl$_g$ in ethanol (20.1 ml, 25.1 mmol, Equivalents: 2.2). The solution was stirred overnight at room temperature, was dried azeotropically with ethanol and was polish filtered. The filtrate was solvent exchanged to ethyl acetate (to ca 40 ml volume) and seeded. A solution of water (206 mg, 206 µl, 11.4 mmol, Equivalents: 1.00) in ethyl acetate (20.0 ml) was added. The suspension was stirred 4 h at room temperature then 2 h at 0° C. and filtered. The filter cake was washed with cold (0° C.) ethyl acetate (20.0 ml) and dried at 50° C. under reduced pressure to give 3.6 g of product I as quarterhydrate.

Synthesis of 1-(3,4-Dichloro-phenyl)-pentan-1-one (II*)

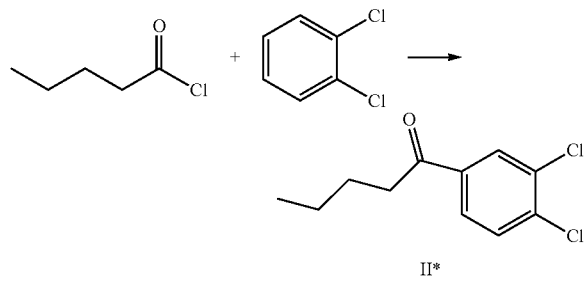

Aluminum chloride (12.4 g, 93.3 mmol, Equivalents: 1.5) was charged in the reactor followed by 1,2-dichlorobenzene (27.4 g, 21.0 ml, 187 mmol, Equivalents: 3). The suspension was heated to 80° C. in 10 min and pentanoyl chloride (7.5 g, 7.58 ml, 62.2 mmol, Equivalents: 1.00) was added dropwise over 30 min. The reaction mixture went from a yellow suspension to an orange/brown viscous solution. After 5 h reaction at 80° C. the deep orange/brown reaction mixture was cooled to 25° C. and stirred at 25° C. overnight. The reaction mixture was poured onto a mixture of n-heptane (68.4 g, 100 ml) and water/ice 50:50 (100 g, 100 ml). The organic phase was separated and washed with water (50.0 g, 50 ml) then with 5% aqueous sodium bicarbonate (50 ml) and finally with water (50.0 g, 50 ml) The organic phase was dried azeotropically (60° C./ca 150 mbar) with n-heptane (205 g, 300 ml) to give 28 g of crude product as an orange oil (ca 96:4 Product/2,3-dichlorovalerophenone isomer). The crude oil was dissolved in n-heptane (27.4 g, 40 ml) and the solution was cooled to −20° C. for 2 h. The suspension was filtered. The filter was washed with cold n-heptane (10.3 g, 15 ml) and dried at 35° C./10 mbar to give 8.8 g of the title product (>98a % GC, isomer<1%). The product can be obtained in >99% purity.

Synthesis of 1-(3,4-Dichloro-phenyl)-2-methylene-pentan-1-one (IV*)

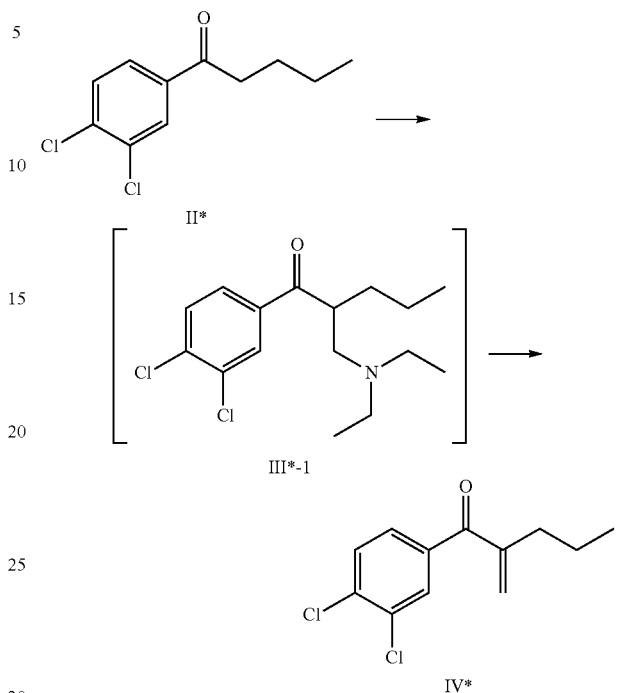

Alternative A 1-(3,4-dichlorophenyl)pentan-1-one II* (15 g, 63.0 mmol, equivalents: 1.00) and paraformaldehyde (3.58 g, 113 mmol, equivalents: 1.8) were charged in the reactor followed by heptane (30.0 ml). Temperature was set at 25° C. Diethylamine (8.84 g, 12.5 ml, 120 mmol, equivalents: 1.9) was added. Acetic acid (11.4 g, 10.9 ml, 189 mmol, equivalents: 3) was slowly added and the reaction mixture was heated to 60° C. After 17 h reaction (<2% starting material), deionized water (30.0 ml) was added and the reaction mixture was heated to 80° C. After completion of the reaction (usually <5 h, <1% intermediate III*-1 by HPLC), the reaction mixture was cooled to room temperature. The organic phase was separated and washed twice with 20 mL deionized water. The organic phase was concentrated under reduced pressure and dried azeotropically with heptane to give 15.32 g of the olefin IV* as orange oil (96% yield corrected for 96a % purity by HPLC).

Alternative B 1-(3,4-dichlorophenyl)pentan-1-one II* (15 g, 63.0 mmol, equivalents: 1.00) and paraformaldehyde (3.58 g, 113 mmol, equivalents 1.8) were charged in the reactor followed by heptane (20.5 g, 30.0 ml). Temperature was set to 25° C. Acetic acid (11.4 g, 10.9 ml, 189 mmol, equivalents: 3) was added followed by diethylamine (8.84 g, 12.5 ml, 120 mmol, equivalents: 1.9). The reaction mixture was heated to 60° C. After 17 h30 reaction (<2% starting material), deionized water (30.0 ml) was added and the reaction mixture was heated to 80° C. After completion of the reaction (usually <5 h; <1% intermediate II*-1 by HPLC), the reaction mixture was cooled to room temperature and polish filtered. The aqueous phase was separated and discarded. The organic phase was washed twice with 20 mL deionized water and once with 10 mL 25% aqueous sodium chloride. The organic phase was concentrated under reduced pressure and dried azeotropically with heptane to give 15.53 g of the desired product IV* as orange oil (99% yield, corrected for 97.7% purity).

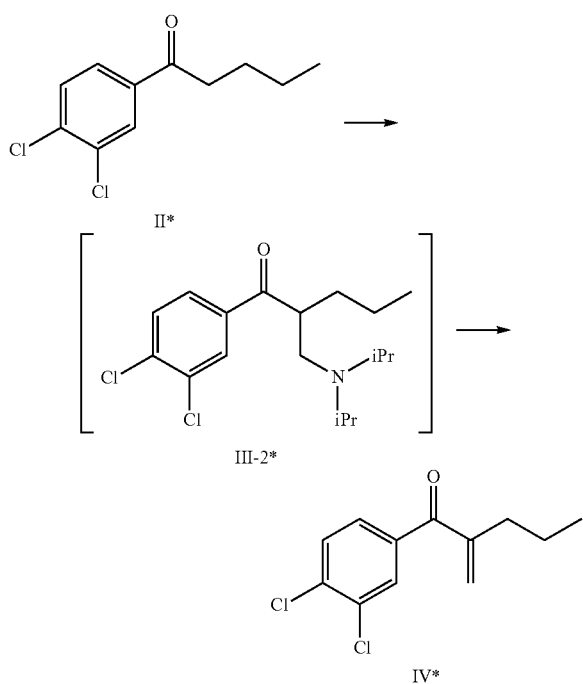

Alternative C 1-(3,4-dichlorophenyl)pentan-1-one II* (15 g, 63.0 mmol, equivalents: 1.00) was charged in the reactor followed by tetrahydrofuran (THF) (45.0 ml). 37.5% aqueous formaldehyde (8.57 g, 7.91 ml, 107 mmol, equivalents: 1.7) was added followed by diisopropylamine (11.6 g, 16.2 ml, 113 mmol, equivalents: 1.8). Acetic acid (7.6 g, 7.24 ml, 126 mmol, equivalents: 2) was added and the reaction mixture was heated to 60° C. overnight (IPC by HPLC). After 18 hrs reaction, the reaction mixture was cooled to RT. Water (15 mL) and heptane (40 mL) were added. The tetrahydrofuran was removed at the rotary evaporator (250 mbar/50° C.). The organic phase was separated and washed twice with water (40 ml). The crude product solution was dried azeotropically under reduced pressure (ca 150 mbar/60° C.) with heptane and concentrated to give 15.53 g of product IV* as an orange oil (93% yield corrected for 92a % purity by HPLC).

Further Alternative Methods to Obtain the Olefin IV*

The reaction can be performed in organic solvents like acetic acid, toluene, tetrahydrofuran, 2-Me-tetrahydrofuran and heptane with secondary amines like morpholine, diethylamine, diisopropylamine in the presence of acids like hydrochloric acid, acetic acid, 2-ethylhexanoic acid, pivalic acid, in particular acetic acid. The source of formaldehyde can be paraformaldehyde or aqueous formaldehyde (typically of 30-40% concentration). Particular solvents are tetrahydrofuran and heptane whereas particularly bases are diisopropylamine and diethylamine. Further alternative solvents can be tetrahydrofuran, Me-tetrahydrofuran, heptane or toluene, particular are tetrahydrofuran and heptane. An excess of formaldehyde source is used, typically between 1 and 3 equivalents, in particular between 1.5 and 2 equivalents. The reaction is usually conducted by heating between 50-120° C., in particular between 60-90° C. An excess of base and acid is usually used.

Synthesis of 3-(3,4-Dichloro-benzoyl)-3-propyl-pyrrolidine-1-carboxylic acid tert-butyl ester VIII*

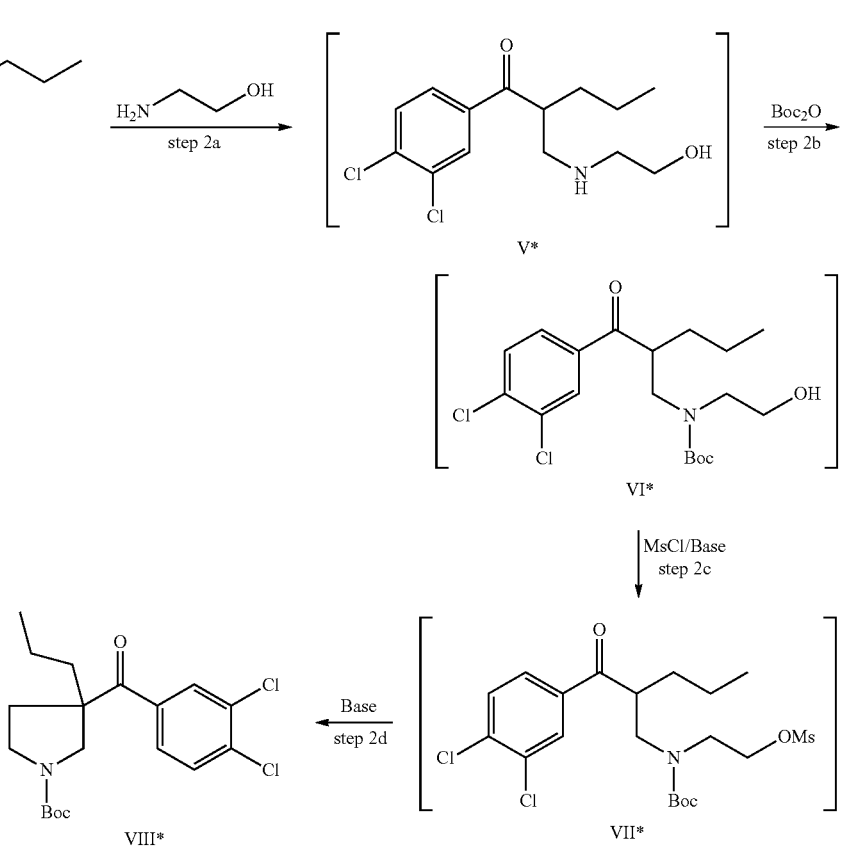

Alternative A

Step 2a Michael Addition 1-(3,4-dichlorophenyl)-2-methylenepentan-1-one IV* (100 g, 394 mmol, Equivalents: 1.00) was dissolved in tetrahydrofuran (150 ml). A solution of 2-aminoethanol (26.7 g, 26.3 ml, 433 mmol, Equivalents: 1.10) in tetrahydrofuran (150 ml) was added dropwise over 15 min (Tr 20-30° C.). The solution was stirred overnight at room temperature (IPC by HPLC). Intermediate V can isolated following work-up known by the person skilled in the art, or can be introduced directly in the next step Step 2b Boc Protection A solution of di-tert-butyl dicarbonate (95.5 g, 433 mmol, Equivalents: 1.10) in tetrahydrofuran (1.0 l) was added to the Michael addition product V solution from step 2a. The reaction mixture was stirred at room temperature for 1 h (IPC by HPLC). Intermediate VI* can be isolated following work-up known by the person skilled in the art, for instance after an aqueous work-up.

Step 2c Mesylation

The crude solution of VI* from step 2b was cooled to 0-5° C. N-ethyldiisopropylamine (67.5 g, 89.0 ml, 512 mmol, Equivalents: 1.30) was added. A solution of methanesulfonyl chloride (58.6 g, 39.8 ml, 512 mmol, Equivalents: 1.30) in toluene (30.0 ml) was added dropwise over 30 min. The addition funnel was washed with toluene (30.0 ml). The reaction mixture was stirred 2 h at 0-5° C. (IPC by HPLC). Intermediate VII* can be isolated after aqueous work-up, but as the isolated compound exhibit a moderate stability it can be introduced in the next step without isolation.

The decomposition product was identified as being the following oxazolidinone:

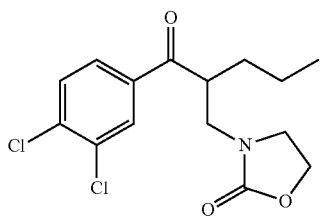 [SMILES: CCCC(CN1CCOC1=O)C(=O)c1ccc(Cl)c(Cl)c1]

Alternatively, other bases than N-ethyldiisopropylamine like triethylamine or tripropylamine can be used.

Step 2d Cyclization

A 35% sodium 2-methylbutan-2-olate solution in tetrahydrofuran (372 g, 1.18 mol, Equivalents: 3.0) diluted with tetrahydrofuran (125 ml) was added over 60 min to the solution of VII* from step 2c, keeping the temperature between 0-5° C. The reaction mixture was stirred 60 min at 0-5° C. (IPC by HPLC). Deionized water (500 ml) was added over 15 min keeping the temperature between 0-10° C. Toluene (750 ml) was added and the mixture was concentrated at 40° C./150 mbar to remove most of the tetrahydrofuran. 2M aqueous hydrochloric acid (500 ml) was added. The aqueous phase was separated, extracted with toluene (125 ml) and discarded. The organic phases were combined and washed with half saturated aqueous sodium bicarbonate (250 ml) and half saturated aqueous sodium chloride (250 ml). The organic phase was concentrated under reduced pressure at 45° C. to give 167.4 g of crude product as viscous oil (77% assay yield by quantitative HPLC).

Alternatively, other bases than sodium 2-methylbutan-2-olate like lithium tert-amyl oxide, potassium tert-amyloxide, sodium tert-butoxide, potassium tert-butoxide, lithium tert-butoxide or sodium methoxide can be used, in particular potassium tert-amyloxide, sodium tert-butoxide, potassium tert-butoxide, more particular potassium tert-amyloxide. The reaction is usually performed between −20° C. and 40° C., in particular between 0° C. and room temperature. The cyclization can also be conducted under biphasic conditions (in particular water/toluene mixtures) by using an aqueous hydroxide base like for example NaOH, in combination with a phase transfer catalyst for example tetrabutylamonium bromide (see alternative B). In this case the reaction can in particular be conducted between room temperature and 50° C., more particular between room temperature and 40° C., most particular at room temperature.

Alternative B

Step 2a Michael Addition 1-(3,4-dichlorophenyl)-2-methylenepentan-1-one IV* (30 g, 121 mmol, Equivalents: 1.00) was charged in the reactor and dissolved in tetrahydrofuran (45.0 ml). A solution of 2-aminoethanol (8.18 g, 8.06 ml, 133 mmol, Equivalents: 1.10) in tetrahydrofuran (45.0 ml) was added over 15 min at RT. The reaction mixture was stirred overnight at room temperature (IPC by HPLC).

Step 2b Boc Protection

A solution of di-tert-butyl dicarbonate (29.2 g, 133 mmol, Equivalents: 1.10) in toluene (60.0 ml) was added dropwise over 15 min at room temperature to the solution of V* from step 2a. The reaction mixture was stirred 1 h at room temperature (IPC by HPLC). Toluene (60.0 ml) was added and the tetrahydrofuran was removed by distillation under reduced pressure (40° C./120 mbar).

Step 2c Mesylation

The toluene solution of VI* from step 2b was cooled to 0-2° C. Triethylamine (15.9 g, 22.0 ml, 157 mmol, Equivalents: 1.30) was added. A solution of methanesulfonyl chloride (18.3 g, 12.4 ml, 157 mmol, Equivalents: 1.30) in toluene (15.0 ml) was added dropwise over 30 min keeping the temperature between 0-5° C. The reaction mixture was stirred >1 h at 0-5° C. (IPC by HPLC and GC).

Alternatively, other bases than triethylamine like N-ethyldiisopropylamine or tripropylamine can be used.

Step 2d Cyclization

32% aqueous sodium hydroxide (151 g, 112 ml, 1.21 mol, Equivalents: 10.00) was added to the reaction mixture of VII* from step 2c, followed by water (9.00 g, 9.00 ml) and tetrabutylamonium bromide (1.96 g, 6.03 mmol, Equivalents: 0.05). The biphasic reaction mixture was warmed to room temperature and stirred overnight (IPC by HPLC and GC). The organic phase was separated, washed 3 times with half saturated aqueous sodium chloride (120 mL), dried over MgSO$_4$ and concentrated under reduced pressure to give 49.1 g of the product VIII* (77% assay yield by quant HPLC). This product can be introduced into the next reaction step.

Synthesis of (3,4-Dichloro-phenyl)-(3-propyl-pyrrolidin-3-yl)-methanone hydrochloride IX*

The Boc-deprotection can be performed by standard methods known by the person skilled in the art, such as by a controlled addition of the Boc-pyrrolidine solution to a hot aqueous HCl/toluene mixture, allowing the rapid deprotection together with an easy control of gas evolution. The reaction can be performed between 50-100° C., in particular between 50-80° C., more particularly at 60° C.±3° C. Concentrated HCl, in particular >25%, more particular 30%, most particular >35% is used. After reaction completion, the solution is azeotroped to remove water and excess HCl. It is preferable to work <100° C. to avoid degradation products. The product is then crystallized.

The crude tert-butyl 3-(3,4-dichlorobenzoyl)-3-propylpyrrolidine-1-carboxylate VIII* (167 g, 303 mmol, Equivalents: 1.00) from previous step was dissolved in toluene (251 ml) and added over 30 min to well stirred hot mixture (60° C.) of 37% aqueous hydrochloric acid (119 g, 101 ml, 1.21 mol, Equivalents: 4.0) and toluene (501 ml). After 1 h at 60° C. (IPC by HPLC), toluene (1.01 l) was added and the mixture was dried azeotropically at 110 mbar/60° C. (removal of water and excess hydrochloric acid). The toluene solution was concentrated to ca 215 g and ethyl acetate (946 ml) was added. The orange solution was seeded and the product started to crystallize. The suspension was slowly cooled to room temperature. After stirring >15 h, the suspension was cooled to 0° C. for 2 h and filtered. The filter cake was washed with cold (0° C.) ethyl acetate (200 ml) and dried at 50° C. under reduced pressure to give 91.0 g of product IX* (89% yield corrected for 97a % purity by HPLC, residual sodium chloride and solvents).

If not available, seed crystals can be obtained by cooling an aliquot of the solution to 0° C. and initiating the crystallization by scratching. This can be returned to the main reaction mixture to initiate crystallization.

Resolution to (3,4-Dichloro-phenyl)-(3-(S)-propyl-pyrrolidin-3-yl)-methanone D tartrate X*

(3,4-dichlorophenyl)(3-propylpyrrolidin-3-yl)methanone hydrochloride (10 g, 31.0 mmol, Eq: 1.00) and (2S,3S)-2,3-dihydroxysuccinic acid (2.4 g, 15.8 mmol, Eq: 0.51) were dissolved in deionized water (40.0 ml) and methanol (10.0 ml). The solution was heated to 60° C. 4 M aqueous sodium hydroxide (3.76 ml, 15.0 mmol, Eq: 0.485) were added. The solution was stirred at 60° C. for ca 30 min during which crystallization started. The suspension was slowly cooled to 50° C. and stirred at that temperature for 1 h then cooled to RT over 2 h and stirred overnight at RT. The suspension was cooled to 0-2° C. After 2 h at 0-2° C., the suspension was filtered, washed with cold (0-5° C.) deionized water (10.0 ml) and dried under reduced pressure (10 mbar/50° C.) to give 4.7 g of the title compound in 98.5:1.5 d.r.

Resolution to (3,4-Dichloro-phenyl)-(3-(S)-propyl-pyrrolidin-3-yl)-methanone D tartrate X*

(3,4-dichlorophenyl)(3-propylpyrrolidin-3-yl)methanone hydrochloride IX* (87.5 g, 258 mmol, Equivalents: 1.00) and (2S,3S)-2,3-dihydroxysuccinic acid (19.9 g, 131 mmol, Equivalents: 0.510) were charged in the reactor. Deionized water (350 ml) and methanol (87.5 ml) were added. The solution was heated to 60° C. 4 M aqueous sodium hydroxide (32.9 ml, 132 mmol, Equivalents: 0.511) were added. The solution was seeded and slowly cooled to 50° C. After 1 h stirring at 50° C., the white suspension was cooled to room temperature over 2 h. The suspension was stirred overnight at room temperature, cooled to 0°-2° C. for 2 h and filtered. The filter cake was washed with cold (0-5° C.) deionized water (87.5 ml) and dried at 50° C. under reduced pressure to give 42 g of D-tartaric acid salt X* (ca 95:5 d.r.).
Recrystallization of X*
40.0 g salt X* were charged in the reactor followed by deionized water (480 ml). The suspension was heated to 95° C. The resulting solution was cooled to room temperature over 3 h (crystallization started around 80° C.) then cooled to 0-5-° C. for 2 h. The suspension was filtered. The filter cake was washed with cold (0-5° C.) deionized water (87.5 ml) and dried at 50° C. under reduced pressure to give 37 g of tartaric acid salt X* (99.7:0.3 d.r.).

Synthesis of (3,4-Dichloro-phenyl)-(3-(S)-propyl-pyrrolidin-3-yl)-methanonehydrochloride I Alternative A (S)-(3,4-dichlorophenyl)(3-propylpyrrolidin-3-yl)methanone (2S,3S)-2,3-dihydroxysuccinate X* (20 g, 45.7 mmol, Equivalents: 1.00) was suspended in methyl tert-butyl ether (150 ml) and treated with 2M aqueous sodium hydroxide (48.0 ml, 96.0 mmol, Equivalents: 2.1). The organic phase was separated and washed twice with water (50 ml). Ethanol (150 ml) was added to the organic extract followed by 37% hydrochloric acid (4.01 ml, 48.0 mmol, Equivalents: 1.05). The solution was concentrated under reduced pressure (300 mbar/60° C.) to ca 100 mL and was polish filtered. Ethyl acetate (300 ml) was added and the solution was seeded. The resulting mixture was concentrated under reduced pressure (300 mbar/60° C.) to a white suspension (ca 150 g). A solution of water (412 mg, 412 µl, 22.9 mmol, Equivalents: 0.5) in ethanol (15 ml) was added at room temperature. The suspension was stirred at room temperature overnight and cooled to 0° C. for 1 h. The suspension was filtered and the filter cake was washed with cold (0° C.) ethyl acetate (60 ml). The crystals were dried at 50° C. under reduced pressure to give 14.3 g of product I as quarterhydrate (96% yield).

Alternative B (S)-(3,4-dichlorophenyl)(3-propylpyrrolidin-3-yl)methanone (2S,3S)-2,3-dihydroxysuccinate X* (5 g, 11.4 mmol, Equivalents: 1.00) were dissolved in 5 M hydrochloric acid in ethanol (12.5 ml, 62.5 mmol, Equivalents: 5.47). The solution was stirred overnight at room temperature. The solution was polish filtered. The filter was washed with ethanol (10 mL). Ethyl acetate (150 ml) was added to the filtrate, followed by seed crystals. The mixture was concentrated under reduced pressure (50° C./100 mbar) to ca 40 mL. A solution of water (206 mg, 206 µl, 11.4 mmol, Equivalents: 1.00) in ethyl acetate (20 mL) was added at room temperature. The suspension was stirred at room temperature overnight, cooled to 0° C. for 2 h and filtered. The filter cake was washed with cold (0° C.) ethyl acetate (20 mL). The crystals were dried at 50° C. under reduced pressure to give 3.3 g of product I as quarterhydrate (89% yield).

Alternative C (S)-(3,4-dichlorophenyl)(3-propylpyrrolidin-3-yl)methanone (2S,3S)-2,3-dihydroxysuccinate (5 g, 11.4 mmol, Equivalents: 1.00) was dissolved in 1.25 M $HCl_g$ in ethanol (20.1 ml, 25.1 mmol, Equivalents: 2.2). The solution was stirred overnight at room temperature, was dried azeotropically with ethanol and was polish filtered. The filtrate was solvent exchanged to ethyl acetate (to ca 40 ml volume) and seeded. A solution of water (206 mg, 206 µl, 11.4 mmol, Equivalents: 1.00) in ethyl acetate (20.0 ml) was added. The suspension was stirred 4 h at room temperature then 2 h at 0° C. and filtered. The filter cake was washed with cold (0° C.) ethyl acetate (20.0 ml) and dried at 50° C. under reduced pressure to give 3.6 g of product I as quarterhydrate.

Resolution of 3-(3,4-Dichloro-benzoyl)-3-propyl-pyrrolidine-1-carboxylic acid tert-butyl ester VIII*

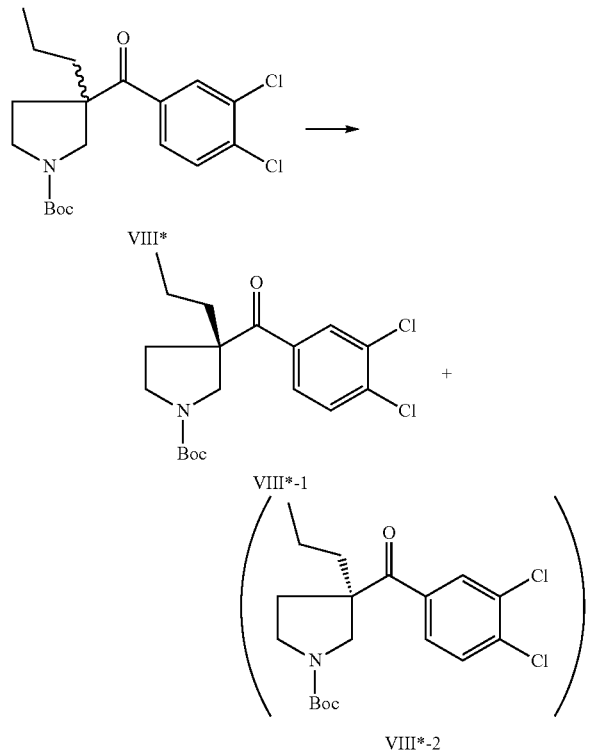

Alternative A: Chiral Supercritical Fluid Chromatography (SFC)

VIII* can be resolved on polysaccharide-based chiral stationary phases. The separation can be performed for example, but not limited to, on phases of type Chiralpak IA, Chiralpak IC, Chiralpak AD and Chiralpak AY, using a mobile phase consisting of a mixture of carbon dioxide ($CO_2$) with an appropriate alcohol selected, for example, from methanol (MeOH), ethanol (EtOH), isopropanol (iPrOH) or a mixture thereof, in the appropriate solvent ratio and optionally in the presence of a modifier like for example diethylamine. Chiralpak AD and Chiralpak AY are preferred stationary phases type, even more preferred is the Chiralpak AY. 4.5 g Boc-pyrrolidine VIII* was separated by stacked injections on a Chiralpak AD-H column, $CO_2$/EtOH 90:10, 30° C. to give 1.54 g of the desired enantiomer VIII*-1 (first eluting).

Alternative B: Chiral High Performance Liquid Chromatography (HPLC)

The enantiomers can, for example, be separated on polysaccharide-based chiral stationary phases. The separation can be performed for example (but not limited to) on phases of type Chiralpak IA, Chiralpak IC, Chiralpak AD and Chiralpak AY using a mobile phase consisting of a mixture of heptane or hexane (preferentially heptane) with an appropriate alcohol selected from EtOH or iPrOH in the appropriate ratio and at an appropriate temperature. Chiralpak AD and Chiralpak AY are preferred stationary phases type, even more preferred is the Chiralpak AY. The Reprosil Chiral NR stationary phase is also an option.

10 g crude VIII* (ca 70% m/m purity, crude material after cyclization process) were first purified by flash chromatography (heptane/ethyl acetate gradient, $SiO_2$) to give 6.7 g of VIII* (96a % purity by HPLC). The 6.7 g racemate were separated on a Reprosil Chiral NR stationary phase with 85:15 heptane/iPrOH mobile phase at 40° C. to give 2.58 g of the desired enantiomer (first eluting) in >99% e.e.

Boc-Deprotection of VIII*-1

12 M HCl (210 mL, 3.75 equiv.) was added to the Boc-ketone VIII*-1 (260 g, 1 equiv.) dissolved in toluene (2.1 L) at room temperature. A slight exotherm to about 25° C. was seen. This mixture was slowly heated to about 50° C. Once the reaction is judged complete (by TLC and by HPLC), the biphasic solvent mixture is removed by vacuum distillation to a bath temperature of about 75° C. until the toluene distillate no longer contains significant amounts of water. The residue was then dissolved in about 2.5 volumes of methanol and polish filtered through a medium glass frit. The methanol is then displaced with toluene first under vacuum and then by atmospheric distillation to an internal temperature of about 76° C., and about 6-8 volumes of toluene. Crystals formed at about 63° C. on cooling. The mixture was left slowly cooling overnight. The crystals were collected by filtration onto a course glass frit. The crystals were air dried under house vacuum for about 1.5 hours and then dried in a vacuum oven under full house vacuum with a nitrogen sweep at 80° C. for about 23 hours. This yielded 188 g of compound of formula I (99.8% purity).

Recrystallization of Compound Formula I Quarterhydrate 54.4 g of quarterhydrate of (I) were dissolved at RT in 550 mL ethanol. The solution was filtered and concentrated under reduce pressure at 60° C. to a volume of 140 mL. The volume was adjusted to 550 mL by addition of ethyl acetate. The rest of ethanol was solvent exchanged to ethyl acetate (Tj=60° C./reduced pressure). 55 mL ethanol were added to the resulting suspension at Tr=60° C. upon which a solution was obtained. 1.5 mL water was then added and the solution was slowly cooled to RT during which crystallization occurred. After stirring at RT overnight, the suspension was cooled to 0-5° C. for 1 h and filtered. The filter cake was washed with a mixture of 50 mL ethyl acetate and 5 mL ethanol followed by two washes with 50 mL ethyl acetate. The crystals were dried at 50° C. overnight under reduced pressure to give 48.9 g of quarterhydrate of (I) as a white powder.

Alternatively, the 55 mL ethanol and 1.5 mL water can be added together as a solution.

Transformation of Compound of Formula I Anhydrate to the Quaterhydrate Form

Compound of formula I (40 g, 124 mmol, Eq: 1.00, anhydrate) was suspended in a mixture of ethyl acetate (340 ml), ethanol (36 ml) and water (0.6 ml) at room temperature. The suspension was heated to 40° C. and a mixture consisting of ethyl acetate (20 mL), ethanol (0.5 ml) and water (0.6 mL) was added over 1 h. The suspension was cooled to RT over 1 h. After stirring overnight at RT, the suspension was cooled to 2-3 h at 0-5° C., filtered and washed with a cold (0-5° C.) mixture of ethyl acetate (55 mL), ethanol (5 mL) and water (0.5 mL). The filter cake was dried at 50° C. under reduced pressure to give 38 g of product as quarterhydrate (1.5% water).

Chiral Separation of Compound of Formula IX*

The enantiomers can, for example, be separated on polysaccharide-based chiral stationary phases. The separation can be performed for example (but not limited to) on phases of type Chiralpak AD or Chiralpak AY using a mobile phase consisting of a mixture of $CO_2$ with an appropriate alcohol selected, for example, from MeOH, EtOH, iPrOH or a mixture thereof, in the appropriate solvent ratio and in the presence of a modifier like for example diethylamine. Chiralpak AD and Chiralpak AY are preferred stationary phases type, even more preferred is the Chiralpak AY. Preferred alcohols are MeOH and EtOH.

X-Ray Powder Diffraction

X-ray diffraction patterns were recorded at ambient conditions in transmission geometry with a STOE STADI P diffractometer (Cu Ka radiation, primary monochromator, position sensitive detector, angular range 3° to 42° 2Theta, approximately 60 minutes total measurement time). The samples were prepared and analyzed without further processing (e.g. grinding or sieving) of the substance.

The hydrochloride quarterhydrate of (3,4-Dichloro-phenyl)-((S)-3-propyl-pyrrolidin-3-yl)-methanone solid can be identified by as few as one characteristic peak in its powder X-ray diffraction pattern as shown in FIG. 1. Two-theta angle positions of characteristic peaks in a powder X-ray diffraction pattern of hydrochloride quarterhydrate of (3,4-Dichloro-phenyl)-((S)-3-propyl-pyrrolidin-3-yl)-methanone are 5.5±0.20, 9.4±0.20, 10.6±0.20, 12.5±0.20, 14.6±0.20, 16.2±0.20, 16.6±0.20, 17.3±0.20, 18.6±0.20, 19.6±0.20, 22.2±0.20, 22.7±0.20, 23.1±0.20, 23.7±0.20 and 25.3±0.20, in particular characteristic peaks are 9.4±0.20, 14.6±0.20, 16.6±0.20, 19.6±0.20 and 22.2±0.20.

The hydrochloride of (3,4-Dichloro-phenyl)-((S)-3-propyl-pyrrolidin-3-yl)-methanone solid can be identified by as few as one characteristic peak in its powder X-ray diffraction pattern as shown in FIG. 2. Two-theta angle positions of characteristic peaks in a powder X-ray diffraction pattern of hydrochloride quarterhydrate of (3,4-Dichloro-phenyl)-((S)-3-propyl-pyrrolidin-3-yl)-methanone are 5.2±0.20, 10.5±0.20, 12.3±0.20, 15.3±0.20, 15.6±0.20, 16.0±0.20, 17.1±0.20, 18.8±0.20, 23.0±0.20, 23.9±0.20, 27.2±0.20, 28.2±0.20 and 30.5±0.20.

Crystal Structural Analysis

For single crystal structure analysis a single crystal was mounted in a loop on a goniometer and measured at ambient conditions. Data were collected on a GEMINI R Ultra diffractometer from Oxford Diffraction (Oxford). Cu-radiation of 1.54 Å wavelength was used for data collection. Data was processed with the software CRYSALIS. The crystal structure was solved and refined with standard crystallographic software. In this case the program ShelXTL from Bruker AXS (Karlsruhe) was used.

Preparation of single crystals of (3,4-Dichloro-phenyl)-((S)-3-propyl-pyrrolidin-3-yl)-methanone monohydrochloride quarterhydrate 10 mg of (3,4-Dichloro-phenyl)-((S)-3-propyl-pyrrolidin-3-yl)-methanone hydrochloride were dissolved in 0.226 mL of nitromethane at 60° C. The solution was allowed to reach ambient temperature without agitation. After 24 h, single crystals were harvested and subjected to X-ray crystal structure analysis.

Structural data derived from (3,4-Dichloro-phenyl)-((S)-3-propyl-pyrrolidin-3-yl)-methanone hydrochloride quarterhydrate single crystal X-ray analysis are the following unit cell parameters,

| | |
|---|---|
| a | 6.14 Å |
| b | 16.70 Å |
| c | 17.43 Å |
| alpha | 66.73° |
| beta | 81.47° |
| gamma | 86.51° | wherein a, b, and c are each a representative length of the crystal lattice and alpha, beta and gamma are unit cell angles. The salt crystallizes in the space group P1, affording a cell volume of 1623.82 Å$^3$.

Figure 5:
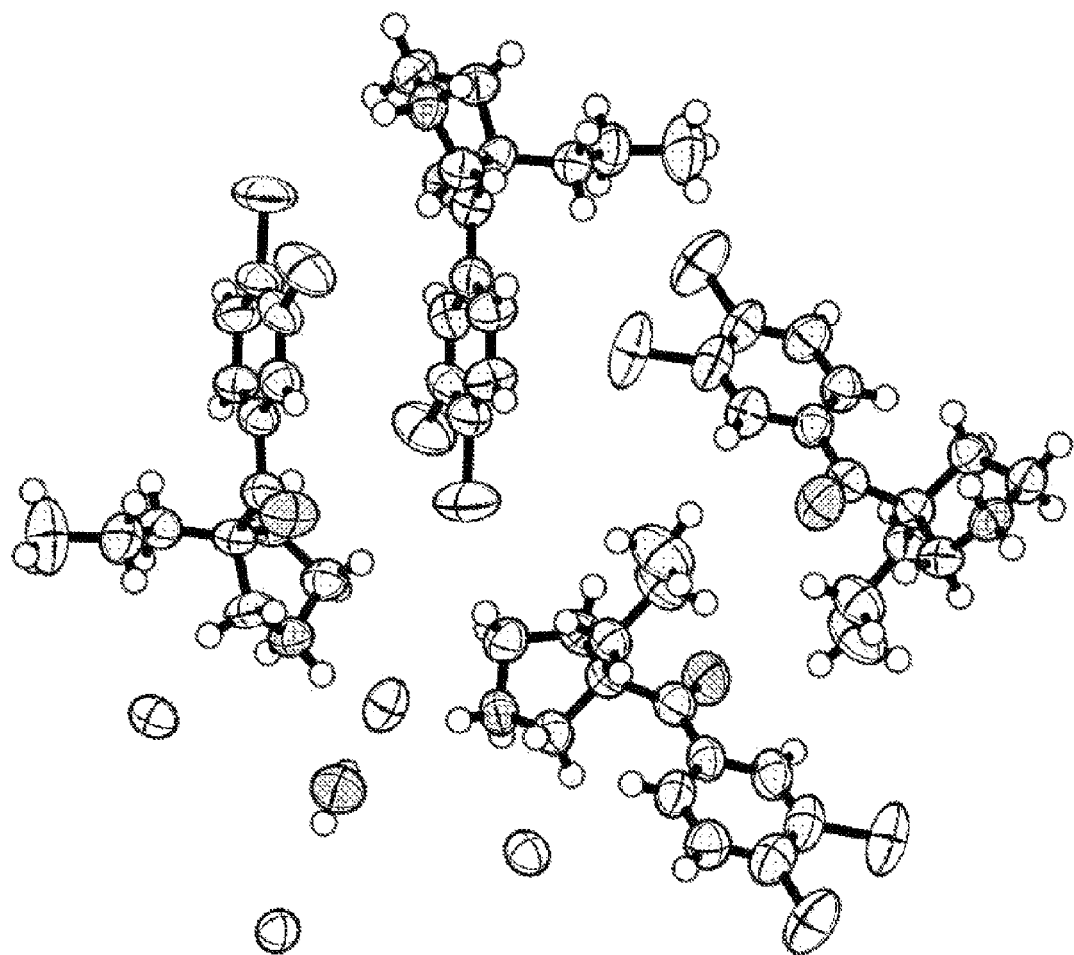
FIG. 5 is a single crystal X-ray image of a hydrochloride quarterhydrate of (3,4-Dichloro-phenyl)-((S)-3-propyl-pyrrolidin-3-yl)-methanone.

FIG. 5 is a single crystal X-ray image of a hydrochloride quarterhydrate of (3,4-Dichloro-phenyl)-((S)-3-propyl-pyrrolidin-3-yl)-methanone.

Differential Scanning Calorimetry (DSC)

DSC curves were recorded using a Mettler-Toledo™ differential scanning calorimeter DSC820, DSC821 or DSC1 with a FRS05 sensor. System suitability tests were performed with Indium as reference substance and calibrations were carried out using Indium, Benzoic acid, Biphenyl and Zinc as reference substances.

For the measurements, approximately 2-6 mg of sample were placed in aluminum pans, accurately weighed and hermetically closed with perforation lids. Prior to measurement, the lids were automatically pierced resulting in approx. 1.5 mm pin holes. The samples were then heated under a flow of nitrogen of about 100 mL/min using heating rates of usually 10 K/min.

Figure 4:
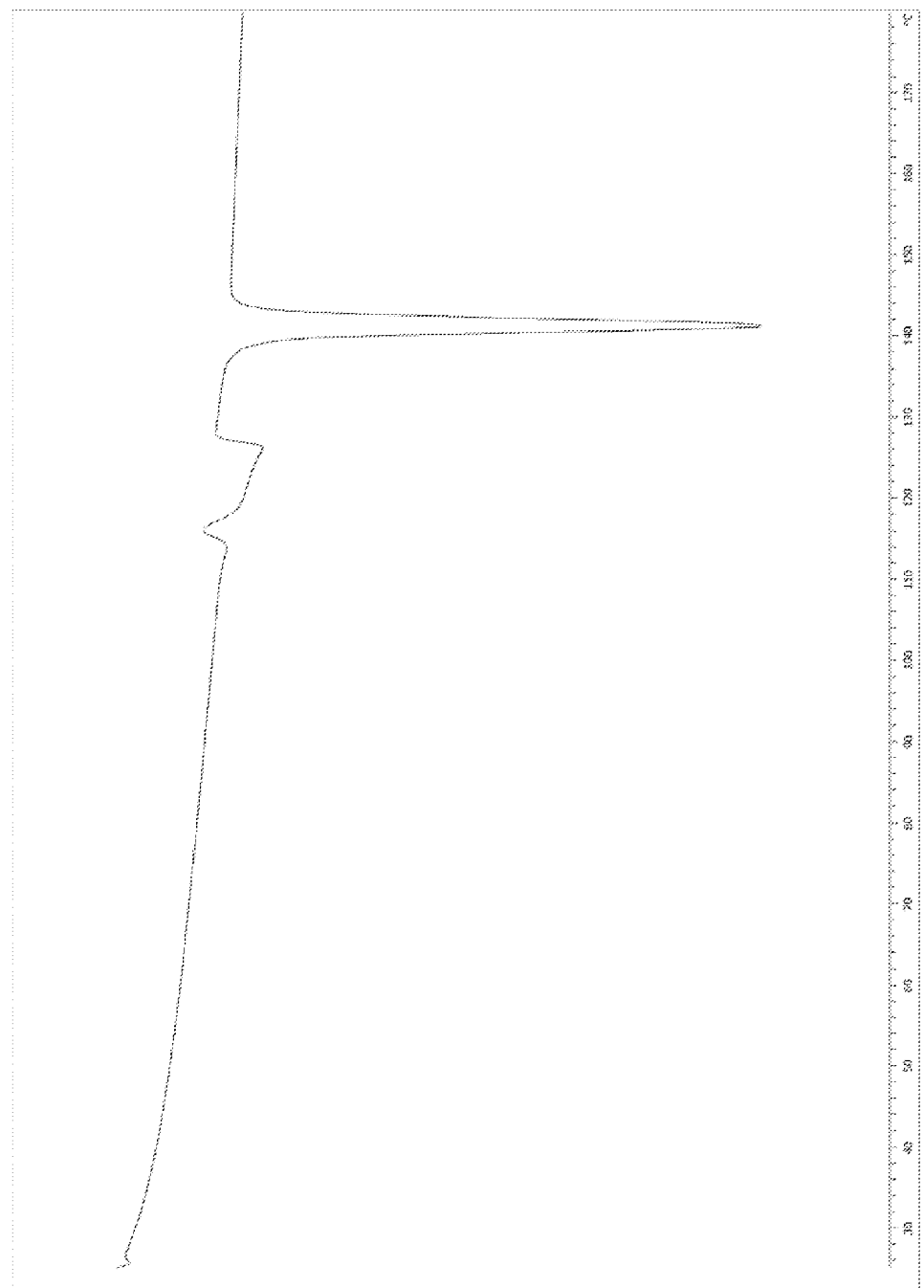
FIG. 4 is a thermogram of a hydrochloride quarterhydrate of (3,4-Dichloro-phenyl)-((S)-3-propyl-pyrrolidin-3-yl)-methanone obtained by differential scanning calorimetry (DSC).

FIG. 4 is a thermogram of a hydrochloride quarterhydrate of (3,4-Dichloro-phenyl)-((S)-3-propyl-pyrrolidin-3-yl)-methanone obtained by differential scanning calorimetry (DSC).

Figure 6:
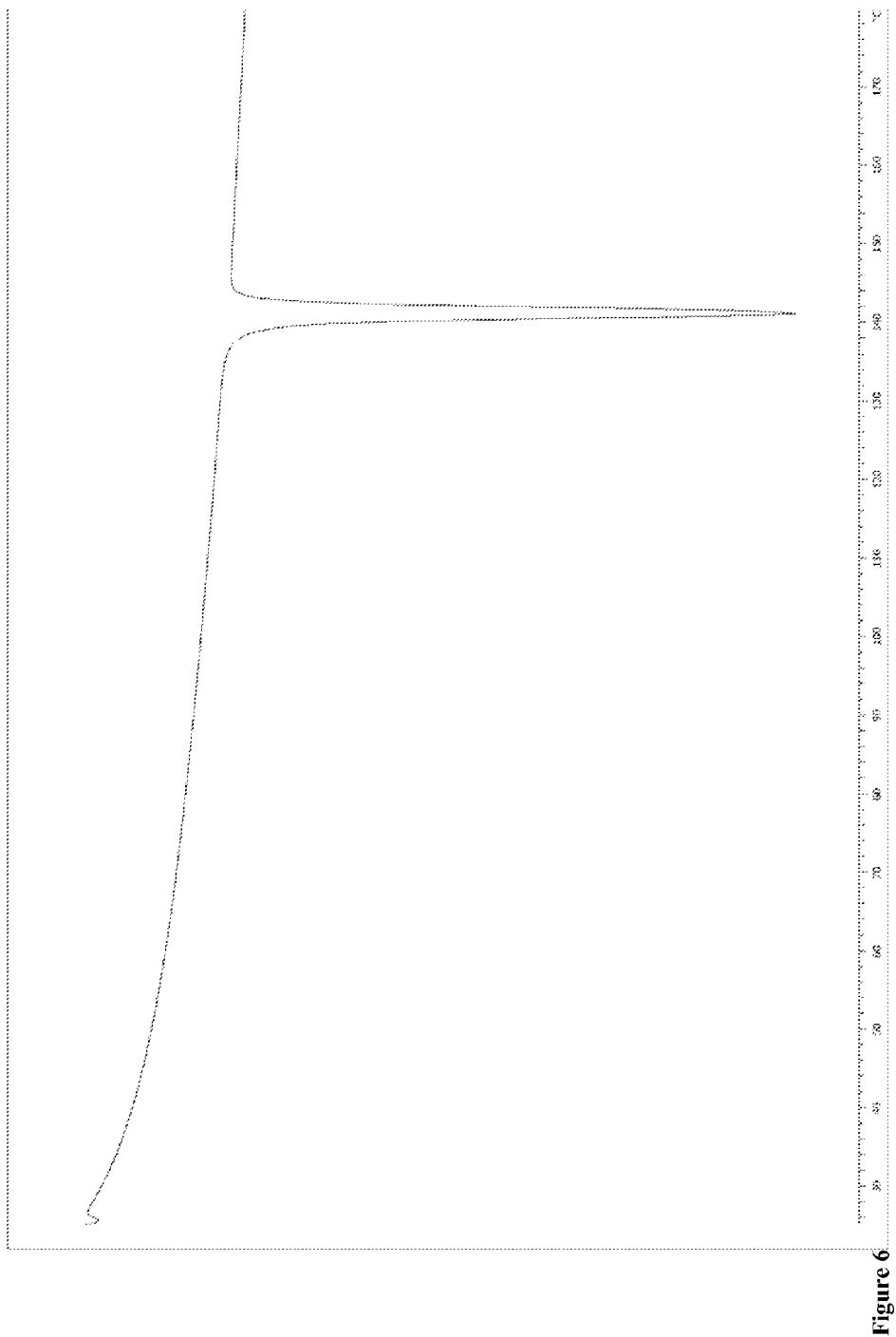
FIG. 6 is a thermogram of a hydrochloride of (3,4-Dichloro-phenyl)-((S)-3-propyl-pyrrolidin-3-yl-methanone obtained by differential scanning calorimetry (DSC).

FIG. 6 is a thermogram of a hydrochloride of (3,4-Dichloro-phenyl)-((S)-3-propyl-pyrrolidin-3-yl)-methanone obtained by differential scanning calorimetry (DSC).

Thermal Gravimetric Analysis (TGA)

TGA was performed on a Mettler-Toledo™ thermogravimetric analyzer (TGA850 or TGA851). System suitability tests were performed with Hydranal as reference substance and calibrations using Aluminum and Indium as reference substances.

For the thermogravimetric analyses, approx. 5-10 mg of sample were placed in aluminum pans, accurately weighed and hermetically closed with perforation lids. Prior to measurement, the lids were automatically pierced resulting in approx. 1.5 mm pin holes. The samples were then heated under a flow of nitrogen of about 50 mL/min using a heating rate of 5 K/min.

Figure 3:
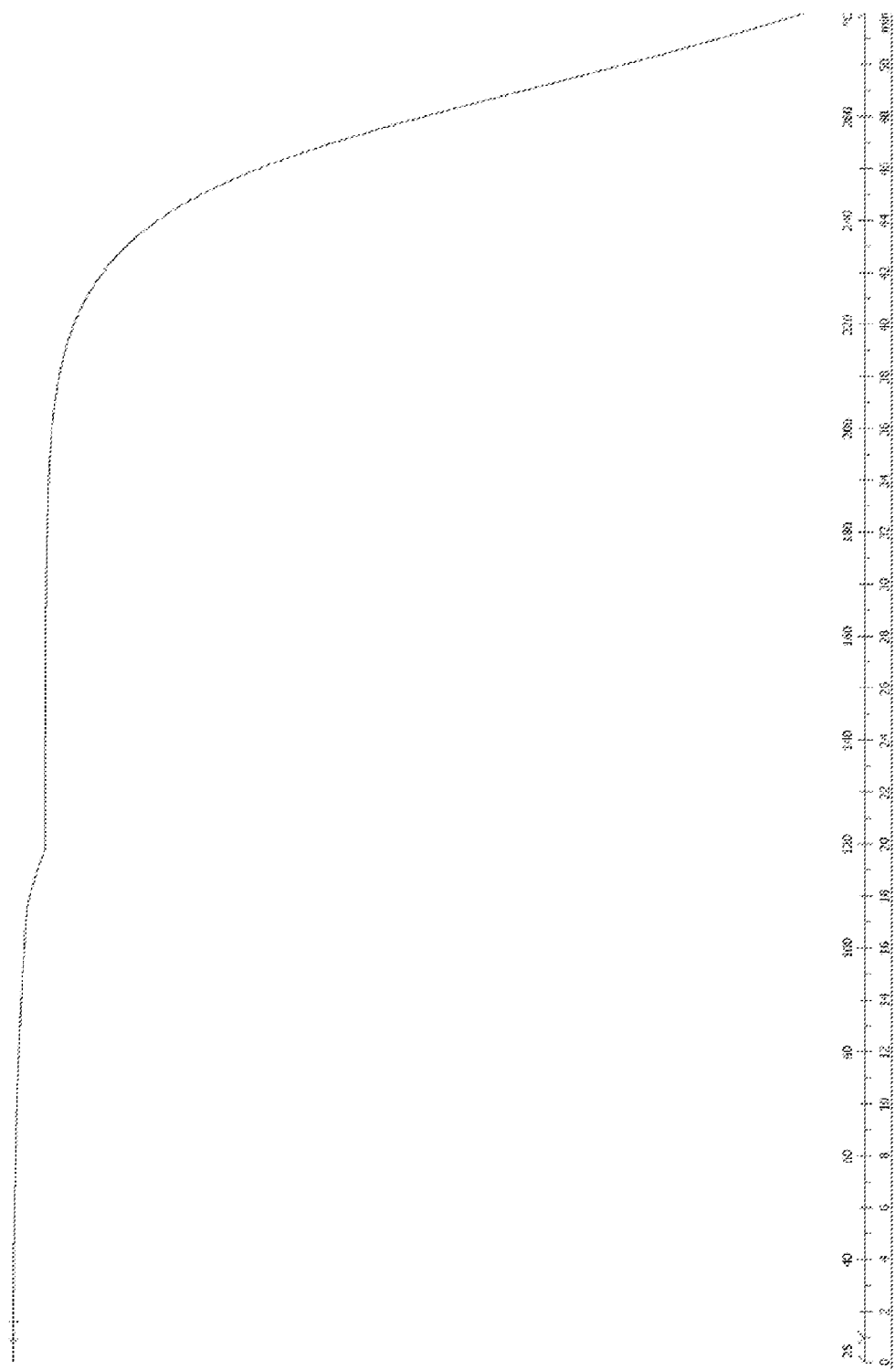
FIG. 3 is a thermogram of a hydrochloride quarterhydrate of (3,4-Dichloro-phenyl)-((S)-3-propyl-pyrrolidin-3-yl-methanone obtained by the al gravimetric metric analysis (TGA).

FIG. 3 is a thermogram of a hydrochloride quarterhydrate of (3,4-Dichloro-phenyl)-((S)-3-propyl-pyrrolidin-3-yl)-methanone obtained by thermal gravimetric analysis (TGA).

Figure 7:
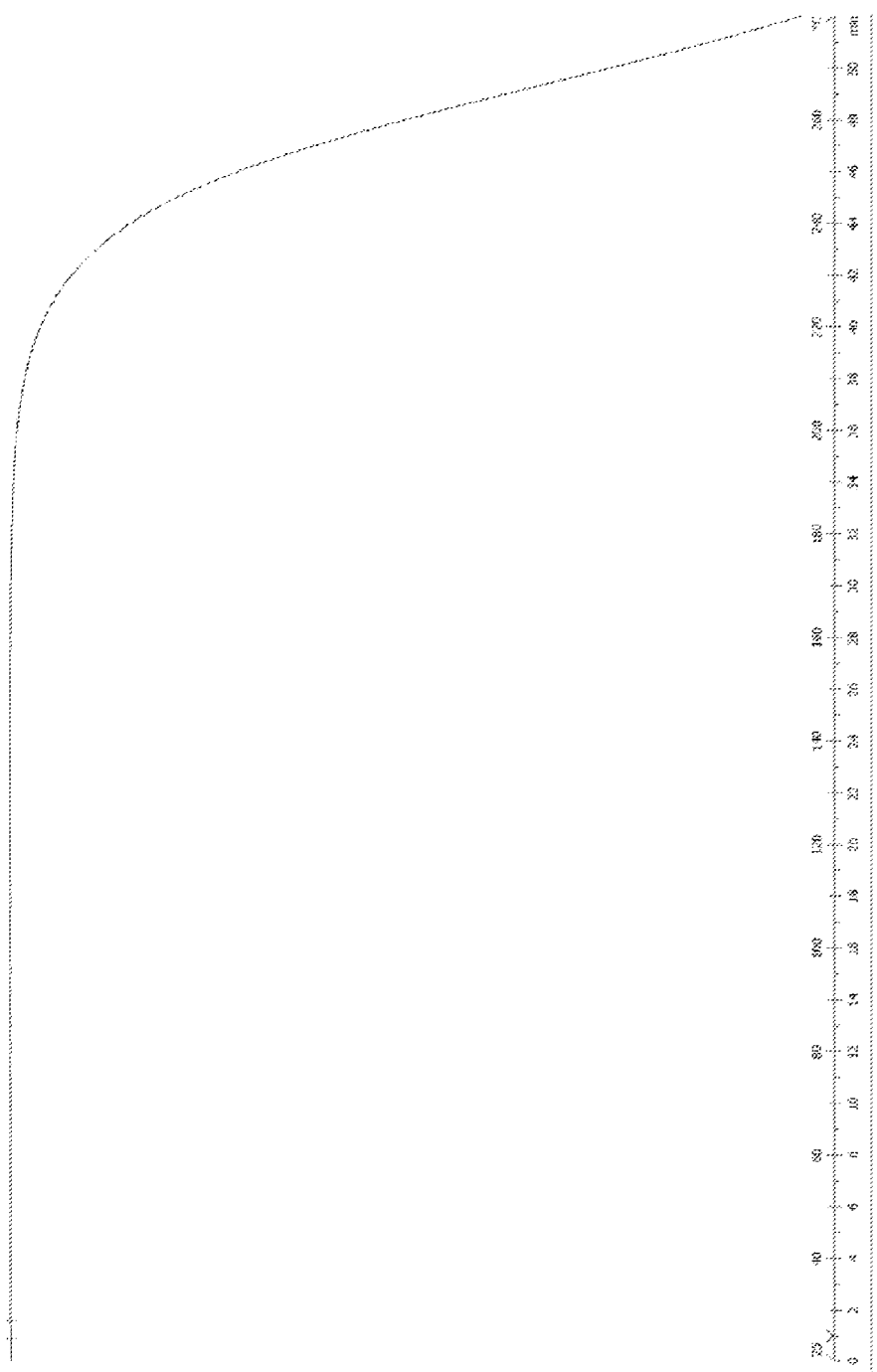
FIG. 7 is a thermogram of a hydrochloride of (3,4-Dichloro-phenyl)-((S)-3-propyl-pyrrolidin-3-yl)-methanone obtained by thermal gravimetric analysis (TGA).

FIG. 7 is a thermogram of a hydrochloride of (3,4-Dichloro-phenyl)-((S)-3-propyl-pyrrolidin-3-yl)-methanone obtained by thermal gravimetric analysis (TGA).

Syntheses

2-Propyl-malonic acid monoethyl ester (3)

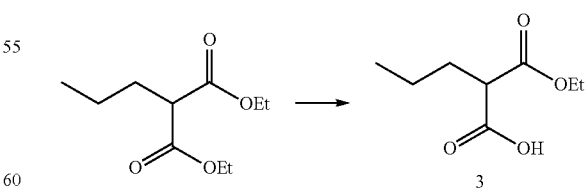

Synthesis 1:

Commercially available diethyl n-propyl malonate ((2), CAS 2163-48-6) was added to a solution of potassium hydroxide (KOH) in ethanol. The malonate (2) was added at a rate such that the internal temperature did not exceed 22°

C. Alternatively, a 10% solution of KOH in ethanol can be added to an ethanol solution of the malonate (see Hu, B. et al., Org. Process Res. Dev. 2007, 11, 90-93). The reaction mixture was stirred at ambient temperature for 60 h and was monitored for completion by high performance liquid chromatography (HPLC) analysis. Upon completion of the reaction, the ethanol was removed in vacuo to provide a white, gel-like material that was dissolved in water. Residual starting material was removed by extraction with MTBE, and the aqueous layer was treated with concentrated $H_2SO_4$ to give the free acid. The aqueous layer was then extracted with MTBE, and the combined organic extracts were washed with water. Removal of the solvent in vacuo gave (3) as a colorless liquid. This material was taken into the following step without further purification.

Synthesis 2:

Alternatively, (3) can be prepared in the following way. Potassium hydroxide pellets (88%, 33.10 g, 0.519 mol, 0.99 equiv) were dissolved in 400 mL ethanol. The solution was cooled to 15° C. and diethyl n-propyl malonate (2) was added dropwise (105.9 g, 0.524 mol, 1.00 equiv) over 30 min at such a rate that the internal temperature did not exceed 19° C. The addition funnel was charged with 45 mL ethanol, and the ethanol rinse was added to the reaction mixture. After addition the reaction was warmed to room temperature (RT). The reaction mixture was stirred for 66 h at RT. The solvent was then removed in vacuo to afford an amorphous white solid. This material was dissolved in water (400 mL) and ethanol (50 mL). The aqueous phase was extracted with methyl tertiary butyl ether (MTBE) (200 mL) to remove the residual starting material, and the phases were separated. The aqueous phase was then cooled to ca 15° C. and concentrated sulphuric acid ($H_2SO_4$) (29.4 g, 16.0 mL, 0.57 equiv) was added dropwise to the rapidly stirred solution. The acid was added at a rate such that the internal temperature did not exceed 15° C. Addition of the acid led to precipitation of a substantial amount of inorganic salts. The final pH of the aqueous phase was measured to be 2.0. The aqueous phase was extracted twice with MTBE (500 mL then 200 mL) and the combined organic layers was washed with water ($H_2O$) (100 mL). The organic phase was concentrated in vacuo to provide 104 g of crude mono acid (3) as a colorless liquid which was introduced in the following step without further purification.

Synthesis 3:

A particular alternative is that (3) can be prepared in the following way. 100 g diethyl n-propyl malonate (2) (494 mmol, 1 equiv.) were dissolved in 100 mL ethanol and cooled to 15° C. A solution of 32.3 g KOH (494 mmol, 86% purity, 1 equiv.) in 150 mL ethanol was added dropwise over 30 min keeping the temperature between 15-20° C. The reaction mixture was stirred overnight at RT. 800 mL water and 200 mL MTBE were added. The organic phase was separated and discarded. 400 mL MTBE was added to the aqueous phase and the mixture was cooled to 15° C. 15.7 mL 96% $H_2SO_4$ $_{aq}$ (282 mmol, 0.57 equiv.) were added carefully. The aqueous phase was separated and re-extracted with 200 mL MTBE. The organic phases were combined, washed with 200 mL half saturated $NaCl_{aq}$, dried over $MgSO_4$, filtered and concentrated under reduced pressure at 40-50° C. to give 84.4 g of a colorless oil (3).

2-Methylene-pentanoic acid ethyl ester (4)

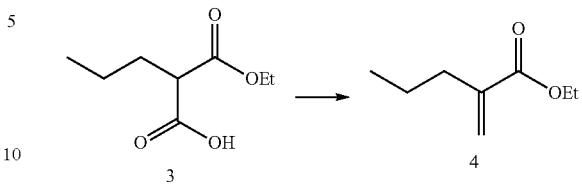

Synthesis 4:

Paraformaldehyde (16.3 g, 0.544 mol, 1.04 equiv.) and ethanol (250 mL) were charged in the reactor at RT. To the resulting slurry was added diethyl amine (38.0 g, 0.519 mol, 0.99 equiv.) dropwise (the temperature raised to 29° C.). The reaction mixture was heated to 70° C. (a clear, colorless solution resulted when the pot temperature reached ca 55° C.). The crude product from the previous reaction dissolved in 50 mL ethanol was added dropwise over 30 min. The addition funnel was rinsed with ethanol (200 proof, 50 mL) and the rinse was added to the reaction mixture. The reaction mixture was stirred at 70° C. until completion of the reaction (ca 1 h) and was then cooled to RT and transferred via cannula to a cooled (ca 10° C.), rapidly stirred mixture of n-hexane (400 mL) and water (400 mL). The transfer was conducted at such a rate that the internal temperature of the quench vessel did not exceed 15° C. The reaction vessel was rinsed with n-hexane (100 mL), and the rinse was transferred to the quench vessel. The contents of the quench vessel were allowed to warm to ambient temperature. The phases were separated, and the aqueous phase was extracted with n-hexane (200 mL). The combined organic layer was filtered over Celite®, and the filter cake was washed with n-hexane (150 mL). Removal of a majority of the n-hexane was accomplished by atmospheric fractional distillation using a 6-inch, vacuum jacketed Vigreux column. The distillation was continued until a pot volume of ca 100 mL and a pot temperature of 89° C. were achieved. The head temperature ranged from 67-69.6° C. during the distillation. The liquid ((4) containing ca. 30% hexane) was transferred to a 250-mL, 3-neck round bottom flask, and the distillation was continued. Collection of the fraction with the by range 158.7-158.9° C. gave the desired product (4) as a colorless liquid (48.7 g).

Synthesis 5:

Alternatively, (4) can be prepared in the following way. 30 g of mono acid mono ester (3) (172 mmol, 1 equiv.) were dissolved in 150 mL ethanol. 15.6 mL 37% aqueous formaldehyde (207 mmol, 1.2 equiv.) were added at room temperature. 18.9 mL diethylamine ($Et_2NH$) (181 mmol, 1.05 equiv.) were added dropwise over 15 min, keeping the temperature between 23-30° C. After 2 h at RT (ca 80% conversion), the reaction mixture was heated to 50° C. for 2 h (until complete conversion). The reaction mixture was cooled to RT, 300 mL water and 100 mL MTBE were added. The aqueous phase was separated and extracted with 100 mL MTBE. The organic phases were combined, washed with 100 mL 1M hydrochloric acid ($HCl_{aq}$), 100 mL half saturated sodium chloride ($NaCl_{aq}$), dried over magnesium sulphate ($MgSO_4$), filtered and concentrated at atmospheric pressure under 100° C. to give 27 g of product (4) as a colorless oil (88% yield, corrected for ca 17% residual MTBE and 1.4% ethanol).

Synthesis 6:

In particular, (4) can be prepared in the following way. 2.33 mL diethylamine (22.3 mmol, 0.8 equiv.) were dissolved in 25 mL Me-THF. 0.64 mL acetic acid (11.1 mmol, 0.4 equiv.) were added followed by 2.3 mL 36.5% aqueous formaldehyde solution (30.6 mmol, 1.1 equiv.). The solution was heated to 50-55° C. and a solution of 5 g of monoacid (3) (27.8 mmol, 97% purity, 1 equiv.) in 5 mL Me-THF was added dropwise over 20 min. After ca 2-3 h, the reaction mixture was cooled to RT, washed with 20 mL water, 20 mL 1 M HCl$_{aq}$, 20 mL half saturated sodium carbonate (Na$_2$CO$_{3\ aq}$) and 20 mL half saturated NaCl$_{aq}$. The organic phase was dried over Na$_2$SO$_4$, filtered and concentrated under reduced pressure (50° C. 150-180 mbar) to give 5.2 g of product (4) as a colorless oil (88% yield, corrected for ca 30% m/m residual Me-THF, 97a % GC) which was used directly in the next step.

Benzyl-methoxymethyl-trimethylsilanylmethyl-amine (6)

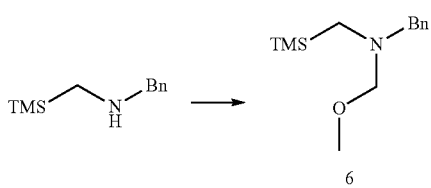 [SMILES: C[Si](C)(C)CNCc1ccccc1 ; COCN(Cc1ccccc1)C[Si](C)(C)C]

Synthesis 7:

A solution of 50 g of 37% formalin and 20 g of methanol (MeOH) in a 2-L reaction vessel was cooled to 0° C. 100 g of Benzyl-trimethylsilanylmethyl-amine (5) was slowly added to the reaction mixture over a period of 25-30 min such that the reaction temperature was held below 10° C. After the addition was complete, the reaction mixture was stirred at 0° C. for 2 h. and warmed to 23° C. After completion of the reaction, Me-THF (1-L) was added to the reaction mixture and the solution so obtained was distilled under atmospheric pressure to remove water azeotropically. The final volume is adjusted to ~500 mL, to obtain a 23.7 wt % solution of the desired product (6) in Me-THF and the solution was cooled to 23° C.

1-Benzyl-3-propyl-pyrrolidine-3-carboxylic acid ethyl ester (7b)

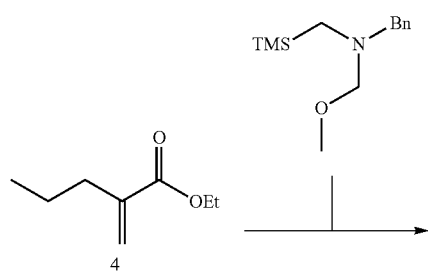

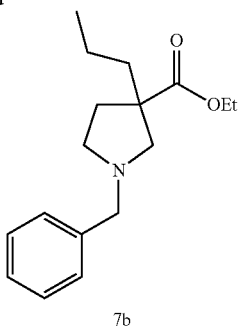

Synthesis 8:

To a Methyltetrahydrofuran (Me-THF) solution (200 mL) of 2-Methylene-pentanoic acid ethyl ester (4) (60 g) was added 1.1 g of trifluoro acetic acid (TFA) and the solution so obtained was heated to 55° C. The Me-THF solution of Benzyl-methoxymethyl-trimethylsilanylmethyl-amine (6) from previous step (Synthesis 7) was then added slowly to the reaction mixture over a period of 2 h. After completion of the reaction, the reaction mixture was cooled to 23° C. To the reaction mixture was then added 400 mL of tap water and the solution was stirred for 5 min. The aqueous layer was then separated and the organic layer was washed one more time with 400 mL of tap water. The Me-THF solution was then concentrated to a minimum volume under reduced pressure and 1.0 L of MeOH was added to the mixture. Remaining Me-THF was then removed by azeotropic distillation. The final volume was adjusted to ~1.0 L to obtain the desired product (7b) as a solution in MeOH.

Synthesis 9:

In particular, (7b) can be prepared in the following way. 5.2 g of olefin (4) from the previous step (Synthesis 6) (25.4 mmol, 67% purity, 1 equiv.) was dissolved in 10 mL Me-THF. 0.27 mL N-methylmorpholine (2.45 mmol, 0.1 equiv.) was added followed by 0.092 mL TFA (1.23 mmol, 0.05 equiv.). The solution was heated to 35° C. and 7.42 mL commercial Benzyl-methoxymethyl-trimethylsilanylmethyl-amine (6) (27.84 mmol, 96%, 1.14 equiv.) was added over 1 h via a syringe pump. After an additional 2 h, the reaction mixture was cooled to 20 mL water and 5 mL saturated Na$_2$CO$_{3\ aq}$ were added. The organic phase was separated and washed with 20 mL water, dried over Na$_2$SO$_4$, filtered and concentrated under reduced pressure to give 7.7 g of a yellow oil (7b) in 88% yield.

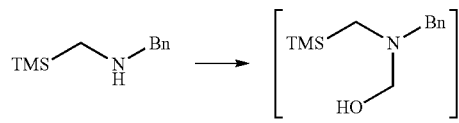

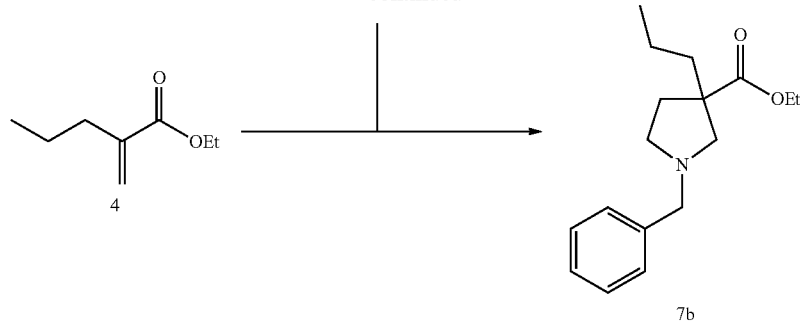

Synthesis 10:

More particular, (7b) can be prepared in the following way. Paraformaldehyde (2.26 g, 71.5 mmol, equiv. 1.31) was charged in the reactor followed by THF (88.7 g, 101 ml), Benzyl-trimethylsilanylmethyl-amine (5) (13.2 g, 68.2 mmol, 1.25 Equiv.) and 1,1,3,3-tetramethylguanidine (157 mg, 172 µl, 1.36 mmol, equiv. 0.025). The mixture was stirred at RT until it got clear (approx. 1.5 hr). The resulting solution was added dropwise over 1.5 h at RT to a mixture consisting of TFA (268 µl, 3.41 mmol) and 2-Methylene-pentanoic acid ethyl ester (4) (8 g, 54.6 mmol). The reaction was stirred overnight (reaction followed by GC, MTBE/NaHCO$_3$ micro work-up) and concentrated under reduced pressure. The oily residue was taken up in 37 mL MTBE. The organic phase was washed with a mixture of 8.6 mL 1M HCl$_{aq}$ (8.62 ml) and 31 mL 25% aqueous ammonium chloride (NH$_4$Cl$_{aq}$) and then twice with 31 mL 25% NH$_4$Cl$_{aq}$. The organic layer was extracted with 49 mL 1M HCl$_{aq}$ (49.2 ml) (pH of aqueous layer is 0-1). The organic phase was separated and discarded. 37 mL MTBE was added to the aqueous phase and the pH was adjusted to 13-14 by addition of 37 mL 2M NaOH$_{aq}$ under stirring (ice bath cooling). The aqueous layer was separated and the organic phase was washed with 31 mL half saturated NaCl$_{aq}$(30.8 ml, Equiv.-), dried over MgSO$_4$, filtered, and concentrated under reduced pressure to yield 11.5 g of product (7b) (74% yield).

3-Propyl-pyrrolidine-3-carboxylic acid ethyl ester (8b)

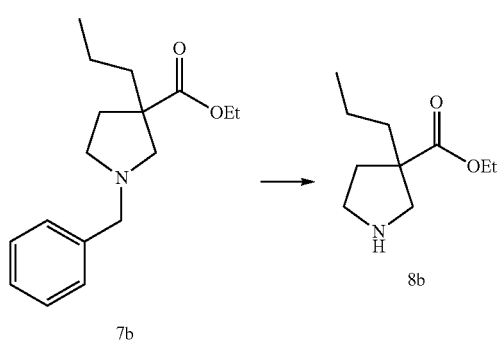 [SMILES: CCCC1(C(=O)OCC)CCN(Cc2ccccc2)C1 ; CCCC1(C(=O)OCC)CCNC1]

Synthesis 11:

A 3-L three necked round bottom flask equipped with a mechanical stirrer and a thermocouple, was charged with 8 g of 20% Pearlman's Catalyst (Pd(OH)$_2$—C) (50 wt % water content) under nitrogen atmosphere. The MeOH solution of (7b) from Synthesis 8 was polished filtered into the 3-L flask. Nitrogen gas was gently bubbled through the solution with moderate stirring for 15 min. Hydrogen gas (H$_2$) was then bubbled through the solution and the reaction mixture was gently warmed to 45° C. Alternatively, the hydrogenation can also be performed in ethanol (EtOH) or isopropanol ("i-PrOH). After completion of the reaction (in process control (IPC) by gas chromatography (GC), ca 5-6 h), bubbling of H$_2$ gas was stopped and the reaction mixture was cooled to ambient temperature while gently bubbling nitrogen gas (N$_2$) gas through it. The reaction mixture was then filtered through a pad of Solka-Floc® and the pad was washed thoroughly with additional MeOH. The filtrate was concentrated to a minimum volume under reduced pressure and then 1 L of Me-THF was added to the residue and the remaining MeOH was removed by atmospheric distillation. The final volume was adjusted to 800 mL by addition of Me-THF and it was washed with 500 mL of 1.0 N aqueous sodium hydroxide (NaOH).

3-Propyl-pyrrolidine-1,3-dicarboxylic acid 1-tert-butyl ester 3-methyl ester (9a)

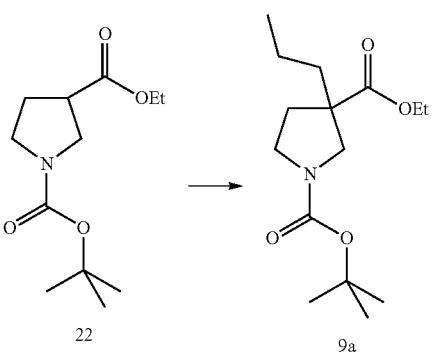 [SMILES: CCOC(=O)C1CCN(C(=O)OC(C)(C)C)C1 ; CCCC1(C(=O)OCC)CCN(C(=O)OC(C)(C)C)C1]

Synthesis 12:

253 g diisopropylamine (2477 mol, 1.33 equiv.) was charged in the reactor followed by 4.5 L THF. The solution was cooled to −50° C. and 1.06 kg 1.6 M buthyl lithium (BuLi) solution in hexanes (2424 mmol, 1.3 equiv.) was added dropwise over ca 60 min while maintaining the temperature between −50° C. and −45° C. After 60 min at −50° C., a solution of 450 g Boc-pyrrolidine ester (22) (1865 mmol, 1 equiv.) in 1.8 L THF was added dropwise over ca 30 min while maintaining the temperature between −50° C. and −45° C. After 60 min at −50° C., a solution of 480 g propyl iodide (2797 mmol, 1.5 equiv.) in 1.8 L THF was added dropwise over ca 30 min while maintaining the temperature between −50° C. and −45° C. After completion of the reaction (GC IPC, usually >99% conversion within approx. 5 h; can be stirred overnight at −50° C.), the reaction mixture was warmed to 0° C. within 60 min and stirred at that temperature for 2 h. 2.6 L 1M HCl$_{aq}$ was are added and the mixture was warmed to RT. 900 mL water and 10 L MTBE were added. The organic phase was separated and washed with 4.5 L 5% NaHCO$_3$ $_{aq}$, 4.5 L half saturated NaCl$_{aq}$ and 4.5 L water. The organic phase was concentrated under reduced pressure and dried at 50-60° C. to give 518 g of crude (9a) (>95% yield).

(S)-3-Propyl-pyrrolidine-1,3-dicarboxylic acid 1-tert-butyl ester 3-methyl ester (9xa)

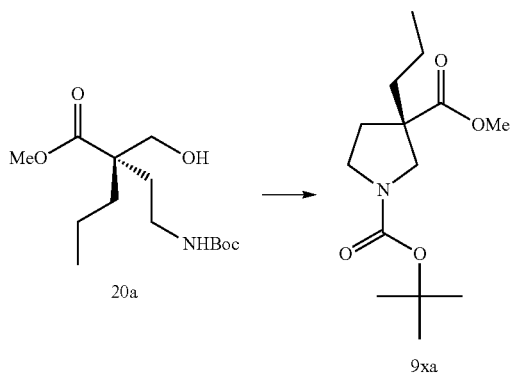 [SMILES: CCC[C@@](CO)(CCNC(=O)OC(C)(C)C)C(=O)OC ; CCC[C@]1(C(=O)OC)CCN(C(=O)OC(C)(C)C)C1]

Synthesis 13:

10 g alcohol (20a) (31.4 mmol, 1 equiv., 91% purity) were dissolved in 100 mL toluene. 3.98 g MsCl (2.71 mL, 34.6 mmol, 1.1 equiv.) were added and the mixture was cooled to 0-5° C. 13.2 mL triethylamine (94. mmol, 3 equiv.) were added, the cooling bath was removed and the suspension was warmed to RT. After 30 min (IPC control by GC), the reaction mixture was heated to reflux for 14 h (IPC control by GC). The reaction mixture was cooled to RT and washed with 300 mL water. The aqueous phase were re-extracted twice with 50 mL ethyl acetate, combined dried over Na$_2$SO$_4$, filtered and concentrated at 50° C. under reduced pressure to give 8.87 g of crude pyrrolidine ester (9xa) in 92% yield (ca 90% purity by NMR with internal standard and quantitative GC) and >99.8% e.e. by chiral GC. MS: C$_{14}$H$_{25}$NO$_4$: 271.1788 (found)/271.1784 (calcd)

3-Propyl-pyrrolidine-1,3-dicarboxylic acid 1-tert-butyl ester 3-ethyl ester (9b)

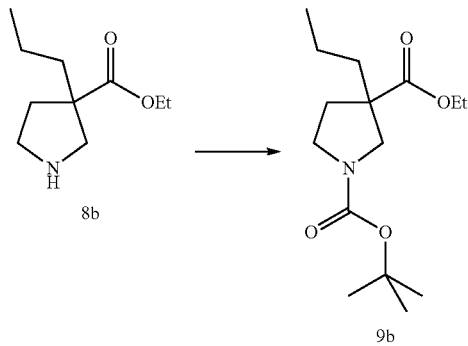 [SMILES: CCCC1(C(=O)OCC)CCNC1 ; CCCC1(C(=O)OCC)CCN(C(=O)OC(C)(C)C)C1]

Synthesis 14:

The Me-THF solution of the deprotected pyrrolidine (8b) from the previous step (synthesis 11) was filtered through a coarse sintered filter, cooled to 0° C. and 42 g of triethylamine (Et$_3$N) was slowly added to the solution. A Me-THF (200 mL) solution of 92 g of Di-tert-butyl dicarbonate (Boc$_2$O) was then slowly added to the reaction mixture such that the temperature was maintained below 15° C. After the addition was complete the reaction mixture was stirred for an additional 1 h. during which the reaction was gently warmed to ambient temperature. After completion of the reaction as shown by GC analysis, most of Me-THF was removed under reduced pressure and 1 L of MeOH was added to the residue. Remaining Me-THF was removed azeotropically by atmospheric distillation and the final volume was adjusted to 1 L.

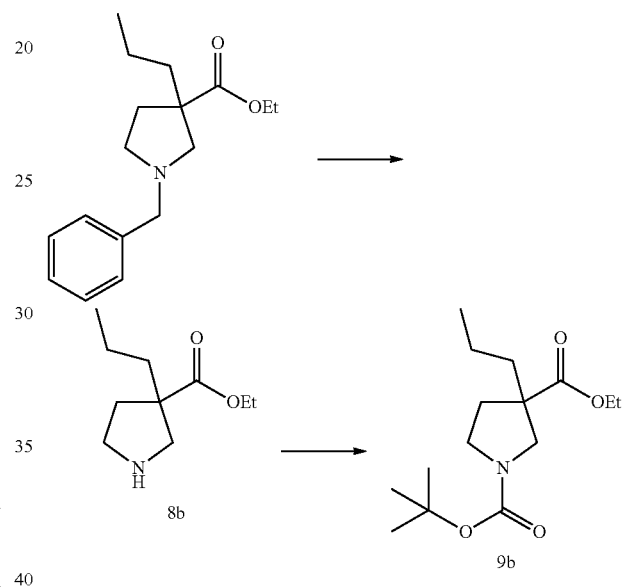

Synthesis 15:

In particular, (9b) can be prepared in the following way. 7.1 g of the crude product (7b) from previous step (Synthesis 9) (22.7 mmol, 88% purity, 1 equiv.) were dissolved in 71 mL ethanol and hydrogenated over 710 mg Pd/C at atmospheric pressure and room temperature. After completion of the reaction, the reaction mixture was degassed and the catalyst was filtered. The crude product (8b) was directly used in the subsequent reaction step. A solution of 5.3 g of Boc$_2$O (23.7 mmol, 1.04 equiv.) in 10.6 mL ethanol were added to the filtrate (8b). After completion of the reaction, reaction mixture was concentrated under reduced pressure and the oily residue was taken up in 21 mL MTBE. The solution was washed with 7 mL of 0.25 M HCl$_{aq}$ followed by 7 mL water. The organic layer was dried over MgSO$_4$, filtered and concentrated under reduced pressure to give 6 g of crude product (9b) as yellow oil in ca 85% yield.

Synthesis 16:

More particular, (9b) can be prepared in the following way. 11.5 g of the crude product (7b) from the previous step (Synthesis 8) was dissolved in 115 mL ethanol and hydrogenated at room temperature and atmospheric pressure over 1.15 g of 10% Pd/C (2.7 mol % Pd). After completion of the reaction, the solution was partially concentrated. A solution of di-tert-butyl dicarbonate (8.93 g, 40.5 mmol, Equiv. 1.00) in 58 mL ethanol was added dropwise over 20 minutes at RT.

After completion of the reaction, the reaction mixture was concentrated, dissolved in 35 mL toluene. The solution was washed successively with 42 mL 5% aqueous citric acid solution, half saturated NaHCO$_3$ $_{aq}$ and 35 mL half saturated NaCl. The organic phase was dried over MgSO$_4$, filtered, and concentrated under reduced pressure to give 11.2 g of product (9b) (92% yield).

(S)-3-Propyl-pyrrolidine-1,3-dicarboxylic acid 1-tert-butyl ester 3-ethyl ester (9b)

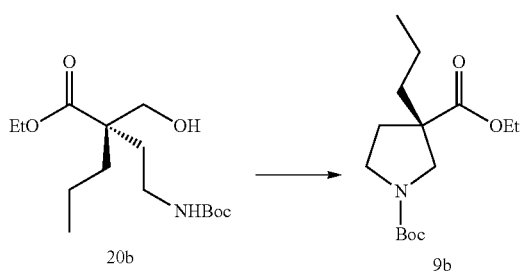 [SMILES: CCC[C@@](CO)(CCNC(=O)OC(C)(C)C)C(=O)OCC ; CCC[C@]1(C(=O)OCC)CCN(C(=O)OC(C)(C)C)C1]

Synthesis 17:

500 mg of crude product (20b) from previous step (synthesis 40) was dissolved in 20 mL THF together with 696 mg triphenylphosphine (PPh$_3$) (2.5 mmol, 1.8 equiv.). 0.39 mL Diethylazodicarboxylate (DEAD) (2.4 mmol, 1.7 equiv.) was added slowly. The mixture was stirred at RT for 3 h and the solvent were concentrated under reduced pressure. The crude product was purified by chromatography (SiO$_2$, AcOEt/Heptane 1:4) to give 113 mg of the expected product (9b).

3-Propyl-pyrrolidine-1,3-dicarboxylic acid 1-tert-butyl ester (10)

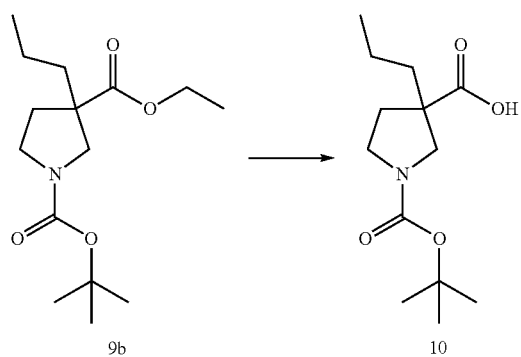 [SMILES: CCCC1(C(=O)OCC)CCN(C(=O)OC(C)(C)C)C1 ; CCCC1(C(=O)O)CCN(C(=O)OC(C)(C)C)C1]

Synthesis 18:

The MeOH solution of the crude ester (9b) from the previous step (synthesis 14) was cooled to ambient temperature and 100 mL of 50% aqueous NaOH was carefully added. The reaction mixture was heated at 65° C. for 6 h. After completion of the reaction, the reflux condenser was changed to a distillation unit and most of the MeOH was distilled out at atmospheric pressure. The reaction mixture was cooled to ambient temperature and additional tap water (500 mL) was added. The aqueous solution so obtained was extracted with 500 mL of MTBE. The aqueous layer was separated and carefully acidified with ~100 mL of 12 N HCl and extracted with 1 L of MTBE.

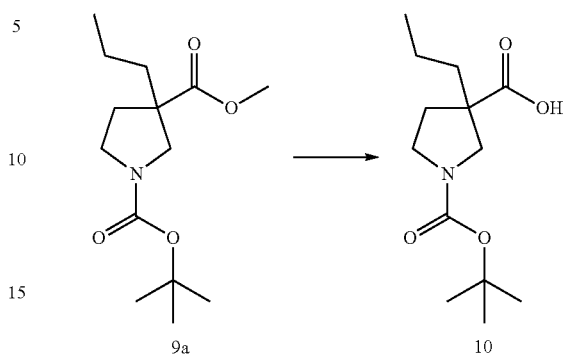

Synthesis 19:

Alternatively, (10) can be prepared in the following way. 516 g of ester (9a) (1.81 mol, 1 equiv) were charged in the reactor followed by 2.5 L methanol. 452 g 32% NaOH$_{aq}$ (335 mL, 3.61 mmol, 2 equiv.) were added and the reaction mixture was stirred at 55° C. (until reaction completion by GC IPC, usually <4 h) then overnight at RT. 2 L water were added and the methanol was distilled under reduced pressure (60° C./150 mbar). The resulting solution was added at 10-15° C. to a mixture consisting of citric acid (500 g) in 2 L of water and 2 L isopropyl acetate. The organic phase was separated and washed twice with 1 L 10% NaCl$_{aq}$. The aqueous phases were re-extracted sequentially with 1 L isopropyl acetate. The organic phases were combined and partially concentrated. The NaCl residue was filtered off and the filtrate was further concentrated to give 498 g of crude (10) as a viscous oil (crystallizes on standing) in quantitative yield.

(S)-3-Propyl-pyrrolidine-1,3-dicarboxylic acid 1-tert-butyl ester (10x)

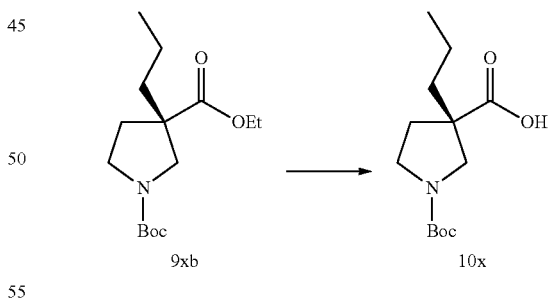

Synthesis 20:

100 mg of the ester 9xb from previous reaction (synthesis 17) (0.33 mmol, 1 equiv.) was dissolved in 2 mL ethanol. 222 µL 3N NaOH (0.66 equiv., 2 equiv.) were added and the hydrolyzed by heating at 55° C. (IPC by GC after acidic micro work-up and derivatization with diazomethane). The reaction mixture was cooled to RT and was acidified with 0.1 M HCl. The mixture was extracted twice with AcOEt. The organic phases were combined, dried over Na$_2$SO$_4$, filtered and concentrated under reduced pressure to give 22 mg of a colorless oil (10x).

(S)-1-tert-Butoxycarbonyl-3-propyl-pyrrolidine-3-carboxylate(R)-1-phenyl-ethyl-ammonium (11)

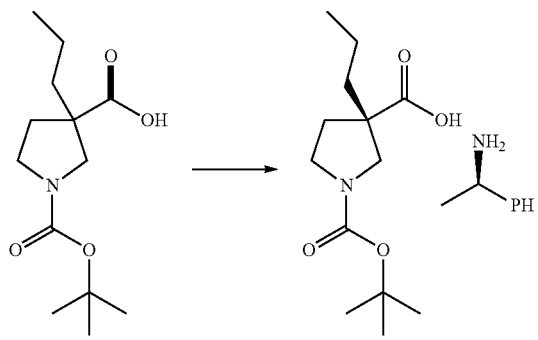

Synthesis 21:

The MTBE solution of the crude acid (10) from previous step (Synthesis 18) was concentrated to a minimum volume under reduced pressure and 350 mL of heptane was added. The solution is then distilled (70° C.) at atmospheric pressure to remove residual MTBE and filtered through a coarse sintered funnel. The solution so obtained was warmed to 55° C. and 26 g of (R)-(+)-1-phenylethylamine was carefully added. After the addition was complete, 2.0 g of the desired diastereomeric salt was added as seeds. The mixture so obtained was aged for 18-24 h with gentle stirring. At the end of this period, the mixture is cooled and filtered and washed with 200 mL of ice-cold heptane to obtain 47.6 g of the desired diastereomeric salt (11) with 97% enantiomeric excess (ee).

Synthesis 22:

Alternatively, (11) can be prepared in the following way. 498 g of crude acid (10) from synthesis 19 (1.8 mol, 1 equiv., taken as 100% yield from ester (9a)) were dissolved in 2.5 L isopropyl acetate. The solution was heated to ca 50° C. and 131 g (R)-(+)-1-phenylethylamine (138 mL, 1.08 mol, 0.6 equiv.) were added. The crystallization was induced by seeding and the suspension was stirred overnight at 50° C. then cooled to RT and stirred for 4 h. The suspension was filtered and the filter cake was washed with 500 mL isopropyl acetate. The crystals were dried overnight at 50° C. under reduced pressure to give 435 g of the amine salt (11) in 38% yield and 97.5:2.5 diastereomeric ratio to give 498 g of crude (11) as a viscous oil (crystallizes on standing) in quantitative yield.

Seed Crystals: 1-(tert-butoxycarbonyl)-3-propylpyrrolidine-3-carboxylic acid (47 g, 174 mmol, 1 equiv., 96% purity corrected for residual solvents) was charged in the reactor followed by iPrOAc (220 g, 253 ml). The mixture was heated to 50° C. to give a solution and (R)-(+)-1-phenethylamine (12.9 g, 13.6 ml, 105 mmol, 0.6 equiv.) was added.

A 1 mL sample of the resulting solution was removed from the reactor. 2 mL heptane was added and the solution was rotavaped. 2 mL heptane was added and the solution was rotavaped. 1.5 mL heptane was added and the resulting solution was scratched with a Pasteur pipette. The solution was stirred until a suspension was obtained.

The suspension was returned to the reactor to initiate the crystallization. The resulting suspension was stirred 17 h at 50° C., cooled to RT for 3 h and filtered. The filter cake was washed with iPrOAc (87.0 g, 100 ml) and dried at 10 mbar/55° C. until constant weight to give 26.9 g of product as a white powder.

(S)-3-Propyl-pyrrolidine-1,3-dicarboxylic acid 1-tert-butyl ester sodium salt (12)

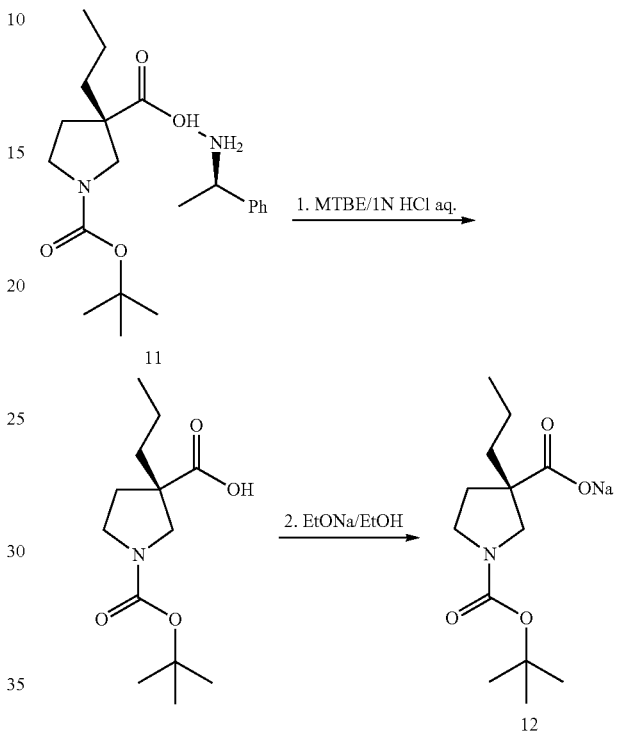

Synthesis 23:

The (R)-(+)-1-phenylethylamine salt (11) (38 g, 0.1 mol) was suspended in MTBE (300 ml), 1N HCl aq. (200 ml) and was then added. The reaction mixture was stirred for 0.5 hours. The organic layer was washed with 1N HCl aq. (100 ml) and treated with 21% sodium ethanolate/ethanol (EtONa/EtOH) solution (37.5 ml, 1.0 eq) at room temperature. This slurry was stirred for 2 hours, filter and rinse with MTBE and dried in a vacuum oven at 40° C. for 16 h. This yielded 26.5 g of a white solid (12) (95%, 99.24% ee.

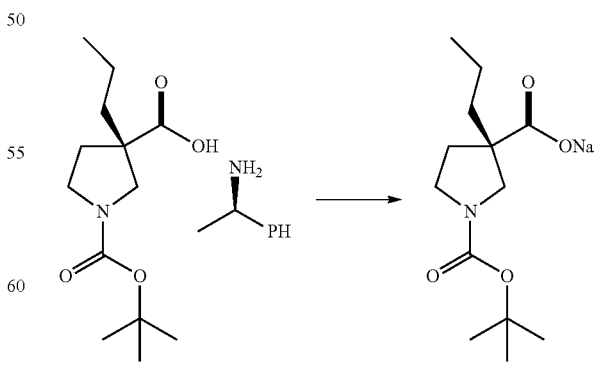

Synthesis 24:

Alternatively, (12) can be prepared in the following way. 250 g of amine salt (11) (660 mmol, 1 equiv.) were suspended in 1.4 L isopropanol. 350 mL of a 2M NaOH solution in methanol was added. After 1-2 h at RT (the suspension usually turns into an almost clear solution after which the crystallization starts), ca 700 mL of solvent are distilled (60° C./reduced pressure; ca 8-12% m/m residual methanol). A mixture of 1.4 L isopropanol and 20 mL water was added and the suspension was stirred overnight at RT (ca 1.4% m/m water by KFT). The suspension was filtered and washed with 300 mL isopropanol. The crystals were dried at 50° C./<10 mbar to give 167 g of sodium salt (12) as a white powder in ca 90% yield and 99.3:0.7 enantiomeric ratio. The product (12) may contain ca 0.2-0.4% m/m isopropanol and 0.2-0.3% m/m water.

Synthesis 25:

Alternatively, (12) can be prepared in the following way. Amine salt (11) (15 g, 39.6 mmol, equiv. 1.00) was charged in the reactor followed by Methanol (39.6 g, 50 ml). A clear solution was obtained. After 10 min at 25° C., 2M NaOH in MeOH (20.8 ml, 41.6 mmol, equiv. 1.05) was added leading to a slightly turbid solution. After 15 min at 25° C., the reactor was discharged and washed with Ethanol (78.9 g, 100 ml) into a 500 mL flask. The solution was concentrated at 55° C./ca 150 mbar (to ca 60 g, light suspension obtained) and further solvent exchanged twice with 125 mL Ethanol, leading to a very thick suspension (M=ca 90 g). The suspension was returned the jacketed reactor. Ethanol (39.4 g, 50 ml) were added (total reaction volume: ca 160 mL). The suspension was heated to 50° C. and cooled over 5 h to 25° C. then stirred for 20 h. The suspension was filtered and washed with 25 mL ice cold Ethanol and dried at 10 mbar/55° C. to give 6.35 g of the sodium salt (12) (57% yield). Analogous protocol with isolation at 0° C.: 61% yield.

Synthesis 26:

Alternatively, (12) can be prepared in the following way. Amine salt (11) (15 g, 39.6 mmol, equiv. 1.00) was charged in a jacketed reactor followed by Methanol (39.6 g, 50.0 ml). A clear solution was obtained. After 10 min at 25° C., 2M NaOH in MeOH (20.8 ml, 41.6 mmol, equiv. 1.05) were added leading to a slightly turbid solution. After 15 min at 25° C., the reactor was discharged into a 500 mL flask. The solution was azeotroped at 55° C./ca 200-150 mbar with i-PrOH (in total 195 g, 250 ml) and was concentrated to ca 70 g. The suspension was transferred back to the jacketed reactor and i-PrOH (62.4 g, 80 ml) was added to adjust the mass to ca 130 g (ca 160 mL reaction volume). The suspension was heated to 50° C. and cooled over 5 h to 25° C. then stirred for 10 h at 25° C., filtered, washed with i-PrOH (19.5 g, 25 ml) and dried (50° C./10 mbar) to give 9.4 g of sodium salt (12) (85% yield).

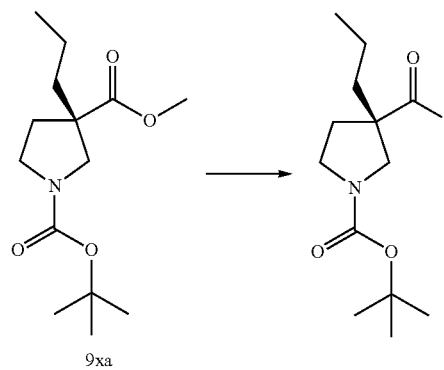

9xa

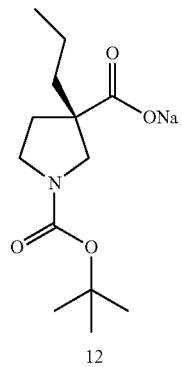

12

Synthesis 27a:

Alternatively, (12) can be prepared in the following way. 8.4 g of (R)-pyrrolidine ester (9xa) (27.6 mmol, 1 equiv.) were dissolved in 50 mL methanol. 5.1 mL 32% $NaOH_{aq}$ (55.1 mmol, 2 equiv.) was added and the reaction was heated to 55-60° C. After completion of the reaction (usually complete within 5 h, GC IPC), 50 mL water were added and the methanol was distilled under reduced pressure at 40° C. The reaction mixture was acidified with 7.4 mL 25% $HCl_{aq}$ (61 mmol, 2.2 equiv.) and extracted 3 times with 50 mL ethyl acetate. The combined organic phases were washed with 50 mL saturated $NaCl_{aq}$, dried over $Na_2SO_4$ and concentrated under reduced pressure to give 7.04 g of crude acid ((S)-3-Propyl-pyrrolidine-1,3-dicarboxylic acid 1-tert-butyl ester) 10x as a light orange oil (95% yield by NMR with internal standard).

Synthesis 27b:

6.9 g of ((S)-3-Propyl-pyrrolidine-1,3-dicarboxylic acid 1-tert-butyl ester) was dissolved in 50 mL isopropanol. 12.5 mL 2M NaOH in methanol (25 mmol, 0.91 equiv.) was added. Crystallization of the sodium salt (12) started after ca 10 min and the suspension was stirred at RT for 2 h. The methanol was removed by solvent exchanged to isopropanol (50° C./reduced pressure, 3 times with 50 mL isopropanol). The volume was adjusted to ca 100 mL and the suspension was stirred overnight at RT. The suspension was cooled to 0-5° C. for 1 h and was filtered. The filter cake was washed with 10 mL ice cold isopropanol and the crystals were dried until constant weight to give: 6 g of sodium salt (12) in ca 80% yield and >99.8% e.e. by chiral GC.

(S)-3-Chlorocarbonyl-3-propyl-pyrrolidine-1-carboxylic acid tert-butyl ester (13)

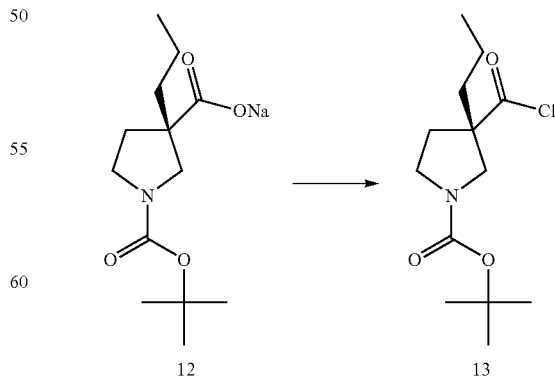

Synthesis 28:

60 g sodium salt (12) (215 mmol, 1 equiv.) were suspended in 450 mL toluene. 300 μL dimethylformamide (DMF) (3.9 mmol, 0.02 equiv.) were added and the suspension was cooled to 0-5° C. A solution of 28.5 g oxalyl chloride (226 mmol, 1.05 equiv.) in 150 mL toluene was added dropwise over 30-70 min during which an almost clear solution was obtained. The reaction mixture was stirred at 0-5° C. for ca 1 h, was warmed to RT over 2 h and was stirred at that temperature overnight (IPC GC: 1-2% starting material, 95.5% derivatized acid chloride (13)).

Synthesis 29:

Alternatively, (13) can be prepared in the following way. 20 g sodium salt (12) (71 mmol, 1 equiv.) were suspended in 200 mL toluene. 109 µL DMF (1.4 mmol, 0.02 equiv.) were added and the suspension was cooled to 0-5° C. 6.5 mL oxalyl chloride (73.98 mmol, 1.05 equiv.) was added dropwise over 30 min during which an almost clear solution was obtained. The reaction mixture was stirred at 0-5° C. for ca 1 h, was warmed to RT and was stirred at that temperature overnight (IPC GC after derivatization).

(S)-3-(3,4-Dichloro-benzoyl)-3-propyl-pyrrolidine-1-carboxylic acid tert-butyl ester (14)

a) Grignard Formation (A')

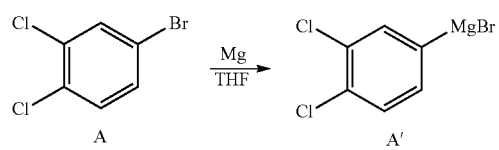

Synthesis 30:

6.8 g Mg (279 mmol, 1.3 equiv.) were suspended in 60 mL THF. The suspension was heated to 40° C. and 2% of a solution of 70.5 g 3,4-dichlorobromobenzene (A) in 200 mL THF was added (the Grignard started within a few minutes). After the exotherm ceased, the remaining aryl bromide solution was added over 2 h. The reaction mixture was stirred 1 h at 40° C. (completion followed by GC IPC) then cooled to RT.

b) Grignard Addition

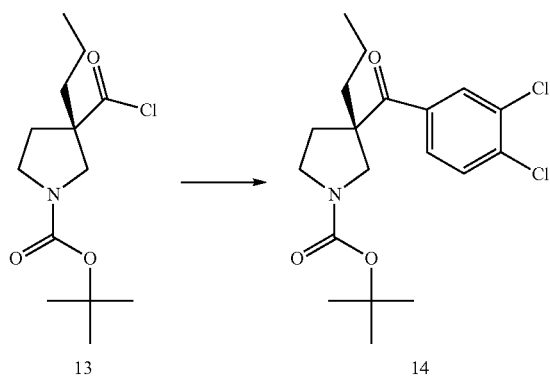 [SMILES: CCC[C@]1(C(=O)Cl)CCN(C(=O)OC(C)(C)C)C1 ; CCC[C@]1(C(=O)c2ccc(Cl)c(Cl)c2)CCN(C(=O)OC(C)(C)C)C1]

Synthesis 31:

The acid chloride (13) solution (synthesis 28) was degassed 3 times and 55.8 g of N,N,N',N',N''-pentamethyl-diethylenetriamine (PMDTA) (322 mmol, 1.5 equiv.) were added. The light suspension was heated to 40-45° C. and the Grignard solution (A') (synthesis 30) was added dropwise over 1.5 h. After 1 h additional reaction time (IPC<2% acid chloride detected), the reaction mixture was cooled to RT.

500 mL 2M HCl$_{aq}$, 300 mL saturated NaCl$_{aq}$ and 300 mL ethanol were added. The organic phase was separated and washed with a mixture consisting of 500 mL 2M HCl$_{aq}$, 300 mL saturated NaCl$_{aq}$ and 300 mL ethanol. The organic phase was washed with 400 mL 1M NaOH$_{aq}$ and twice with 150 mL 10% NaCl$_{aq}$. The organic phase was concentrated under reduced pressure to an oil, taken up in 100 mL toluene and concentrated again to give 87 g of crude (14) with 80a % purity.

Synthesis 32:

Alternatively, (14) can be prepared in the following way. The acid chloride (synthesis 29) solution (13) was degassed 3 times (vacuum/nitrogen cycles). 71.2 mg of copper chloride (CuCl) (0.7 mmol, 0.01 equiv.) were added and the reaction mixture was cooled to 0-2° C. 1.35 equivalent of 3,4-dichlorophenyl-MgBr (A') (as a ca 1 M solution in THF) were added dropwise over 60 min keeping the temperature between 0-5° C. After 1 h at 0-5° C. (completion monitored by GC), the reaction was quenched by addition of 123 mL 2M HCl$_{aq}$ at 20-25° C. The aqueous phase was separated and extracted with 50 mL toluene. The organic layers were washed sequentially twice with 100 mL of a 1:1 saturated NH$_4$Cl$_{aq}$/saturated NaHCO$_{3aq}$ mixture, then with 50 mL 1 M NaOH$_{aq}$ and 50 mL half saturated NaCl$_{aq}$. The organic phases were combined and concentrated to dryness to give 31.5 g of crude (14) (ca 80% m/m purity).

2-Cyanomethyl-2-propyl-malonic acid dimethyl ester (16a)

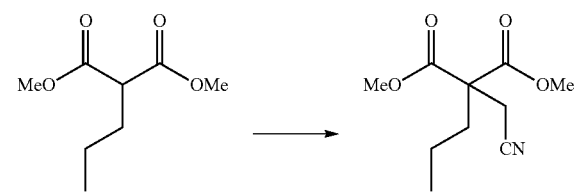

Synthesis 33:

71.6 g KOtBu (625 mmol, 1.1 equiv.) were suspended in 400 mL THF and cooled to 0-5° C. 100 g 2-propyl malonic acid dimethyl ester (15) (568 mmol, 1 equiv.) in solution in 200 mL THF were added dropwise over 30 min keeping the temperature below 10° C. The yellow milky suspension was warmed and stirred for 1 h at room temperature and cooled to 0° C. 52.5 g chloroacetonitrile (682 mmol, 1.2 equiv.) in solution in 200 mL THF was added dropwise over 30 min while keeping the temperature below 10° C. The suspension was warmed and stirred for 2 h at room temperature (ICP by GC). 1 L water was added followed by 500 mL heptane. The aqueous phase was separated and extracted twice with 400 mL ethyl acetate. The organic phases were combined, dried over Na$_2$SO$_4$, and filtered. The resulting dark brown solution was filtered through SiO$_2$ (ca 70 g, the SiO$_2$ bed was washed with ethyl acetate). The resulting light yellow solution was concentrated under reduced pressure to give 114 g of crude product (88% yield, corrected for 93a % purity by GC). The crude product can be purified by distillation (ca 0.5 mbar/95-99° C.) to give 84 g of product in 69% yield and 99a % purity by GC. MS: C$_{10}$H$_{15}$NO$_4$: 213.0999 (found)/213.1001 (calcd).

2-Cyanomethyl-2-propyl-malonic acid diethyl ester (16b)

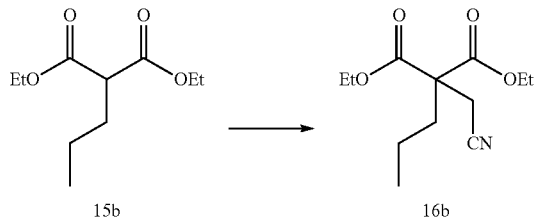 [SMILES: CCCC(C(=O)OCC)C(=O)OCC ; CCCC(CC#N)(C(=O)OCC)C(=O)OCC]

Synthesis 34:

A solution of 50 g 2-propyl-malonate diethyl ester (15b) (242 mmol, 1 equiv.) in 100 mL THF was added dropwise over 15 min to a mixture of 30.5 g KOtBu (2667 mmol, 1.1 equiv.) in 200 mL THF keeping the temperature between 0-10° C. The cooling bath was removed and the reaction mixture was warmed to RT for 1 h and cooled again to 0-2° C. A solution of 22.4 g (291 mmol, 1.2 equiv.) was added dropwise over 30 min keeping the temperature <10° C. After the addition, the reaction mixture was warmed to RT and stirred for 2 h (IPC by GC). 1 L water was added and 200 mL heptane were added (pH aqueous phase: 8). The organic phase was separated and the aqueous phase were extracted twice with 200 mL AcOEt. The organic layers were combined, dried over $Na_2SO_4$, filtered and concentrated under reduced pressure to give 58 g of crude product (16b). The crude product was purified by distillation (0.3 mbar, ca 150° C.) to give 51 g of product (16b) as a colorless oil (84% yield, 96a % purity by GC). MS: $C_{12}H_{19}NO_4$: 241.1311 (found)/241.1314 (calcd).

(S)-2-Cyanomethyl-2-propyl-malonic acid monomethyl ester (17a)

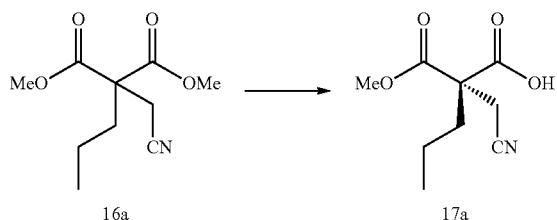

Synthesis 35:

11.60 g 2-Cyanomethyl-2-propyl-malonic acid dimethyl ester (16a) (52.78 mmol; 97%) was diluted with 11.6 ml tetrahydrofuran. The addition of the substrate solution into a 30° C., 0.03 M tris(hydroxymethyl)aminomethane buffer pH 8.1 (92.8 ml, adjusted with 1 N HCl) containing 5.8 g lipase from porcine pancreas (Pancreatic Enzyme Concentrate—High Lipase PCN 1208$H_{15}$B; Scientific Protein Laboratories P.O. Box 158 Waunakee, Wis. 53597-0158, US) started the hydrolysis. The pH of the vigorously stirred emulsion was kept constant at 8.1 by the automated addition (pH-stat) of 1.0M NaOH-solution at 30° C. After 24 h a conversion degree above 95% was reached, after 40 h the final consumption of totally 56.06 ml 1.0M NaOH-solution (56.00 mmol, 1.06 equivalents) was reached. The dark yellow, turbid reaction solution was allowed to cool and its pH was adjusted to 2.0 by adding concentrated sulfuric acid. The subsequent addition of 30 g Dicalite® and 100 ml ethyl acetate into the reaction mixture enabled the adsorption of the denatured enzyme during 15 min. stirring. The filtration through a 100 g Dicalite® bed removed the enzyme efficiently. The filter was washed with ethyl acetate. After spontaneous phase separation of the filtrate the remaining aqueous phase was additionally extracted twice with 100 ml ethyl acetate. The combined organic phases were dried on magnesium sulfate, evaporated and subsequently dried on a HV overnight to give 10.72 (S)-2-Cyanomethyl-2-propyl-malonic acid methyl ester (17a) (97.1% purity; 99% yield) as a light brown solid. Analysis: enantiomeric excess: 98.4% ee (The compounds were ethylated with diazoethane. GC-method: Column: BGB-175; 30 m×0.25 mm; temperature gradient: initial 100° C., ramp 12° C./min to 130° C., ramp 2 0.5° C./min. to 138° C., ramp 3 25° C./min. to 200° C., steady for 1.52 min., total runtime 35 min.; $H_2$ (120 hPa); inj.: 200° C.; det.: 220° C. Retention times: (R)-monoacid (as ethyl ester) 25.99 min, (S)-monoacid (as ethyl ester) 26.24 min, dimethyl ester 27.21 min; $[\alpha]_D = -4.94°$ (1.00 in $CHCl_3$). MS: $[M-H]^- = 198.4$

(S)-2-Cyanomethyl-2-propyl-malonic acid monoethyl ester (17b)

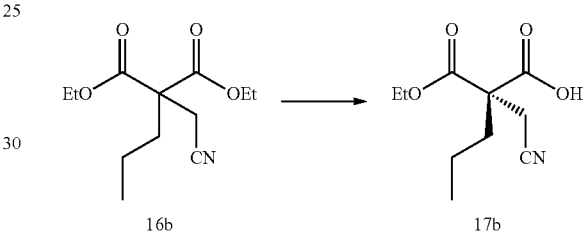

Synthesis 36:

14.00 g 2-Cyanomethyl-2-propyl-malonic acid diethyl ester (16b) (58.02 mmol; 99.9%) was diluted with 14.0 ml tetrahydrofuran. The addition of the substrate solution into a 30° C., 0.03 M tris(hydroxymethyl)aminomethane buffer pH 8.1 (112 ml, adjusted with 1 N HCl) containing 7.0 g lipase from porcine pancreas (Pancreatic Enzyme Concentrate—High Lipase PCN 1208$H_{15}$B; Scientific Protein Laboratories P.O. Box 158 Waunakee, Wis. 53597-0158, US) started the hydrolysis. The pH of the vigorously stirred emulsion was kept constant at 8.1 by the automated addition (pH-stat) of 1.0M NaOH-solution at 30° C. After 50 h, complete conversion, the final consumption of totally 63.99 ml 1.0M NaOH-solution (63.93 mmol, 1.1 equivalents) was reached. After 67 h the yellowish turbid reaction solution was allowed to cool and its pH was adjusted to 1.8 by adding concentrated sulfuric acid. The subsequent addition of 35 g Dicalite® and 100 ml ethyl acetate into the reaction mixture enabled the adsorption of the denatured enzyme during 15 min. stirring. The filtration through a 100 g Dicalite® bed removed the enzyme efficiently. The filter was washed with ethyl acetate. After spontaneous phase separation of the filtrate the remaining aqueous phase was additionally extracted twice with 100 ml ethyl acetate. The combined organic phases were dried on magnesium sulfate, evaporated and subsequently dried on a HV overnight to give 12.23 (S)-2-Cyanomethyl-2-propyl-malonic acid ethyl ester (17b) (94.7% purity; 93.6% yield) as a orange viscous oil. Analysis: enantiomeric excess: 99.4% ee (The compounds were methylated with diazomethane. GC-method: Column: BGB-175; 30 m×0.25 mm; temperature gradient: initial 100° C., ramp 12° C./min to 130° C., ramp 2 0.5° C./min. to 138° C., ramp 3 25° C./min. to 200° C., steady for 1.52 min., total runtime 35 min.; $H_2$ (120 hPa); inj.: 200° C.; det.: 220° C.

Retention times: (S)-monoacid (as methyl ester) 25.99 min, (R)-monoacid (as methyl ester) 26.36 min, diethyl ester 26.65 min; $[\alpha]_D=-6.17°$ (1.00 in CHCl$_3$). Absolute configuration confirmed by X-ray single crystal analysis. MS: [M−H]$^-$=212.5

(S)-2-Cyanomethyl-2-hydroxymethyl-pentanoic acid methyl ester (18a)

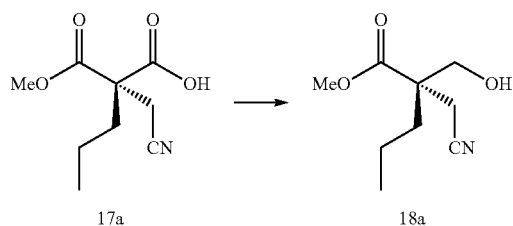

Synthesis 37:

10 g acid (17a) (50 mmol, 1 equiv.) were dissolved in 76 mL THF. 5.44 g N-methylmorpholine (52.7 mmol, 1.05 equiv.) were added and the solution was cooled to 0° C. 7.06 mL isobutyl chloroformate (IBCF) (52.7 mmol, 1.05 equiv.) were added dropwise over 10 min keeping the temperature below 5° C. The suspension was stirred for 1 h at 0° C. and was cooled to ca −78° C. 1.98 g sodium borohydride (NaBH$_4$) (50 mmol, 1 equiv.) was added. After 1 h at −78° C., 10.2 mL methanol (251 mmol, 5 equiv.) were added over 1 h keeping the temperature below −70° C. After an additional 1 h (IPC by GC after derivatization by silylation) at −78° C., 14.4 mL acetic acid (251 mmol, 5 equiv.) were added, the cooling bath was removed and the reaction mixture was warmed to 10° C. over 30 min. 200 mL water were added. The mixture was extracted 3 times with 50 mL ethyl acetate. The organic phases were combined and washed with 300 mL saturated NaHCO$_3$ $_{aq}$. The bicarbonate phase was re-extracted with 50 mL ethyl acetate. The organic phases were combined, dried over Na$_2$SO$_4$, filtered and concentrated under reduced pressure to give 8.7 g of product (18a) as a yellow oil in 77% yield (corrected for 84% purity by quantitative GC analysis). MS: C$_9$H$_{15}$NO$_3$: 185.105 (found)/185.105 (calcd).

(S)-2-Cyanomethyl-2-hydroxymethyl-pentanoic acid ethyl ester (18b)

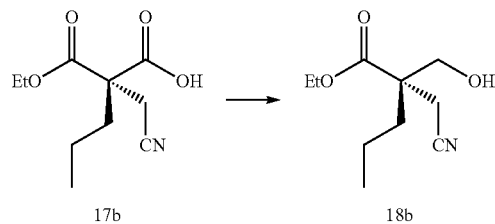

Synthesis 38:

In a first reactor, 5 g monoacid monoester (17b) (22.5 mmol, 1 equiv.) were dissolved in 50 mL THF. The solution was cooled to RT and 2.8 mL N-methylmorpholine (24.8 mmol, 1.1 equiv.) was added followed by 3.3 mL IBCF (24.8 mmol, 1.1 equiv.) and the mixture was stirred for 1 h at 0-5° C. In a second reactor, 1.8 g NaBH$_4$ (45 mmol, 2 equiv.) were suspended in 46 mL THF. The suspension was cooled to −78° C. and 23 mL MeOH were added. To this suspension, the reaction mixture from the first reactor was added portionwise. After 2 h reaction at −78° C., 26 mL acetic acid was added followed by 500 mL (warming to RT). The mixture was extracted twice with 100 mL AcOEt. The organic phases were combined, washed twice with saturated NaHCO$_3$, dried over Na$_2$SO$_4$, filtered and concentrated under reduced pressure to give 4.4 g of crude product as yellow oil. The crude product (18b) was purified by chromatography (SiO$_2$, AcOEt/Heptane 1:1.5) to give 3.3 g of product (18b) in 73% yield. MS: [M+H]$^+$=200; [M+NH$_4$]$^+$=217, Optical rotation: $[\alpha]_D^{20}=-8.95$ (c=0.995 in MeOH).

(S)-N-Boc-2-(2-Amino-ethyl)-2-hydroxymethyl-pentanoic acid methyl ester (20a)

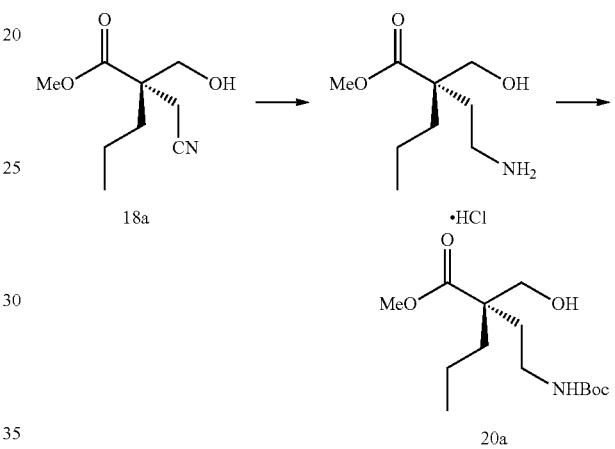

Synthesis 39:

8 g nitrile (18a) (36 mmol, 84% purity, 1 equiv.) were hydrogenated in 80 mL methanol, over 4.55 g 5% Pt/C (3 mol % Pt) in the presence of 4.27 g 36.5% HCl$_{aq}$ (1.18 equiv.) at 50° C./10 bar H$_2$ overnight. The reaction mixture was cooled, filtered to give crude (19a). 8.48 g Di-tert-butyl dicarbonate (Boc$_2$O) (38.1 mmol, 1.05 equiv) and 15.2 mL triethylamine (109 mmol, 3 equiv.) were added. After 1 h reaction, the reaction mixture was concentrated under reduced pressure. 250 mL water was added and the mixture was extracted 3 times with 50 mL ethyl acetate. The organic phases were combined, dried over Na$_2$SO$_4$, filtered and concentrated under reduced pressure until constant weight to give 10.6 g of product (20a) (92% yield corrected for 91% purity by NMR with internal standard). [M+H]$^+$=290.2 [M+NH$_4$]$^+$=307.2 [M+Na]$^+$=312.2.

(S)-N-Boc-2-(2-Amino-ethyl)-2-hydroxymethyl-pentanoic acid ethyl ester (20b)

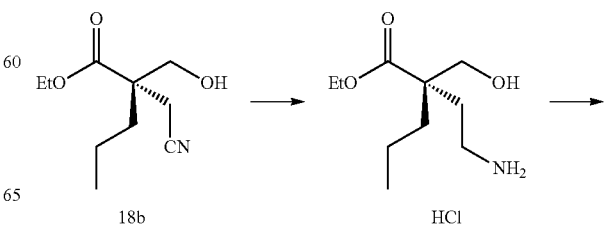

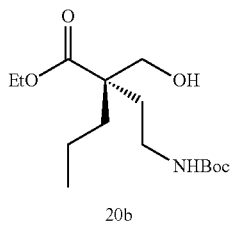

20b

Synthesis 40:

2 g of ester nitrile (18b) (10 mmol, 1 equiv.) charged in the reactor together with 40 mL of ethanol and 425 mg PtO2 (15 mol % PtO2) followed by 0.94 mL 37% $HCl_{aq}$ (11 mmol, 1.1 equiv.), The nitrile was hydrogenated at 50 bar/100° C. After completion of the reaction, the reaction mixture was degassed and cooled to RT, filtered. The catalyst was washed with 40 mL ethanol. To the crude amino ester product solution (19b) was added 2.46 g $Boc_2O$ (1.1 equiv.), followed by 4.2 mL $Et_3N$ (3 equiv.). After 1 h reaction at RT, the reaction mixture was concentrated. Water was added and the resulting mixture was extracted 3 times with 50 mL AcOEt. The organic phases were combined, dried over $Na_2SO_4$, rotavaped, followed by high vacuum drying to give 3.1 g of Boc-ester product (20b). MS: $C_{15}H_{29}NO_5$: 303.2052 (found)/303.2046 (calcd), Optical rotation: $[\alpha]_D^{20}$=−1.51 (c=0.996 in MeOH)

1-Benzyl-pyrrolidine-3-carboxylic acid methyl ester (21)

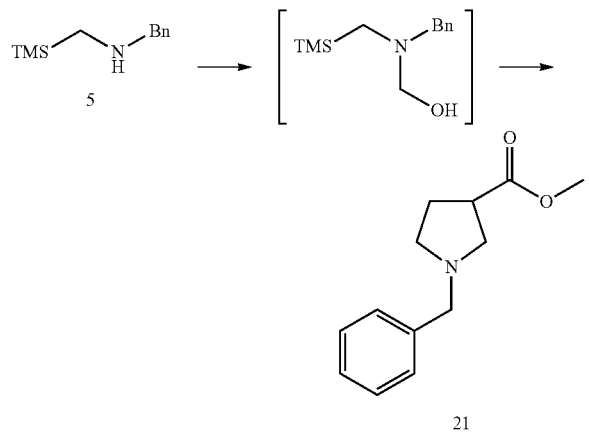

21

Synthesis 41:
Reactor A:

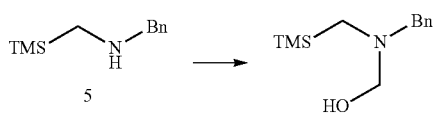 [SMILES: C[Si](C)(C)CNCc1ccccc1 ; C[Si](C)(C)CN(CO)Cc1ccccc1]

Benzyl-trimethylsilanylmethyl-amine (5) (100 g, 517 mmol, 1 equiv.) were charged in a 1 L jacketed reactor followed by 400 mL THF. The reaction temperature was set to 15° C. and 37% aqueous formaldehyde (53 mL, 647 mmol, 1.25 equiv) solution was added dropwise over ca 10 min keeping the temperature <30° C.

Reactor B:

In a separate reactor, 400 mL THF were charged (Tj=25° C.) followed by N-methylmorpholine (2.85 mL, 26 mmol, 0.05 equiv.), trifluoroacetic acid (TFA) (1 mL, 13 mmol, 0.025 equiv.) and methyl acrylate (56.5 mL, 621 mmol, 1.2 equiv.). The solution was heated to 50-55° C. and the solution from reactor A was added dropwise over ca 50 min. Ca 30 min after the end of addition (reaction complete as judged by IPC), the reactor was cooled to room temperature and the solution was concentrated to ca 500 mL. 250 mL heptane was added and the organic phase was washed twice with 250 mL water. The organic phase was dried over $MgSO_4$, concentrated under reduced pressure (down to 10-20 mbar, 45° C.) to give 108 g of crude product (21) (90% yield).

Synthesis 42:

Alternatively, (21) can be prepared in the following way. Paraformaldehyde (1.72 g, 54.3 mmol) was charged in the reactor followed by 100 mL THF and Benzyl-trimethylsilanylmethyl-amine (5) (10 g, 51.7 mmol). 1,1,3,3-tetramethylguanidine (119 mg, 130 µl, 1.03 mmol) was added to the suspension. The reaction mixture was stirred at RT for 1.5 h during which a clear solution was obtained. This solution was added dropwise over 30 min to a mixture consisting of TFA (301 mg, 203 µl, 2.59 mmol) and methyl acrylate (4.95 g, 56.9 mmol). After completion of the reaction (IPC by GC or HPLC, ca 3-5 h), the reaction mixture was concentrated under reduced pressure. The oily residue was dissolved in 25 mL MTBE and was washed twice washed with 60 mL water (60.0 g, 60 mL), then with 30 mL half saturated $NaHCO_3{}_{aq}$ and 25 mL half saturated $NaCl_{aq}$. The organic phase was dried over $MgSO_4$, filtered and concentrated under reduced pressure to give 10.4 g of product (21) (89% yield).

Synthesis 43:

Alternatively, (21) can be prepared in the following way. Benzyl-trimethylsilanylmethyl-amine (5) (958 g, 4954 mmol, 1 equiv.) were charged in a 16 L jacketed reactor followed by 5.3 L THF. The reaction temperature was set to 25° C. and 37% aqueous formaldehyde (509.5 g, 6193 mmol, 1.25 equiv) solution was added dropwise over 15-30 min. After 30 min at 25° C., methyl acrylate (474.6 g, 5458 mmol, 1.1 equiv.) was added over 15 min. A solution consisting of trifluoroacetic acid (16 mL, 205 mmol, 0.04 equiv.) in 480 mL THF was added in one portion, triggering the cycloaddition. After 17 h at 25° C. (IPC by GC, reaction takes approx. 8-10 h), the reaction mixture was concentrated (380-270 mbar/50° C.) to a volume of 4-5 L. 7.7 L toluene were added and the mixture was washed 4 times with 8 L of water. Activated charcoal (Norit SAII, 50 g) were added to the resulting organic phase. After stirring for 1 h at room temperature, the suspension was filtered and concentrated (down to 7 mbar/50° C.) to provide 1.068 kg of crude product (21) (ca 90% yield).

Pyrrolidine-1,3-dicarboxylic acid 1-tert-butyl ester 3-methyl ester (22)

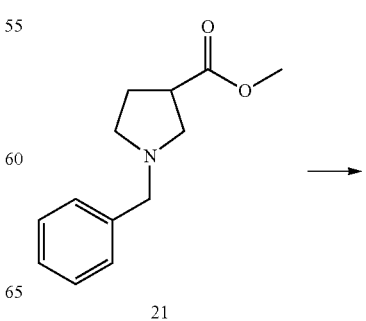

21

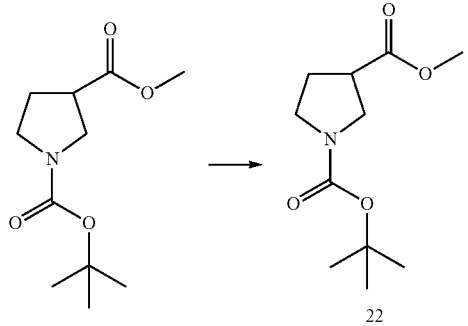

Synthesis 44:

1 kg N-Bn-pyrrolidine (21) from previous step (synthesis 43) (4414 mmol, 1 equiv.) was dissolved in 10 L methanol and hydrogenated at atmospheric pressure over 101 g Pd/C (95 mmol Pd, 0.02 equiv., 10% Degussa E101 N/D). After completion of the reaction, the catalyst was filtered and the solution was concentrated to ca 10 L. 2 L methanol were added and distilled at constant volume. A solution of 1.025 kg $Boc_2O$ (4603 mmol, 1.05 equiv) in 2.4 L methanol was added over 40 min keeping the temperature between 20-30° C. After completion of the reaction (GC IPC), the reaction mixture was concentrated under reduced pressure (50° C., 300 to 17 mbar) to give 998 g of (22) as a yellow oil. 4 L toluene was added and the solution was washed with 1.6 L of 0.5 M $HCl_{aq}$ and 1.6 L of 5% $NaHCO_3{}_{aq}$. The organic phase was dried over $Na_2SO_4$ and concentrated under reduced pressure (80 to 16 mbar, 50° C.) to give 975 g of crude product (22) as orange oil (98.6a % GC, 3.2% residual toluene).

(3,4-Dichloro-phenyl)-((S)-3-propyl-pyrrolidin-3-yl)-methanone hydrochloride (I) as quarterhydrate

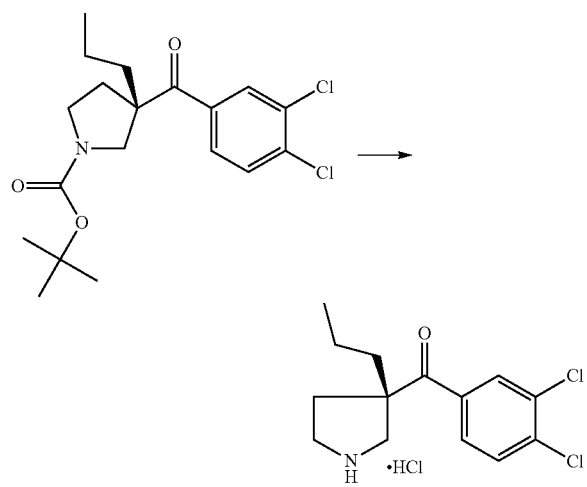

Synthesis 45:

The crude (14) from synthesis 31 was dissolved in 130 mL toluene and the solution was added dropwise to a mixture of 140 mL toluene and 70 mL 37% $HCl_{aq}$ at 60-70° C. ($CO_2$ formation, controlled dosing). After 1 h reaction, the reaction mixture was azeotroped with toluene (Tr max=70° C., Tj max=120° C., reduced pressure) and adjusted to a volume of ca 350-400 mL. A mixture consisting of 700 mL ethyl acetate and 3.6 mL water was added at ca 65° C. The solution was cooled to RT over ca 1 h during which crystallization started (around 45° C.). After stirring overnight, the suspension was cooled to 0-5° C. for 2 h, was filtered and washed twice with 200 mL ethyl acetate. The crystals were re-suspended in 250 mL ethyl acetate, digested at 55° C. for 2 h then cooled to RT and filtered. The filter cake was washed with 200 mL ethyl acetate. The crystals were dried at 50° C. under reduced pressure to give 54.4 g of the quarterhydrate of (I) as a white powder and 99.2a % purity (HPLC).

Synthesis 46:

Alternatively, quarterhydrate of (I) can be prepared in the following way. The crude (14) from synthesis 32 was dissolved in 63 mL toluene and deprotected at 60° C. with 24 mL 37% $HCl_{aq}$. After completion of the reaction, the reaction mixture was dried azeotropically with toluene at 50-60° C. (to remove water and excess HCl). The solution was cooled to RT and 100 mL water was added. The aqueous phase was separated and washed with 50 mL toluene. The aqueous phase was dried azeotropically with toluene and concentrated to dryness to give 22.5 g of quarterhydrate of (I) (ca 90% yield). Quaterhydrate of I can be obtained by digestion or recrystallization, for example, by processes described below.

Transformation of compound of formula I anhydrate to the quarterhydrate form:

Compound of formula I (40 g, 124 mmol, Eq: 1.00, anhydrate) was suspended in a mixture of ethyl acetate (340 ml), ethanol (36 ml) and water (0.6 ml) at room temperature. The suspension was heated to 40° C. and a mixture consisting of ethyl acetate (20 mL), ethanol (0.5 ml) and water (0.6 mL) was added over 1 h. The suspension was cooled to RT over 1 h. After stirring overnight at RT, the suspension was cooled to 2-3 h at 0-5° C., filtered and washed with a cold (0-5° C.) mixture of ethyl acetate (55 mL), ethanol (5 mL) and water (0.5 mL). The filter cake was dried at 50° C. under reduced pressure to give 38 g of product as quarterhydrate (1.5% water).

Recrystallisations of quarterhydrate of (I):

54.4 g of quarterhydrate of (I) were dissolved at RT in 550 mL ethanol. The solution was filtered and concentrated under reduce pressure at 60° C. to a volume of 140 mL. The volume was adjusted to 550 mL by addition of ethyl acetate. The rest of ethanol was solvent exchanged to ethyl acetate (Tj=60° C./reduced pressure). 55 mL ethanol were added to the resulting suspension at Tr=60° C. upon which a solution was obtained. 1.5 mL water was then added and the solution was slowly cooled to RT during which crystallization occurred. After stirring at RT overnight, the suspension was cooled to 0-5° C. for 1 h and filtered. The filter cake was washed with a mixture of 50 mL ethyl acetate and 5 mL ethanol followed by two washes with 50 mL ethyl acetate. The crystals were dried at 50° C. overnight under reduced pressure to give 48.9 g of quarterhydrate of (I) as a white powder and 99.7a % purity.

(3,4-Dichloro-phenyl)-((S)-3-propyl-pyrrolidin-3-yl)-methanone hydrochloride (I) in anhydrate form Synthesis 48:

50 g of sodium salt (12) were transformed into the corresponding acid chloride (13) as described above (in analogy to synthesis 31), reacted with the 3,4-dichlorophenyl-MgBr (A') as described above and Boc-deprotected following the process as described above to provide, after azeotrope drying, an orange turbid toluene solution (300 g, water content <0.1% by KFT of the crude (I).

i) ⅕ of this solution of crude (I) (synthesis 48) (max theoretical content: 11.3 g of (I)) was cooled to RT. After staying overnight at RT, the resulting suspension was filtered, washed with AcOEt (KFT of wet filter cake 0.2%) and dried at 50-60° C. under reduced pressure to give 5.9 g of crystals (I) (water<0.1% by KFT, anhydrate of I by X-ray).

ii) ⅕ of this solution of crude (I) (max theoretical content: 11.3 g of (I)) was cooled to RT. After staying 4 days at RT the resulting suspension was stirred at 0-2° C. for 4 h, filtered, washed with AcOEt, dried at 50-60° C. under reduced pressure to give 8.8 g of crystals (I) (water by KFT (Karl Fischer Titration): 0.2%, anhydrate of I by X-ray).

The invention claimed is:

1. A crystalline polymorph of (3,4-Dichloro-phenyl)-((S)-3-propyl-pyrrolidin-3-yl)-methanone hydrochloride of formula I

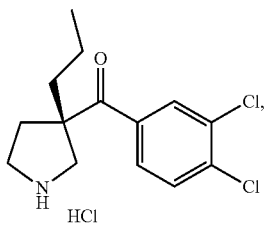

or a hydrate thereof.

2. The crystalline polymorph of claim 1 which is (3,4-Dichloro-phenyl)-((S)-3-propyl-pyrrolidin-3-yl)-methanone hydrochloride quarterhydrate.

3. The crystalline polymorph of the compound of claim 1, wherein the crystalline polymorph has an X-ray powder diffraction pattern having at least one characteristic peak expressed in values of degrees 2-theta at approximately

| degree 2-theta |
| --- |
| 5.5 |
| 9.4 |
| 10.6 |
| 12.5 |
| 14.6 |
| 16.2 |
| 16.6 |
| 17.3 |
| 18.6 |
| 19.6 |
| 22.2 |
| 22.7 |
| 23.1 |
| 23.7 |
| 25.3. |

4. The crystalline polymorph of the compound of claim 1, wherein the crystalline polymorph has an X-ray powder diffraction pattern having characteristic peaks expressed in values of degrees 2-theta at approximately

| degree 2-theta |
| --- |
| 5.5 |
| 9.4 |
| 10.6 |
| 12.5 |
| 14.6 |
| 16.2 |
| 16.6 |
| 17.3 |
| 18.6 |
| 19.6 |
| 22.2 |
| 22.7 |
| 23.1 |
| 23.7 |
| 25.3. |

5. The crystalline polymorph of the compound of claim 1, wherein the crystalline polymorph has an X-ray powder diffraction pattern as shown in FIG. 1.

6. Substantially pure crystalline polymorph of 3,4-Dichloro-phenyl)-((S)-3-propyl-pyrrolidin-3-yl)-methanone hydrochloride quarterhydrate according to claim 1.

7. The crystalline polymorph of the compound of claim 1, wherein the crystalline polymorph has the following unit cell parameters

| | |
| --- | --- |
| a | 6.14 Å |
| b | 16.70 Å |
| c | 17.43 Å |
| alpha | 66.73° |
| beta | 81.47° |
| gamma | 86.51°. |

8. The crystalline polymorph of the compound of claim 1, wherein the crystalline polymorph has an X-ray powder diffraction pattern having at least one characteristic peak expressed in values of degrees 2-theta at approximately

| degree 2-theta |
| --- |
| 5.2 |
| 10.5 |
| 12.3 |
| 15.3 |
| 15.6 |
| 16.0 |
| 17.1 |
| 18.8 |
| 23.0 |
| 23.9 |
| 27.2 |
| 28.2 |
| 30.5. |

9. The crystalline polymorph of the compound of claim 1, wherein the crystalline polymorph has an X-ray powder diffraction pattern as shown in FIG. 2.

10. A pharmaceutical composition comprising a crystalline polymorph of a compound of claim 1 and a pharmaceutically acceptable carrier.

11. A method for treating depression, anxiety, or both, said method comprising administering to a subject in need thereof an effective amount of a crystalline polymorph of a compound of claim 1.

* * * * *